United States Patent
Baley et al.

(10) Patent No.: US 9,091,681 B2
(45) Date of Patent: Jul. 28, 2015

(54) METHOD TO IDENTIFY DISEASE RESISTANT QUANTITATIVE TRAIT LOCI IN SOYBEAN AND COMPOSITIONS THEREOF

(71) Applicant: Monsanto Technology LLC, St. Louis, MO (US)

(72) Inventors: George James Baley, Webster Groves, MO (US); David Vincent Butruille, Des Moines, IA (US); Samuel R. Eathington, Ames, IA (US); Michael D. Haverdink, Gilbert, IA (US); Warren M. Kruger, West Des Moines, IA (US); John Robert LeDeaux, Creve Coeur, MO (US); Vergel C. Concibido, Maryland Heights, MO (US); James Narvel, Middletown, DE (US); John W. Pitkin, Wildwood, MO (US); John Tamulonis, Neveda, IA (US); Chongqing Xie, Johnston, IA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/191,044

(22) Filed: Feb. 26, 2014

(65) Prior Publication Data
US 2014/0206032 A1 Jul. 24, 2014

Related U.S. Application Data

(60) Continuation of application No. 13/529,851, filed on Jun. 21, 2012, now Pat. No. 8,692,054, which is a continuation of application No. 13/178,668, filed on Jul. 8, 2011, now Pat. No. 8,389,798, which is a continuation of application No. 12/472,906, filed on May 27, 2009, now Pat. No. 7,994,395, which is a division of application No. 11/805,667, filed on May 24, 2007, now Pat. No. 7,951,998.

(60) Provisional application No. 60/808,430, filed on May 25, 2006.

(51) Int. Cl.
*C12Q 1/68* (2006.01)
*C12N 5/04* (2006.01)
*G01N 33/50* (2006.01)

(52) U.S. Cl.
CPC .......... *G01N 33/5097* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 4,937,970 A | 7/1990 | Guan et al. |
| 7,097,975 B1 | 8/2006 | Frederick |
| 7,994,395 B2 | 8/2011 | Baley et al. |
| 2004/0031072 A1 | 2/2004 | La Rosa et al. |
| 2006/0041955 A1 | 2/2006 | Godwin et al. |
| 2006/0288444 A1 | 12/2006 | McCarroll et al. |
| 2009/0307799 A1 | 12/2009 | Baley et al. |

FOREIGN PATENT DOCUMENTS

WO 2008/054546 A2 5/2008

OTHER PUBLICATIONS

Alan et al., "Sensitivity of Bacterial and Fungal Plant Pathogens to the Lytic Peptides, MSI-99, Magainin II, and CecripinB," *MPMI*, 15(7):701-708 (2002).
Anderson et al., "Statistical Procedures for Assessment of Resistance in a Multiple Foliar Disease Complex of Peanut," *Phytopathology*, 80(12):1451-1459 (1990).
Arahana et al., "Identification of QTLs for Resistance to *Sclerotinia sclerotiorum* in Soybean," *Crop Science*, 41:180-188 (2001).
Banyal et al., "Resistance of pea genotypes in relation to sporulation by *Erysiphe pisi*," *Crop Protection*, 16(1):51-55 (1997).
Bhattacharyya et al., "Expression of gene-specific and age-related resistance and the accumulation of glyceollin in soybean leaves infected with *Phytophthora megasperma* f. sp. Glycinea," *Physiological and Molecular Plant Pathology*, 29:105-113 (1986).
Brogin, "Mapeamento de Genes de Resistencia a Ferrugem e de QTLs Envolvidos na Resistencia àSeptoriose em Soja," Univesidade de Sao Paulo, pp. 13-45 (2005).
Brogin et al., "Molecular mapping of a gene conferring resistance to soybean rust," Abstracts of Contributed Papers from the VII World Soybean Research Conference, p. 318 (2004).
Burdon et al., "Evaluation of Australian Native Species of *Glycine* for Resistance to Soybean Rust," *Plant Disease*, 65(1):44-45 (1981).
Bussey et al., "A Leaf Disk Assay for Detecting Resistance to Early Blight Caused by *Alternaria solani* in Juvenile Potato Plants," *Plant Disease*, 75(4):385-390 (1991).
Chang et al., "Two Additional Loci Underlying Durable Field Resistance to Soybean Sudden Death Syndrome (SDS)," *Crop Science*, 36:1684-1688 (1996).
Chen et al., "Two Convenient Methods to Evaluate Soybean for Resistance to *Sclerotinia sclerotiorum*," *Plant Disease*, 89(12):1268-1272 (2005).
Cline et al., "Methods for Evaluating Soybean Cultivars for Resistance to *Sclerotinia sclerotiorum*," *Plant Disease*, 67(7):784-786 (1983).
Cregan et al., "An Integrated Genetic Linkage Map of the Soybean Genome," *Crop Sci.*, 39:1464-1490 (1999).

(Continued)

*Primary Examiner* — Medina A Ibrahim
(74) *Attorney, Agent, or Firm* — Lawrence M. Lavin, Jr.; David R. Marsh; Arnold & Porter LLP

(57) ABSTRACT

The present invention is in the field of plant breeding and genetics, particularly as it pertains to the genus, *Glycine*. More specifically, the invention relates to a method for screening soybean plants containing one or more quantitative trait loci for disease resistance, species of *Glycine* having such loci and methods for breeding for and screening of *Glycine* with such loci. The invention further relates to the use of exotic germplasm in a breeding program.

18 Claims, No Drawings

(56) References Cited

OTHER PUBLICATIONS

Collard et al., "An introduction to markers, quantitative trait loci (QTL) mapping and marker-assisted selection for crop improvement: The basic concepts," *Euphytica*, 142:169-196 (2005).

Ding et al., "A putative IgG-binding 65 kDa adhesin involved in adhesion and infection of soybeans by *Phytophthora megasperma* f.sp. *glycinea*," *Physiological and Molecular Plant Pathology*, 44:363-378 (1994).

Dowkiw et al., "Partial Resistance to *Melampsora larici-populina* Leaf Rust in Hybrid Poplars: Genetic Variability in Inoculated Excised Leaf Disk Bioassay and Relationship with Complete Resistance," Phytopathology, 93(4): 421-427 (2003).

European Search Report issued on Jun. 11, 2012, in European Patent Application No. 11194511.9.

European Search Report issued on Jun. 13, 2012, in European Patent Application No. 11194514.3.

European Search Report issued on Jun. 19, 2012, in European Patent Application No. 11194515.0.

Examination Report dated Apr. 13, 2011, in European Patent Application No. 07 867 133.6, 7 pages.

Fehr et al., "Stage of Development Descriptions for Soybeans, *Glycine Max* (L.) Merrill," *Crop Science*, 11:929-931 (1971).

Frederick et al., "Polymerase Chain Reaction Assays for the Detection and Discrimination of the Soybean Rust Pathogens *Phakopsora pachyrhizi* and *P. meibomiae*," *Phytopathology*, 92(2):217-227 (2002).

Hartman et al., "Breeding for Resistance to Soybean Rust," *Plant Disease*, 89(6):664-666 (2005).

Hartwig et al., "Relationships Among Three Genes Conferring Specific Resistance to Rust in Soybeans," *Crop Science*, 23:237-239 (1983).

Herath et al., "Evaluating faba beans for rust resistance using detached leaves," *Euphytica*, 117:47-57 (2001).

Hershman et al., "Bacterial Leaf Blights," Soybean Disease Atlas, 2nd ed., P.D. Colyer (ed.), Associated Printing Professionals, Inc., 2 pages (1989).

Hsieh et al., "Leaf-disk method for assessment of disease severity of lily leaf blight caused by *Botrytis elliptica*," *Plant Pathology Bulletin*, 10:37-44 (2001).

Hyten et al., *Crop Science*, 47:837-840 (2007).

International Search Report issued on Jan. 16, 2009, in International Patent Application No. PCT/US2007/012363.

J.S. Melching, et al., "Effect of plant and leaf age on susceptibility of soybean to soybean rust," Canadian Journal of Plant Pathology 10:30-35, 1998.

Kasuga et al., "High Resolution Genetic and Physical Mapping of Molecular Markers Linked to the *Phytophthora* Resistance Gene *Rsp1*-in Soybean," *Molecular Plant-Microbe Interactions*, 10(9):1035-1044 (1997).

Kim et al., "Inheritance of Partial Resistance to Sclerotinia Stem Rot in Soybean", *Crop Science*, 40:55-61 (2000).

Kim et al., "Reaction of Soybean Cultivars to Sclerotinia Stem Rot in Field, Greenhouse, and Laboratory Evaluations," *Crop Science*, 40:665-669 (2000).

Kull et al., "Evaluation of Resistance Screening Methods for Sclerotinia Stem Rot of Soybean and Dry Bean," *Plant Disease*, 87:1471-1476 (2003).

Lebeda, "Screening of Wild *Cucumis* Species for Resistance to Cucumber Powdery Mildew (*Erysiphe cichoracearum* and *Sphaerotheca fuliginea*)," *Scientia Horticulturae*, 24:241-249 (1984).

Maxwell et al., "Effects of Water Stress on Colonization of Poplar Stems and Excised Leaf Disks by *Septoria musiva*," *Ecology and Population Biology*, 87(4):381-388 (1997).

Mieslerová et al., "Variation in Response of Wild *Lycopersicon* and *Solanum* spp. against Tomato Powdery Mildew (*Oidium lycopersici*)," *J. Phytopathology*, 148:303-311 (2000).

Nuntapunt et al., "Soybean breeding for rust resistance in Thailand and extent of rust resistant cultivars used," Proceedings VII World Soybean Research Conference, pp. 423-430 (2004).

Orlandi et al., "Early physiological responses associated with race-specific recognition in soybean leaf tissue and cell suspensions treated with *Pseudomonas syringae* pv. *Glycinea*," *Physiological and Molecular Plant Pathology*, 40:173-180 (1992).

Owens et al., "Genotypic Variability of Soybean Response to *Agrobacterium* Strains Harboring the Ti or Ri Plasmids," *Plant Physiol.*, 77:87-94 (1985).

Paul et al., "Potential of Detached Soybean Leaves for Evaluation of Rust Resistance," Presented at Molecular and Cellular Biology of the Soybean Conference, 1 page (2006).

Phillips, "Fungal Leaf Spots," Soybean Disease Atlas, 2nd ed., P.D. Colyer (ed.), Associated Printing Professionals, Inc., 6 pages (1989).

Pratt, "Screening for Resistance to *Sclerotinia trifoliorum* in Alfalfa by Inoculation of Excised Leaf Tissue," *Phytopathology*, 86(9):923-928 (1996).

Reddy et al., "Screening for powdery mildew (*Erysiphae polygoni* DC.) resistance in mungbean (*Vigna radiata* (L.) Wilczek) using excised leaves," *Proc. Indian Acad. Sci. (Plant Sci.)*, 97 (5):365-369 (1987).

Ruhl, "Crop Diseases in Corn, Soybean, and Wheat," Available at: http://www.btny.purdue.edu/extension/pathology/cropdiseases/soybean/Soybean.html, Purdue University, 7 pages (2007).

Robertson et al., "Soybean Rust and Common Soybean Leaf Diseases," *PM 1989*, Iowa State University, 4 pages (2008).

Shanmugasundaram et al., "Breeding for soybean rust resistance in Taiwan," Proceedings of the VII World Soybean Research Conference, pp. 456-462 (2004).

Sharma et al., "Identification of soybean strains resistant to *Xanthonomas campestris* pv. *Glycines*," *Euphytica*, 67:95-99 (1993).

Sillero et al., "Screening techniques and sources of resistance to rusts and mildews in grain legumes," *Euphytica*, 147:255-272 (2006).

Singh et al., "Sources of Field Resistance to Rust and Yellow Mosaic Diseases of Soybean," *Indian Journal of Genetics & Plant Breeding*, 34(3):400-404 (1974).

Smit, "Proceedings of Workshop on Soybean Rust (*Phakopsora pachyrhizi*)," ARC-Grain Crops Institute, 40 pages (1998).

Sweets et al., "Soybean Rust," *MU Guide, Bulletin G4442*, University of Missouri-Columbia, 6 pages (2004).

Twizeyimana et al., "A detached leaf method to evaluate soybean for resistance to rust," National Soybean Rust Symposium, 1 page (2006).

Twizeyimana et al., "Comparison of Field, Greenhouse, and Detached-Leaf Evaluations of Soybean Germplasm for Resistance to *Phakopsora pachyrhizi*," *Plant Disease*, 91(9):1161-1169 (2007).

Vodkin et al., "II-D. Testing for DNA Markers Associated with Rust Resistance in Soybean," Proceedings of the Soybean Rust Workshop, National Soybean Research Laboratory Publication, No. 1, p. 68 (1995).

Walters et al., "Induction of systemic resistance to rust in *Vicia faba* by phosphate and EDTA: effects of calcium," *Plant Pathology*, 41:444-448 (1992).

Wang et al., "Epidemiology of Soybean Rust and Breeding for Host Resistance," *Plant Protection Bulletin*, 34:109-124 (1992).

Ward et al., "Hypocotyl Reactions and Glyceollin in Soybeans Inoculated with Zoospores of *Physophthora megasperma* var. *sojae*," *Phytopathology*, 69(9):951-955 (1979).

Wegulo et al., "Soybean Cultivar Responses to *Sclerotinia sclerotiorum* in Field and Controlled Environment Studies," *Plant Disease*, 82(11):1264-1270 (1998).

Westman et al., "The potential for cross-taxa simple-sequence repeat (SSR) amplification between *Arabidopsis thaliana* L. and crop brassicas," *Theor Appl Genet*, 96:272-281 (1998).

Whitney, "Seedling Diseases," Soybean Disease Atlas, 2nd ed., P.D. Colyer (ed.), Associated Printing Professionals, Inc., 4 pages (1989).

Wynstra (ed.), The NSRL Bulletin, National Soybean Research Laboratory, University of Illinois, Urbana, IL, vol. 2, No. 3, p. 5 (1995).

Xie et al., "A Leaf Inoculation Method for Detection of *Xanthomonas oryzae* pv. *oryzicola* from Rice Seed," *Plant Disease*, 82:1007-1011 (1998).

Young, "QTL Mapping and Quantitative Disease Resistance in Plants," *Annu. Rev. Phytopathol.*, 34:479-501 (1996).

(56) References Cited

OTHER PUBLICATIONS

"Soybean Genetic Resources and Genetic Enhancement White Paper," Jan. 2000 (9 pages).
Lewers et al., "Detection of linked QTL for soybean brown stem rot resistance in 'BSR 101' as expressed in a growth chamber environment," *Molecular Breeding*, 5(1):33-42 (1999).
McLean et al., "Inheritance of resistance to rust (*Phakopsora pachyrhizi*) in soybeans," *Australian Journal of Agricultural Research*, 31(5):951-956 (1980).
Monteros et al., "Mapping and Confirmation of the 'Hyuuga' Red-Brown Lesion Resistance Gene for Asian Soybean Rust," *Crop Science* 47:829-836 (2007).
NPGS Soybean Accession PI200492, deposited Apr. 15, 1952.
NPGS Soybean Accession PI368037, deposited Nov. 26, 1971.
Partial International Search Report issued in PCT/US2009/041390 on May 19, 2009.
Silva et al., "Molecular mapping of two loci that confer resistance to Asian rust in soybean," *Theoretical and Applied Genetics* 117:57-63 (2008).

METHOD TO IDENTIFY DISEASE RESISTANT QUANTITATIVE TRAIT LOCI IN SOYBEAN AND COMPOSITIONS THEREOF

CROSS REFERENCE TO RELATED APPLICATIONS

This application is a continuation of U.S. patent application Ser. No. 13/529,851 filed on Jun. 21, 2012(U.S. Pat. No. 8,692,054), which is a continuation of U.S. patent application Ser. No. 13/178,668 filed on Jul. 8, 2011 (U.S. Pat. No. 8,389,798). U.S. patent application Ser. No. 13/178,668 is a continuation of U.S. patent application Ser. No. 12/472,906 filed on May 27, 2009 (U.S. Pat. No. 7,994,395), which is a divisional of U.S. patent application Ser. No. 11/805,667 filed on May 24, 2007 (U.S. Pat. No. 7,951,998), which claims the benefit of priority to U.S. Provisional Application Ser. No. 60/808,430 filed on May 25, 2006. Each of the aforementioned applications is herein incorporated by reference in its entirety.

INCORPORATION OF THE SEQUENCE LISTING

This application contains a sequence listing, submitted herewith electronically via EFS web, containing the file named "P30876US05_updatedseqlist.txt" which is 71 457 bytes in size (measured in Windows XP), which was created on Apr. 1, 2014, and which is herein incorporated by reference in its entirety.

FIELD OF THE INVENTION

The present invention is in the field of plant breeding and disease resistance. More specifically, the invention relates to a method for screening plants from the genus *Glycine* containing quantitative trait loci that are associated with disease resistance and methods for breeding disease resistant *Glycine* plants. The disease can be caused by a fungus, virus, bacterium, or invertebrate animal. The invention further relates to the use of accession germplasm containing quantitative trait loci (QTL) conferring disease resistance for introgression into elite germplasm in a breeding program for resistance to the fungal pathogen, *Phakopsora pachyrhizi*.

BACKGROUND OF THE INVENTION

The soybean, *Glycine max* (L.) Merril, is one of the major economic crops grown worldwide as a primary source of vegetable oil and protein (Sinclair and Backman, *Compendium of Soybean Diseases*, 3$^{rd}$ Ed. APS Press, St. Paul, Minn., p. 106. (1989)). The growing demand for low cholesterol and high fiber diets has also increased soybean's importance as a health food.

Soybean yields in the United States are reduced each year by diseases. High yields per hectare are critical to a farmer's profit margin, especially during periods of low prices for soybean. The financial loss caused by soybean diseases is important to rural economies and to the economies of allied industries in urban areas. The effects of these losses are eventually felt throughout the soybean market worldwide. Estimates of loss due to disease in the United States and Ontario vary from year to year and by disease. From 1999 to 2002 soybean yield loss estimates were in the range of 8 million metric tons to 10 million metric tons in the United States and 90,000 to 166,000 metric tons in Ontario (Wrather et al., Online. *Plant Health Progress* doi: 10: 1094/PHP-2003-0325-01-RV).

Asian Soybean Rust (herein referred to as ASR) has been reported in the Eastern and Western Hemispheres. In the Eastern Hemisphere, ASR has been reported in Australia, China, India, Japan, Taiwan and Thailand. In the Western Hemisphere, ASR has been observed in Brazil, Columbia, Costa Rica and Puerto Rico. ASR can be a devastating disease, causing yield losses of up to 70 to 80% as reported in some fields in Taiwan. Plants that are heavily infected have fewer pods and smaller seeds that are of poor quality (Frederick et al., *Mycology* 92: 217-227 (2002)). ASR was first observed in the United States in Hawaii in 1994. ASR was later introduced into the continental United States in the fall of 2004, presumably as a consequence of tropical storm activity. Model predictions indicated that ASR had been widely dispersed throughout the southeastern United States, and subsequent field and laboratory observations confirmed this distribution.

Two species of fungi, *Phakopsora pachyrhizi* Sydow and *Phakopsora meibomiae* (Arthur) Arthur, cause ASR. Unlike other rusts, *P. pachyrhizi* and *P. meibomiae* infect an unusually broad range of plant species. *P. pachyrhizi* is known to naturally infect 31 species in 17 genera of legumes and 60 species in 26 other genera have been infected under controlled conditions. *P. meibomiae* naturally infects 42 species in 19 genera of legumes, and 18 additional species in 12 other genera have been artificially infected. Twenty-four plant species in 19 genera are hosts for both species (Frederick et al., *Mycology* 92: 217-227 (2002)).

Soybean plants resistant to ASR have been identified. Four dominant, independently inherited race-specific QTL for resistance to *P. pachyrhizi*, herein designated ASR resistance locus 1, ASR resistance locus 2, ASR resistance locus 3, and ASR resistance locus 4, have been identified in PI 200492, PI 230970, PI 462312 (Ankur), and PI 459025B, respectively. These lines, as well as seven others, are suspected of containing QTL for ASR resistance. PI 239871A and PI 239871B (*G. soja*), PI 230971 and PI 459024B, and the cultivars Taita Kaohsiung-5, Tainung-4, and Wayne have been used as differentials to identify nine races at the Asian Vegetable Research and Development Center, in Taiwan. The predominant race was compatible with three or more of the differentials, indicating that some races already possess multiple virulence factors to known and suspected genes for resistance. Resistance also occurs among the wild *Glycine* spp. from Australia. Rate-reducing resistance has also been demonstrated. However, it is difficult to evaluate this type of resistance because the rate of rust development is dependent on soybean development and maturity (Sinclair et al., eds., Soybean rust workshop. College of Agricultural, Consumer, and Environmental Sciences. Natl. Soybean Res. Lab. Publ. 1 (1996)).

Evaluating plants that could potentially contain QTL conferring resistance to ASR can be time consuming and require large amounts of biologically contained space. Culturing *P. pachyrhizi* requires the use of an approved biological containment hood. In addition, greenhouses and growth chambers used to grow plants for ASR resistance testing will have to be constructed in a manner that prevents the accidental release of the organism, especially in locations in which the organism has still not yet been observed. Different cultures of *P. pachyrhizi* may possess different virulence factors. Over time, new strains of *P. pachyrhizi* may be introduced into the United States. Therefore, any breeding program designed to breed resistance into soybean against ASR will need to be able to respond rapidly to changes in the *P. pachyrhizi* population. Also, breeding for soybean crops used in other geographic locations will require selecting resistance to the specific strains that affect those regions, in addition to providing those agronomic characteristics that are preferred by these farmers in that region. Therefore, there is a great need for a rapid, time and cost efficient high throughput method for screening germplasm resistant to ASR. This method must not only provide speed and efficiency, but must also be able to be performed with a minimal amount of space, allowing for the screening of many samples at one time.

The present invention provides a method for screening and selecting a soybean plant comprising QTL for disease resistance.

SUMMARY OF THE INVENTION

The present invention provides a method for assaying soybean plants for disease resistance, immunity, or susceptibility comprising: (a) detaching a plant tissue from the soybean plant; (b) cultivating said tissue in a media; (c) exposing said tissue to a plant pathogen; and (d) assessing said tissue for resistance, immunity, or susceptibility to disease caused by the pathogen. Additionally, the plant response to the pathogen can be evaluated by the following steps (e) isolating nucleic acids (DNA and/or RNA) from said plant; (f) assaying said nucleic acids (DNA, RNA, and/or cDNA) for the presence of one or more molecular markers for a quantitative trait locus associated with said resistance, immunity, or susceptibility; and (g) selecting said plant for use in a breeding program. Determination of resistance, immunity, or susceptibility of a plant to a particular pathogen is obvious to anyone skilled in the art. The plant tissue can be leaf, vascular tissue, flower, pod, root, stem, seed, or a portion thereof, or a cell isolated from the tissue. Exposing said tissue to a plant pathogen is accomplished by a means selected from the group consisting of (a) direct application of the pathogen to the tissue; (b) inclusion of the pathogen in the culture media; and (c) inclusion of an agent that is effectively contaminated with the pathogen and serves to inoculate the tissue. The plant pathogen can be a fungus, virus, bacterium, or invertebrate animal. The plant pathogen exposure can be in the form of pathogen macromolecules, cells, tissues, whole organism or combinations thereof, wherein the pathogen, and parts thereof, is either living or dead so long that the material mediates an immune response in the host tissue. Pathogen macromolecules relevant for the present invention include, but are not limited to, toxins, cell walls or membranes, antigens, and polysaccharides.

The present invention further comprises a QTL that confers disease resistance to a fungal pathogen selected from the group consisting of *Phakopsora pachyrhizi, Phakopsora meibomiae* (Asian Soybean Rust), *Colletotrichum truncatum, Colletotrichum dematium* var. *truncatum, Glomerella glycines* (Soybean Anthracnose), *Phytophthora sojae* (*Phytophthora* root and stem rot), *Sclerotinia sclerotiorum* (*Sclerotinia* stem rot), *Fusarium solani* f. sp. *glycines* (sudden death syndrome), *Fusarium* spp. (*Fusarium* root rot), *Macrophomina phaseolina* (charcoal rot), *Septoria glycines*, (Brown Spot), *Pythium aphanidermatum, Pythium debaryanum, Pythium irregulare, Pythium ultimum, Pythium myriotylum, Pythium torulosum* (*Pythium* seed decay), *Diaporthe phaseolorum* var. *sojae* (Pod blight), *Phomopsis longicola* (Stem blight), *Phomopsis* spp. (*Phomopsis* seed decay), *Peronospora manshurica* (Downy Mildew), *Rhizoctonia solani* (*Rhizoctonia* root and stem rot, *Rhizoctonia* aerial blight), *Phialophora gregata* (Brown Stem Rot), *Diaporthe phaseolorum* var. *caulivora* (Stem Canker), *Cercospora kikuchii* (Purple Seed Stain), *Alternaria* sp. (Target Spot), *Cercospora sojina* (Frogeye Leafspot), *Sclerotium rolfsii* (Southern blight), *Arkoola nigra* (Black leaf blight), *Thielaviopsis basicola*, (Black root rot), *Choanephora infundibulifera, Choanephora trispora* (*Choanephora* leaf blight), *Leptosphaerulina trifolii* (*Leptosphaerulina* leaf spot), *Mycoleptodiscus terrestris* (*Mycoleptodiscus* root rot), *Neocosmospora vasinfecta* (*Neocosmospora* stem rot), *Phyllosticta sojicola* (*Phyllosticta* leaf spot), *Pyrenochaeta glycines* (*Pyrenochaeta* leaf spot), *Cylindrocladium crotalariae* (Red crown rot), *Dactuliochaeta glycines* (Red leaf blotch), *Spaceloma glycines* (Scab), *Stemphylium botryosum* (*Stemphylium* leaf blight), *Corynespora cassiicola* (Target spot), *Nematospora coryli* (Yeast spot), and *Phymatotrichum omnivorum* (Cotton Root Rot).

The present invention further comprises a QTL that confers disease resistance to a viral pathogen selected from the group consisting of Alfamovirus (Alfafa mosaic virus, AMV), Comovirus (bean pod mottle virus, BPMV), Potyvirus (bean yellow mosaic virus, BYMV), Bromovirus (cowpea chlorotic mottle virus, CCMV), Begomovirus (mung bean yellow mosaivc virus, MYMV), Potyvirus (peanut mottle virus, PeMoV), Potyvirus (peanut stripe virus, PStV), Cucumovirus (peanut stunt virus, PSV), Caulimovirus (soybean chlorotic mottle virus, SbCMV), Begomovirus (soybean crinkle leaf virus, SCLV), Luteovirus (soybean dwarf virus, SbDV), Potyvirus (soybean mosaic virus, SMV), Nepovirus (soybean severe stunt virus, SSSV), and Nepovirus (tobacco ringspot virus, TRSV).

The present invention further comprises a QTL that confers disease resistance to a bacterial pathogen selected from the group consisting of *Bacillus subtilis* (*Bacillus* seed decay), *Pseudomonas savastonoi* pv. *glycinea* (Bacterial blight), *Pseudomonas syringae* subsp. *syringae* (Bacterial crinkle-leaf), *Xanthomonas axonopodis* pv. *glycines*, (Bacterial pustule), *Curtobacterium flaccumfaciens* pv. *flaccumfaciens*, (Bacterial tan spot), *Curtobacterium flaccumfaciens* pv. *flaccumfaciens, Ralstonia solanacearum*, (Bacterial wilt), and *Pseudomonas syringae* pv. *tabaci* (Wildfire).

The present invention further comprises a QTL that confers disease resistance to a invertebrate pathogen selected from the group consisting of *Aphis glycines* (Soybean aphid), *Heterodera glycines* (Soybean cyst nematode), *Meloidogyne arenaria, Meloidogyne hapla, Meloidogyne incognita, Meloidogyne javanica* (Root knot nematode), *Hoplolaimus Columbus, Hoplolaimus galeatus, Hoplolaimus magnistylus* (Lance nematode), *Pratylenchus* spp. (Lesion nematode), *Paratylenchus projectus, Paratylenchus tenuicaudatus* (Pin nematode), *Rotylenchulus reniformis* (Reniform nematode), *Criconemella ornata* (Ring nematode), *Hemicycliophora* spp. (Sheath nematode), *Heliocotylenchus* spp. (Spiral nematode), *Belonolainus gracilis, Belonolainus longicaudatus* (Sting nematode), *Quinisulcius acutus, Tylenchorhynchus* spp. (Stunt nematode), and *Paratrichodorus minor* (Stubby root nematode).

The present invention also provides selected soybean tissue and plants that are resistant to *Phakopsora pachyrhizi, Phakopsora meibomiae* (Asian Soybean Rust), *Colletotrichum truncatum, Colletotrichum dematium* var. *truncatum, Glomerella glycines* (Soybean Anthracnose), *Phytophthora sojae* (*Phytophthora* root and stem rot), *Sclerotinia sclerotiorum* (*Sclerotinia* stem rot), *Fusarium solani* f. sp. *glycines* (sudden death syndrome), *Fusarium* spp. (*Fusarium* root rot), *Macrophomina phaseolina* (charcoal rot), *Septoria glycines*, (Brown Spot), *Pythium aphanidermatum, Pythium debaryanum, Pythium irregulare, Pythium ultimum, Pythium myriotylum, Pythium torulosum* (*Pythium* seed decay), *Diaporthe* phaseolorum var. sojae (Pod blight), *Phomopsis longicola* (Stem blight), *Phomopsis* spp. (*Phomopsis* seed decay), *Peronospora manshurica* (Downy Mildew), *Rhizoctonia solani* (*Rhizoctonia* root and stem rot, *Rhizoctonia* aerial blight), *Phialophora gregata* (Brown Stem Rot), *Diaporthe phaseolorum* var. *caulivora* (Stem Canker), *Cercospora kikuchii* (Purple Seed Stain), *Alternaria* sp. (Target Spot), *Cercospora sojina* (Frogeye Leafspot), *Sclerotium rolfsii* (Southern blight), *Arkoola nigra* (Black leaf blight), *Thielaviopsis basicola*, (Black root rot), *Choanephora infundibulifera*, *Choanephora trispora* (*Choanephora* leaf blight), *Leptosphaerulina trifolii* (*Leptosphaerulina* leaf spot), *Mycoleptodiscus terrestris* (*Mycoleptodiscus* root rot), *Neocosmospora vasinfecta* (*Neocosmospora* stem rot), *Phyllosticta sojicola* (*Phyllosticta* leaf spot), *Pyrenochaeta glycines* (*Pyrenochaeta* leaf spot), *Cylindrocladium crotalariae* (Red crown rot), *Dactuliochaeta glycines* (Red leaf blotch), *Spaceloma glycines* (Scab), *Stemphylium botryosum* (*Stemphylium* leaf blight), *Corynespora cassiicola* (Target spot), *Nematospora coryli* (Yeast spot), *Phymatotrichum omnivorum* (Cotton Root Rot), Alfafa mosaic virus, AMV), Comovirus (bean pod mottle virus, BPMV), Potyvirus (bean yellow mosaic virus, BYMV), Bromovirus (cowpea chlorotic mottle virus, CCMV), Begomovirus (mung bean yellow mosaivc virus, MYMV), Potyvirus (peanut mottle virus, PeMoV), Potyvirus (peanut stripe virus, PStV), Cucumovirus (peanut stunt virus, PSV), Caulimovirus (soybean chlorotic mottle virus, SbCMV), Begomovirus (soybean crinkle leaf virus, SCLV), Luteovirus (soybean dwarf virus, SbDV), Potyvirus (soybean mosaic virus, SMV), Nepovirus (soybean severe stunt virus, SSSV), Nepovirus (tobacco ringspot virus, TRSV), *Bacillus subtilis* (*Bacillus* seed decay), *Pseudomonas savastonoi* pv. *glycinea* (Bacterial blight), *Pseudomonas syringae* subsp. *syringae* (Bacterial crinkle-leaf), *Xanthomonas axonopodis* pv. *glycines*, (Bacterial pustule), *Curtobacterium flaccumfaciens* pv. *flaccumfaciens*, (Bacterial tan spot), *Curtobacterium flaccumfaciens* pv. *flaccumfaciens*, *Ralstonia solanacearum*, (Bacterial wilt), *Pseudomonas syringae* pv. *tabaci* (Wildfire), *Aphis glycines* (Soybean aphid), *Heterodera glycines* (Soybean cyst nematode), *Meloidogyne arenaria*, *Meloidogyne hapla*, *Meloidogyne incognita*, *Meloidogyne javanica* (Root knot nematode), *Hoplolaimus Columbus*, *Hoplolaimus galeatus*, *Hoplolaimus magnistylus* (Lance nematode), *Pratylenchus* spp. (Lesion nematode), *Paratylenchus projectus*, *Paratylenchus tenuicaudatus* (Pin nematode), *Rotylenchulus reniformis* (Reniform nematode), *Criconemella ornata* (Ring nematode), *Hemicycliophora* spp. (Sheath nematode), *Heliocotylenchus* spp. (Spiral nematode), *Belonolainus gracilis*, *Belonolainus longicaudatus* (Sting nematode), *Quinisulcius acutus*, *Tylenchorhynchus* spp. (Stunt nematode), or *Paratrichodorus minor* (Stubby root nematode).

The present invention further provides that the selected plant is from the group consisting of members of the genus *Glycine*, more specifically from the group consisting of *Glycine arenaria*, *Glycine argyrea*, *Glycine canescens*, *Glycine clandestine*, *Glycine curvata*, *Glycine cyrtoloba*, *Glycine falcate*, *Glycine latifolia*, *Glycine latrobeana*, *Glycine max*, *Glycine microphylla*, *Glycine pescadrensis*, *Glycine pindanica*, *Glycine rubiginosa*, *Glycine soja*, *Glycine* sp., *Glycine stenophita*, *Glycine tabacina* and *Glycine tomentella*.

The present invention further provides that the media used in the method for selection is comprised of water that is untreated, distilled or deionized. The media can contain any ingredients necessary to sustain the pathogen or plant tissue, so long as the ingredients do not interfere with the expression of resistance as conferred by the QTL.

The present invention further provides a soybean plant selected using said method.

The present invention also provides a QTL that is selected from the group consisting of *Phytophthora* (root rot) infection tolerance locus, *Fusarium solani* f. sp. *glycines* (sudden death syndrome) resistance locus, *Cercospora sojina* (Frogeye leaf spot) resistance locus, *Phialophora gegata* (brown stem rot) resistance locus, *Sclerotinia* (stem rot) resistance locus, ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13.

The present invention further provides that the selected plant contains one or more fungal disease resistance QTL, including ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13.

The present invention further provides one or more single nucleotide polymorphism (SNP) marker loci for ASR resistance locus 1, wherein said SNP marker is selected from the group consisting of NS0093250, NS0119710, NS0103004, NS0099454, NS0102630, NS0102915, NS0102913, NS0123728, NS0129943, NS0102168, NS0092723, NS0098177, NS0127343, and NS0101121. One or more SNP marker loci for ASR resistance locus 3 are also provided, wherein said SNP marker is selected from the group consisting of NS0099746, NS0123747, NS0126598, NS0128378, NS0096829, NS0125408, NS0098902, NS0099529, NS0097798, NS0137477, NS0095322, NS0136101, and NS0098982. An exemplary SNP marker locus, NS0103033, is provided for ASR resistance locus 5, ASR resistance locus 6, ASR resistance locus 7, ASR resistance locus 8, and ASR resistance locus 9. Another exemplary SNP marker locus, NS0124935, is provided for ASR resistance locus 10, ASR resistance locus 11, ASR resistance locus 12, and ASR resistance locus 13. Further, one or more markers mapped within 10 centimorgans or less from said marker molecules can be used for the selection and introgression of ASR resistance loci.

The present invention further provides a method for selecting and introgressing ASR resistance in soybean comprising: (a) isolating nucleic acids from a plurality of soybean plants; (b) detecting in said isolated nucleic acids the presence of one or more marker molecules associated with ASR resistance loci 1-13, wherein said marker molecule is selected from the group consisting of SEQ ID NOs: 67 through 99, and any one marker molecule mapped within 10 centimorgans or less from said marker molecules; and (c) selecting a soybean plant comprising said one or more marker molecules, thereby selecting an ASR resistant soybean plant.

The present invention further provides for a soybean plant selected using said method.

DETAILED DESCRIPTION OF THE INVENTION

The present invention provides a method for screening soybean plants for resistance, immunity, or susceptibility to a fungal disease. In a preferred embodiment the plant is selected from the genus *Glycine*. The wild perennial soybeans belong to the subgenus *Glycine* and have a wide array of genetic diversity. The cultivated soybean (*Glycine max* (L.) Merr.) and its wild annual progenitor (*Glycine soja* (Sieb. and Zucc.)) belong to the subgenus *Soja*, contain 2n=40 chromosomes, are cross-compatible, usually produce vigorous fertile F1 hybrids, and carry similar genomes. Crosses between cultivated *Glycine* species and wild perennial *Glycine* species are possible, the success of which is variable amongst accessions. Investigations have shown that several wild perennial *Glycine* accessions carry resistance to brown spot, soybean rust, root rot, yellow mosaic virus, and powdery mildew. There are more than 100,000 *Glycine max* accessions, probably less than 10,000 *Glycine soja* accessions and approximately, 3500 accessions of perennial *Glycine* species in germplasm collections throughout the world. The exact numbers are unknown. Major *Glycine* collections exist in Australia, Brazil, China, Germany, India, Indonesia, Japan, Russia, South Korea, and the United States. Many other smaller but important collections exist throughout Asia and Europe. It is not known how many of the accessions are duplicated among collections. The USDA Soybean Germplasm Collection is one of the largest collections and the largest outside Asia (Verma et al., eds., Soybean: Genetics, Molecular Biology and Biotechnology (1996)). It currently contains 20,765 accessions, comprised of 19 species collections, including 18,680 accessions of *Glycine max* and 1,166 accessions of *Glycine soja* as well as perennial *Glycine* species.

In a preferred embodiment, a soybean plant is assayed for disease resistance, immunity, or susceptibility comprising: (a) detaching a plant tissue from the soybean plant; (b) cultivating said tissue in a media; (c) exposing said tissue to a plant pathogen; and (d) assessing said tissue for resistance, immunity, or susceptibility to disease caused by the pathogen. Additionally, the plant response to the pathogen can be evaluated by the following steps (e) isolating nucleic acids from said plant; (f) assaying said nucleic acids for the presence of one or more molecular markers for a quantitative trait locus associated with said resistance, immunity, or susceptibility; and (g) selecting said plant for use in a breeding program. Determination of resistance, immunity, or susceptibility of a plant to a particular pathogen is obvious to anyone skilled in the art. The plant tissue can be leaf, vascular tissue, flower, pod, root, stem, seed, or a portion thereof, or a cell isolated from the tissue. Exposing said tissue to a plant pathogen is accomplished by a means selected from the group consisting of (a) direct application of the pathogen to the tissue; (b) inclusion of the pathogen in the culture media; and (c) inclusion of an agent that is effectively contaminated with the pathogen and serves to inoculate the tissue. The plant pathogen can be a fungus, virus, bacterium, or invertebrate animal. The plant pathogen exposure can be in the form of pathogen macromolecules, cells, tissues, whole organism or combinations thereof, wherein the pathogen, and parts thereof, is either living or dead so long that the material mediates an immune response in the host tissue. Pathogen macromolecules relevant for the present invention include, but are not limited to, toxins, cell walls or membranes, antigens, and polysaccharides.

In a preferred embodiment, the leaf tissue may comprise a cotyledon leaf, unifoliate leaf, a trifoliate leaf, and prophylls. There are four types of soybean leaves: 1) the first pair of simple cotyledons or seed leaves, 2) second pair of simple primary leaves, also known as unifoliate leaves, 3) trifoliate foliage leaves, and 4) prophylls, which are plant parts resembling leaves. The unifoliate leaves occur at the first node above the cotyledons. All other leaves would be trifoliates, wherein the first pair to emerge following the unifoliates are the first trifoliate leaves, which are followed by the emergence of the second trifoliates leaves and then the third trifoliate leaves (H. R. Boerma and J. E. Specht (ed.) Soybean Monograph, 3rd Edition, Am. Soc. Agron., Madison, Wis. (2004)).

In a preferred embodiment, the present invention enables a soybean plant to be assayed for resistance, immunity, or susceptibility to a fungal disease. Soybean diseases caused by fungi include, but are not limited to, *Phakopsora pachyrhizi*, *Phakopsora meibomiae* (Asian Soybean Rust), *Colletotrichum truncatum*, *Colletotrichum dematium* var. *truncatum*, *Glomerella glycines* (Soybean Anthracnose), *Phytophthora sojae* (*Phytophthora* root and stem rot), *Sclerotinia sclerotiorum* (*Sclerotinia* stem rot), *Fusarium solani* f. sp. *glycines* (sudden death syndrome), *Fusarium* spp. (*Fusarium* root rot), *Macrophomina phaseolina* (charcoal rot), *Septoria glycines*, (Brown Spot), *Pythium aphanidermatum*, *Pythium debaryanum*, *Pythium irregulare*, *Pythium ultimum*, *Pythium myriotylum*, *Pythium torulosum* (*Pythium* seed decay), *Diaporthe phaseolorum* var. *sojae* (Pod blight), *Phomopsis longicola* (Stem blight), *Phomopsis* spp. (*Phomopsis* seed decay), *Peronospora manshurica* (Downy Mildew), *Rhizoctonia solani* (*Rhizoctonia* root and stem rot, *Rhizoctonia* aerial blight), *Phialophora gregata* (Brown Stem Rot), *Diaporthe phaseolorum* var. *caulivora* (Stem Canker), *Cercospora kikuchii* (Purple Seed Stain), *Alternaria* sp. (Target Spot), *Cercospora sojina* (Frogeye Leafspot), *Sclerotium rolfsii* (Southern blight), *Arkoola nigra* (Black leaf blight), *Thielaviopsis basicola*, (Black root rot), *Choanephora infundibulifera*, *Choanephora trispora* (*Choanephora* leaf blight), *Leptosphaerulina trifolii* (*Leptosphaerulina* leaf spot), *Mycoleptodiscus terrestris* (*Mycoleptodiscus* root rot), *Neocosmospora vasinfecta* (*Neocosmospora* stem rot), *Phyllosticta sojicola* (*Phyllosticta* leaf spot), *Pyrenochaeta glycines* (*Pyrenochaeta* leaf spot), *Cylindrocladium crotalariae* (Red crown rot), *Dactuliochaeta glycines* (Red leaf blotch), *Spaceloma glycines* (Scab), *Stemphylium botryosum* (*Stemphylium* leaf blight), *Corynespora cassiicola* (Target spot), *Nematospora coryli* (Yeast spot), and *Phymatotrichum omnivorum* (Cotton Root Rot).

In a preferred embodiment, the present invention enables a soybean plant to be assayed for resistance, immunity, or susceptibility to a viral disease. Soybean diseases caused by viruses include, but are not limited to, Alfamovirus (Alfafa mosaic virus, AMV), Comovirus (bean pod mottle virus, BPMV), Potyvirus (bean yellow mosaic virus, BYMV), Bromovirus (cowpea chlorotic mottle virus, CCMV), Begomovirus (mung bean yellow mosaivc virus, MYMV), Potyvirus (peanut mottle virus, PeMoV), Potyvirus (peanut stripe virus, PStV), Cucumovirus (peanut stunt virus, PSV), Caulimovirus (soybean chlorotic mottle virus, SbCMV), Begomovirus (soybean crinkle leaf virus, SCLV), Luteovirus (soybean dwarf virus, SbDV), Potyvirus (soybean mosaic virus, SMV), Nepovirus (soybean severe stunt virus, SSSV), and Nepovirus (tobacco ringspot virus, TRSV).

In a preferred embodiment, the present invention enables a soybean plant to be assayed for resistance, immunity, or susceptibility to a bacterial disease. Soybean diseases caused by bacteria include, but are not limited to, *Bacillus subtilis* (*Bacillus* seed decay), *Pseudomonas savastonoi* pv. *glycinea* (Bacterial blight), *Pseudomonas syringae* subsp. *syringae* (Bacterial crinkle-leaf), *Xanthomonas axonopodis* pv. *glycines*, (Bacterial pustule), *Curtobacterium flaccumfaciens* pv. *flaccumfaciens*, (Bacterial tan spot), *Curtobacterium flaccumfaciens* pv. *flaccumfaciens*, *Ralstonia solanacearum*, (Bacterial wilt), and *Pseudomonas syringae* pv. *tabaci* (Wildfire).

In a preferred embodiment, the present invention enables a soybean plant to be assayed for resistance, immunity, or susceptibility to an animal pest disease. Soybean diseases caused by animal pests include, but are not limited to *Aphis glycines* (Soybean aphid), *Heterodera glycines* (Soybean cyst nematode), *Meloidogyne arenaria, Meloidogyne hapla, Meloidogyne incognita, Meloidogyne javanica* (Root knot nematode), *Hoplolaimus Columbus, Hoplolaimus galeatus, Hoplolaimus magnistylus* (Lance nematode), *Pratylenchus* spp. (Lesion nematode), *Paratylenchus projectus, Paratylenchus tenuicaudatus* (Pin nematode), *Rotylenchulus reniformis* (Reniform nematode), *Criconemella ornata* (Ring nematode), *Hemicycliophora* spp. (Sheath nematode), *Heliocotylenchus* spp. (Spiral nematode), *Belonolainus gracilis, Belonolainus longicaudatus* (Sting nematode), *Quinisulcius acutus, Tylenchorhynchus* spp. (Stunt nematode), and *Paratrichodorus minor* (Stubby root nematode).

The invention further provides a method for selection and introgression of QTL for disease resistance in soybean comprising: (a) isolating nucleic acids from a plurality of soybean plants; (b) detecting in said isolated nucleic acids the presence of one or more marker molecules associated with disease resistance QTL; and (c) selecting a soybean plant comprising said one or more marker molecules, thereby selecting a disease resistant soybean plant.

The disease resistance QTL of the present invention may be introduced into an elite *Glycine max* line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety 115050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 ROUNDUP READY™, HARTZ™ variety H4994 ROUNDUP READY™, HARTZ™ variety H4988 ROUNDUP READY™, HARTZ™ variety H5000 ROUNDUP READY™, HARTZ™ variety 115147 ROUNDUP READY™, HARTZ™ variety H5247 ROUNDUP READY™, HARTZ™ variety 115350 ROUNDUP READY™, HARTZ™ variety H5545 ROUNDUP READY™, HARTZ™ variety 115855 ROUNDUP READY™, HARTZ™ variety H5088 ROUNDUP READY™, HARTZ™ variety H5164 ROUNDUP READY™, HARTZ™ variety H5361 ROUNDUP READY™, HARTZ™ variety H5566 ROUNDUP READY™, HARTZ™ variety H5181 ROUNDUP READY™, HARTZ™ variety H5889 ROUNDUP READY™, HARTZ™ variety H5999 ROUNDUP READY™, HARTZ™ variety H6013 ROUNDUP READY™, HARTZ™ variety H6255 ROUNDUP READY™, HARTZ™ variety H6454 ROUNDUP READY™, HARTZ™ variety H6686 ROUNDUP READY™, HARTZ™ variety H7152 ROUNDUP READY™, HARTZ™ variety H7550 ROUNDUP READY™, HARTZ™ variety H8001 ROUNDUP READY™ (HARTZ SEED, Stuttgart, Ark., USA); A0868, AG0202, AG0401, AG0803, AG0901, A1553, A1900, AG1502, AG1702, AG1901, A1923, A2069, AG2101, AG2201, AG2205, A2247, AG2301, A2304, A2396, AG2401, AG2501, A2506, A2553, AG2701, AG2702, AG2703, A2704, A2833, A2869, AG2901, AG2902, AG2905, AG3001, AG3002, A3101, A3204, A3237, A3244, AG3301, AG3302, AG3006, AG3203, A3404, A3469, AG3502, AG3503, AG3505, AG3305, AG3602, AG3802, AG3905, AG3906, AG4102, AG4201, AG4403, AG4502, AG4603, AG4801, AG4902, AG4903, AG5301, AG5501, AG5605, AG5903, AG5905, A3559, AG3601, AG3701, AG3704, AG3750, A3834, AG3901, A3904, A4045 AG4301, A4341, AG4401, AG4404, AG4501, AG4503, AG4601, AG4602, A4604, AG4702, AG4703, AG4901, A4922, AG5401, A5547, AG5602, AG5702, A5704, AG5801, AG5901, A5944, A5959, AG6101, AJW2600C0R, FPG26932, QR4459 and QP4544 (Asgrow Seeds, Des Moines, Iowa, USA); DKB26-52, DKB28-51, DKB32-52, DKB08-51, DKB09-53, DKB10-52, DKB18-51, DKB26-53, DKB29-51, DKB42-51, DKB35-51 DKB34-51, DKB36-52, DKB37-51, DKB38-52, DKB46-51, DKB54-52 and DeKalb variety CX445 (DeKalb, Ill., USA); 91B91, 92B24, 92B37, 92B63, 92B71, 92B74, 92B75, 92B91, 93B01, 93B11, 93B26, 93B34, 93B35, 93B41, 93B45, 93B51, 93B53, 93B66, 93B81, 93B82, 93B84, 94B01, 94B32, 94B53, 94M80 RR, 94M50 RR, 95B71, 95B95, 95M81 RR, 95M50 RR, 95M30 RR, 9306, 9294, 93M50, 93M93, 94B73, 94B74, 94M41, 94M70, 94M90, 95B32, 95B42, 95843 and 9344 (Pioneer Hi-bred International, Johnston, Iowa, USA); SSC-251RR, SSC-273CNRR, AGRA 5429RR, SSC-314RR, SSC-315RR, SSC-311STS, SSC-320RR, AGRA5432RR, SSC-345RR, SSC-356RR, SSC-366, SSC-373RR and AGRA5537CNRR (Schlessman Seed Company, Milan, Ohio, USA); 39-E9, 44-R4, 44-R5, 47-G7, 49-P9, 52-Q2, 53-K3, 56-J6, 58-V8, ARX A48104, ARX B48104, ARX B55104 and GP530 (Armor Beans, Fisher, Ark., USA); HT322STS, HT3596STS, L0332, L0717, L1309CN, L1817, L1913CN, L1984, L2303CN, L2495, L2509CN, L2719CN, L3997CN, L4317CN, RC1303, RC1620, RC1799, RC1802, RC1900, RC1919, RC2020, RC2300, RC2389, RC2424, RC2462, RC2500, RC2504, RC2525, RC2702, RC2964, RC3212, RC3335, RC3354, RC3422, RC3624, RC3636, RC3732, RC3838, RC3864, RC3939, RC3942, RC3964, RC4013, RC4104, RC4233, RC4432, RC4444, RC4464, RC4842, RC4848, RC4992, RC5003, RC5222, RC5332, RC5454, RC5555, RC5892, RC5972, RC6767, RC7402, RT0032, RT0041, RT0065, RT0073, RT0079, RT0255, RT0269, RT0273, RT0312, RT0374, RT0396, RT0476, RT0574, RT0583, RT0662, RT0669, RT0676, RT0684, RT0755, RT0874, RT0907, RT0929, RT0994, RT0995, RT1004, RT1183, RT1199, RT1234, RT1399, RT1413, RT1535, RT1606, RT1741, RT1789, RT1992, RT2000, RT2041, RT2089, RT2092, RT2112, RT2127, RT2200, RT2292, RT2341, RT2430, RT2440, RT2512, RT2544, RT2629, RT2678, RT2732, RT2800, RT2802, RT2822, RT2898, RT2963, RT3176, RT3200, RT3253, RT3432, RT3595, RT3836, RT4098, RX2540, RX2944, RX3444 and TS466RR (Croplan Genetics, Clinton, Ky., USA); 4340RR, 4630RR, 4840RR, 4860RR, 4960RR, 4970RR, 5260RR, 5460RR, 5555RR, 5630RR and 5702RR (Delta Grow, England, Ark., USA); DK3964RR, DK3968RR, DK4461RR, DK4763RR, DK4868RR, DK4967RR, DK5161RR, DK5366RR, DK5465RR, DK55T6, DK5668RR, DK5767RR, DK5967RR, DKXTJ446, DKXTJ448, DKXTJ541, DKXTJ542, DKXTJ543, DKXTJ546, DKXTJ548, DKXTJ549, DKXTJ54J9, DKXTJ54×9, DKXTJ554, DKXTJ555, DKXTJ55J5 and DKXTJ5K57 (Delta King Seed Company, McCrory, Ark., USA); DP 3861RR, DP 4331 RR, DP 4546RR, DP 4724 RR, DP 4933 RR, DP 5414RR, DP 5634 RR, DP 5915 RR, DPX 3950RR, DPX 4891RR, DPX 5808RR (Delta & Pine Land Company, Lubbock, Tex., USA); DG31T31, DG32C38, DG3362NRR, DG3390NRR, DG33A37, DG33B52, DG3443NRR, DG3463NRR, DG3481NRR, DG3484NRR, DG3535NRR, DG3562NRR, DG3583NRR, DG35B40, DG35D33, DG36M49, DG37N43, DG38K57, DG38T47, SX04334, SX04453 (Dyna-gro line, UAP-MidSouth, Cordova, Tenn., USA); 8374RR CYSTX, 8390 NNRR, 8416RR, 8492NRR and 8499NRR (Excel Brand, Camp Point, Ill., USA); 4922RR, 5033RR, 5225RR and 5663RR (FFR Seed, Southhaven, Miss., USA); 3624RR/N, 3824RR/N, 4212RR/N, 4612RR/N, 5012RR/N, 5212RR/N and 5412RR/STS/N (Garst Seed Company, Slater, Iowa, USA); 471, 4R451, 4R485, 4R495, 4RS421 and 5R531 (Gateway Seed Company, Nashville, Ill., USA); H-3606RR, H-3945RR, H-4368RR, H-4749RR, H-5053RR and H-5492RR (Golden Harvest Seeds, Inc., Pekin, Ill., USA); HBK 5324, HBK 5524, HBK R4023, HBK R4623, HBK R4724, HBK R4820, HBK R4924, HBK R4945CX, HBK RS620 and HBK RS624 (Hornbeck Seed Co. Inc., DeWitt, Ark., USA); 341 RR/SCN, 343 RR/SCN, 346 RR/SCN, 349 RR, 355 RR/SCN, 363 RR/SCN, 373 RR, 375 RR, 379 RR/SCN, 379+RR/SCN, 380 RR/SCN, 380+ RR/SCN, 381 RR/SCN, 389 RR/SCN, 389+RR/SCN, 393 RR/SCN, 393+RR/SCN, 398 RR, 402 RR/SCN, 404 RR, 424 RR, 434 RR/SCN and 442 RR/SCN (Kruger Seed Company, Dike, Iowa, USA); 3566, 3715, 3875, 3944, 4010 and 4106 (Lewis Hybrids, Inc., Ursa, Ill., USA); C3999NRR (LG Seeds, Elmwood, Ill., USA); Atlanta 543, Austin RR, Cleveland VIIRR, Dallas RR, Denver RRSTS, Everest RR, Grant 3RR, Olympus RR, Phoenix IIIRR, Rocky RR, Rushmore 553RR and Washington IXRR (Merschman Seed Inc., West Point, Iowa, USA); RT 3304N, RT 3603N, RT 3644N, RT 3712N, RT 3804N, RT 3883N, RT 3991N, RT 4044N, RT 4114N, RT 4124N, RT 4201N, RT 4334N, RT 4402N, RT 4480N, RT 4503N, RT 4683N, RT 4993N, RT 5043N, RT 5204, RT 5553N, RT 5773, RT4731N and RTS 4824N (MFA Inc., Columbia, Mo., USA); 9A373NRR, 9A375XRR, 9A385NRS, 9A402NRR, 9A455NRR, 9A485XRR and 9B445NRS (Midland Genetics Group L.L.C., Ottawa, Kans., USA); 3605nRR, 3805nRR, 3903nRR, 3905nRR, 4305nRR, 4404nRR, 4705nRR, 4805nRR, 4904nRR, 4905nRR, 5504nRR and 5505nRR (Midwest Premium Genetics, Concordia, Mo., USA); S37-N4, S39-K6, S40-R9, S42-P7, S43-B1, S49-Q9, S50-N3, S52-U3 and S56-D7 (Syngenta Seeds, Henderson, Ky., USA); NT-3707 RR, NT-3737 RR/SCN, NT-3737+RR/SCN, NT-3737sc RR/SCN, NT-3777+RR, NT-3787 RR/SCN, NT-3828 RR, NT-3839 RR, NT-3909 RR/SCN/STS, NT-3909+RR/SCN/ST, NT-3909sc RR/SCN/S, NT-3919 RR, NT-3922 RR/SCN, NT-3929 RR/SCN, NT-3999 RR/SCN, NT-3999+RR/SCN, NT-3999sc RR/SCN, NT-4040 RR/SCN, NT-4040+RR/SCN, NT-4044 RR/SCN, NT-4122 RR/SCN, NT-4414 RR/SCN/STS, NT-4646 RR/SCN and NT-4747 RR/SCN (NuTech Seed Co., Ames, Iowa, USA); PB-3494NRR, PB-3732RR, PB-3894NRR, PB-3921NRR, PB-4023NRR, PB-4394NRR, PB-4483NRR and PB-5083NRR (Prairie Brand Seed Co., Story City, Iowa, USA); 3900RR, 4401RR, 4703RR, 4860RR, 4910, 4949RR, 5250RR, 5404RR, 5503RR, 5660RR, 5703RR, 5770, 5822RR, PGY 4304RR, PGY 4604RR, PGY 4804RR, PGY 5622RR and PGY 5714RR (Progeny Ag Products, Wynne, Ark., USA); R3595RCX, R3684Rcn, R3814RR, R4095Rcn, R4385Rcn and R4695Rcn (Renze Hybrids Inc., Carroll, Iowa, USA); S3532-4, S3600-4, 53832-4, S3932-4, S3942-4, S4102-4, S4542-4 and S4842-4 (Stine Seed Co., Adel, Iowa, USA); 374RR, 398RRS (Taylor Seed Farms Inc., White Cloud, Kans., USA); USG 5002T, USG 510nRR, USG 5601T, USG 7440nRR, USG 7443nRR, USG 7473nRR, USG 7482nRR, USG 7484nRR, USG 7499nRR, USG 7504nRR, USG 7514nRR, USG 7523nRR, USG 7553nRS and USG 7563nRR (Uni-South Genetics Inc., Nashville, Tenn., USA); V38N5RS, V39N4RR, V42N3RR, V48N5RR, V284RR, V28N5RR, V31SRR, V35N4RR, V36N5RR, V37N3RR, V40N3RR, V47N3RR, and V562NRR (Royster-Clark Inc., Washington C.H., Ohio, USA); RR2383N, 2525NA, RR2335N, RR2354N, RR2355N, RR2362, RR2385N, RR2392N, RR2392NA, RR2393N, RR2432N, RR2432NA, RR2445N, RR2474N, RR2484N, RR2495N and RR2525N (Willcross Seed, King City Seed, King City, Mo., USA); 1493RR, 1991NRR, 2217RR, 2301NRR, 2319RR, 2321NRR, 2341NRR, 2531NRR, 2541NRR, 2574RR, 2659RR, 2663RR, 2665NRR, 2671NRR, 2678RR, 2685RR, 2765NRR, 2782NRR, 2788NRR, 2791NRR, 3410RR, 3411NRR, 3419NRR, 3421NRR, 3425NRR, 3453NRR, 3461NRR, 3470CRR, 3471NRR, 3473NRR, 3475RR, 3479NRR, 3491NRR, 3499NRR, WX134, WX137, WX177 and WX300 (Wilken Seeds, Pontiac, Ill., USA). An elite plant is a representative plant from an elite line.

The disease resistance QTL of the present invention may also be introduced into an elite *Glycine max* transgenic plant that contains one or more genes for herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in *Glycine max*.

It is further understood that a soybean plant of the present invention may exhibit the characteristics of any maturity group. The pollen from the selected soybean plant can be cryopreserved and used in crosses with elite lines from other maturity groups to introgress a the fungal disease resistance locus into a line that would not normally be available for crossing in nature. Pollen cryopreservation techniques are well known in the art (Tyagi et al., *Cryo Letters*, 24: 119-124 (2003), Liang et al., *Acta Botanica Sinica*, 35: 733-738 (1993), and Honda et al., *Euphytica* 126: 315-320 (2002)).

The disease resistant effect of the QTL can vary based on the parental genotype and on the environmental conditions in which the disease resistance effect is measured. It is within the skill of those in the art of plant breeding and without undue experimentation to use the methods described herein to select from a population of plants or from a collection of parental genotypes those that when containing a disease locus result in enhanced disease resistance relative to the parent genotype. Herein, a plant disease can be caused by a fungi, virus, bacterium or invertebrate animal.

A number of molecular genetic maps of *Glycine* have been reported (Mansur et al., *Crop Sci.* 36: 1327-1336 (1996), Shoemaker et al., *Genetics* 144: 329-338 (1996), Shoemaker et al., *Crop Science* 32: 1091-1098 (1992), Shoemaker et al., *Crop Science* 35: 436-446 (1995), Tinley et al. *J. Cell Biochem. Suppl.* 14E: 291 (1990), Cregan et al., *Crop Science* 39:1464-1490 (1999)). *Glycine max, Glycine soja* and *Glycine max* x. *Glycine soja* share linkage groups (Shoemaker et al., *Genetics* 144: 329-338 (1996)). As used herein, reference to the linkage groups, G; C2; J; and N of *Glycine max* refers to the linkage group that corresponds to linkage groups, G; C2; J; and N from the genetic map of *Glycine max* (Mansur et al., *Crop Science*. 36: 1327-1336 (1996), Cregan et al., *Crop Science* 39:1464-1490 (1999), and Soybase, Agricultural Research Service, United States Department of Agriculture).

An allele of a QTL can, of course, comprise multiple genes or other genetic factors even within a contiguous genomic region or linkage group, such as a haplotype. As used herein, an allele of a QTL can therefore encompasses more than one gene or other genetic factor where each individual gene or genetic component is also capable of exhibiting allelic variation and where each gene or genetic factor is also capable of eliciting a phenotypic effect on the quantitative trait in question. In an embodiment of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein said polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc.). A cultivar is a race or variety of a plant that has been created or selected intentionally and maintained through cultivation.

Selected, non-limiting approaches for breeding the plants of the present invention are set forth below. A breeding program can be enhanced using marker assisted selection (MAS) of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination event, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new soybean cultivars requires the development and selection of soybean varieties, the crossing of these varieties and selection of superior hybrid crosses. The hybrid seed can be produced by manual crosses between selected male-fertile parents or by using male sterility systems. Hybrids are selected for certain single gene traits such as pod color, flower color, seed yield, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g., Fehr, *Principles of Cultivar Development* Vol. 1, pp. 2-3 (1987)).

The present invention also provides for parts of the plants of the present invention. Plant parts, without limitation, include seed, endosperm, ovule and pollen. In a particularly preferred embodiment of the present invention, the plant part is a seed.

Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, eds. Verma and Shoemaker, CAB International, Wallingford, Oxon, England (1996)). Regeneration techniques for plants such as *Glycine max* can use as the starting material a variety of tissue or cell types. With *Glycine max* in particular, regeneration processes have been developed that begin with certain differentiated tissue types such as meristems (Cartha et al., *Can. J. Bot.* 59:1671-1679 (1981)), hypocotyl sections (Cameya et al., *Plant Science Letters* 21: 289-294 (1981)), and stem node segments (Saka et al., *Plant Science Letters,* 19: 193-201 (1980), Cheng et al., *Plant Science Letters,* 19: 91-99 (1980)). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985)). Regeneration of mature *Glycine ma* plants from tissue culture by organogenesis and embryogenesis has also been reported (Barwale et al., *Planta* 167: 473-481 (1986), Wright et al., *Plant Cell Reports* 5: 150-154 (1986)).

The present invention also provides a disease resistant soybean plant selected for by screening for disease resistance, immunity, or susceptibility in the soybean plant, the selection comprising interrogating genomic nucleic acids for the presence of a marker molecule that is genetically linked to an allele of a QTL associated with disease resistance in the soybean plant, where the allele of a QTL is also located on a linkage group associated with disease resistant soybean. The disease can be caused by a fungus, virus, bacterium, or invertebrate animal.

The present invention also provides for QTL conferring resistance to Asian Soybean Rust, including ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13. Four dominant and independently inherited loci for resistance to *P. pachyrhizi*, herein designated ASR resistance locus 1 through 4, have been identified in PI 200492, PI 230970, PI 462312 (Ankur), and PI 459025B, respectively. In the present invention, ASR resistance locus 1 has been localized to linkage group G of soybean. SNP markers used to monitor the introgression of ASR resistance locus 1 are selected from the group consisting of NS0093250, NS0119710, NS0103004, NS0099454, NS0102630, NS0102915, NS0102913, NS0123728, NS0129943, NS0102168, NS0092723, NS0098177, NS0127343 and NS0101121. The ASR resistance locus 1 SNP marker DNA sequences (presented as SEQ ID NOs: 67 through 80) can be amplified using the primers indicated as SEQ ID NOs: 1 through 28 and detected with probes indicated as SEQ ID NOs: 100 through 127. In the present invention, ASR resistance locus 2 is most likely located on linkage group J, near or within the disease resistance cluster containing Brown Stem Rot, Soybean Cyst Nematode resistance and Frog Eye Leaf Spot resistance; or linkage group N. In the present invention, ASR resistance locus 3 is localized to linkage group C2. SNP markers used to monitor the introgression of ASR resistance locus 3 are selected from the group consisting of NS0099746, NS0123747, NS0126598, NS0128378, NS0096829, NS0125408, NS0098902, NS0099529, NS0097798, NS0137477, NS0095322, NS0136101, NS0098982, NS0103749, NS0118897, NS0119715, and NS0130920. These marker DNA sequences (presented as SEQ ID NOs:81 through 97) can be amplified using the primers indicated as SEQ ID NOs: 29 through 62 and detected with probes indicated as SEQ ID NOs: 128 through 161. In the present invention, ASR resistance locus 4 is likely located on linkage group N.

The present invention also provides for haplotypes that confer resistance to ASR that were identified in association studies. These genome-wide surveys revealed two SNP markers associated with ASR resistance located in two different windows on chromosome 13. In the first haplotype window, the SNP marker used to monitor the introgression of ASR resistance locus 5, ASR resistance locus 6, ASR resistance locus 7, ASR resistance locus 8, and ASR resistance locus 9 is NS0103033. This SNP marker DNA sequences (presented as SEQ ID NO: 98) can be amplified using the primers indicated as SEQ ID NOs: 63 and 64 and detected with probes indicated as SEQ ID NOs: 162 and 163. In the second haplotype window, the SNP marker used to monitor the introgression of ASR resistance locus 10, ASR resistance locus 11, ASR resistance locus 12, and ASR resistance locus 13 is NS0124935. This SNP marker DNA sequences (presented as SEQ ID NO: 99) can be amplified using the primers indicated as SEQ ID NOs: 65 and 66 and detected with probes indicated as SEQ ID NOs: 164 and 165.

It is further understood, that one or more markers mapped within 10 centimorgans or less from said marker molecules can be used for the selection and introgression of ASR resistance loci.

It is further understood, that the present invention provides bacterial, viral, microbial, insect, mammalian and plant cells comprising the agents of the present invention.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual,* 2nd Edition, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., (1989) at 9.47-9.52, 9.56-9.58, Kanehisa *Nucl. Acids Res.* 12:203-213, (1984), and Wetmur et al., *J. Mol. Biol.* 31:349-370 (1968). Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

As used herein, an agent, be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al., *Science* 238:336-340 (1987), European Patent 144914), chemical labels (U.S. Pat. No. 4,582,789, U.S. Pat. No. 4,563,417), modified bases (European Patent 119448), all of which are herein incorporated by reference in their entirety).

In a preferred embodiment, a nucleic acid of the present invention will specifically hybridize to one or more of the nucleic acid molecules set forth in SEQ ID NO: 67 through SEQ ID NO: 99 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO: 67 through SEQ ID NO: 99 or complements or fragments of either under high stringency conditions. In one aspect of the present invention, a preferred marker nucleic acid molecule of the present invention has the nucleic acid sequence set forth in SEQ ID NO: 67 through SEQ ID NO: 99 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 67 through SEQ ID NO: 99 or complement thereof or fragments of either. In a further aspect of the present invention, a preferred marker nucleic acid molecule of the present invention shares between 95% and 100% sequence identity with the sequence set forth in SEQ ID NO: 67 through SEQ ID NO: 99 or complement thereof or fragments of either. In a more preferred aspect of the present invention, a preferred marker nucleic acid molecule of the present invention shares between 98% and 100% sequence identity with the nucleic acid sequence set forth in SEQ ID NO: 67 through SEQ ID NO: 99 or complement thereof or fragments of either.

Additional genetic markers can be used to select plants with an allele of a QTL associated with fungal disease resistance of soybean of the present invention. Examples of public marker databases include, for example: Soybase, an Agricultural Research Service, United States Department of Agriculture.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Markers, such as simple sequence repeat markers (SSR), AFLP markers, RFLP markers, RAPD markers, phenotypic markers, SNPs, isozyme markers, microarray transcription profiles that are genetically linked to or correlated with alleles of a QTL of the present invention can be utilized (Walton, Seed World 22-29 (July, 1993), Burow et al., Molecular Dissection of Complex Traits, 13-29, ed. Paterson, CRC Press, New York (1988)). Methods to isolate such markers are known in the art. For example, locus-specific SSR markers can be obtained by screening a genomic library for microsatellite repeats, sequencing of "positive" clones, designing primers which flank the repeats, and amplifying genomic DNA with these primers. The size of the resulting amplification products can vary by integral numbers of the basic repeat unit. To detect a polymorphism, PCR products can be radiolabeled, separated on denaturing polyacrylamide gels, and detected by autoradiography. Fragments with size differences >4 bp can also be resolved on agarose gels, thus avoiding radioactivity.

The detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction (PCR) (Mullis et al., Cold Spring Harbor Symp. Quant. Biol. 51:263-273 (1986), European Patent Appln. 50,424, European Patent 84,796, European Patent 258,017, European Patent 237,362, European Patent 201,184, U.S. Pat. No. 4,683,202, U.S. Pat. No. 4,582,788, U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" (LCR) may be used (Barany, Proc. Natl. Acad. Sci. (U.S.A.) 88:189-193 (1991), the entirety of which is herein incorporated by reference). LCR uses two pairs of oligonucleotide probes to exponentially amplify a specific target. The sequence of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

The "Oligonucleotide Ligation Assay" (OLA) may alternatively be employed (Landegren et al., Science 241:1077-1080 (1988), the entirety of which is herein incorporated by reference). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560-569 (1989), the entirety of which is herein incorporated by reference), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (U.S. Pat. No. 5,130,238, European Patent 329,822, U.S. Pat. No. 5,169,766, European Patent 359,789, Kwoh, et al., Proc. Natl. Acad. Sci. (U.S.A.) 86:1173-1177 (1989) European Patent 368,906, Walker et al., Proc. Natl. Acad. Sci. (U.S.A.) 89:392-396 (1992), all of which are herein incorporated by reference in their entirety).

Polymorphisms can also be identified by Single Strand Conformation Polymorphism (SSCP) analysis. SSCP is a method capable of identifying most sequence variations in a single strand of DNA, typically between 150 and 250 nucleotides in length (Elles, Methods in Molecular Medicine: Molecular Diagnosis of Genetic Diseases, Humana Press (1996); Orita et al., Genomics 5: 874-879 (1989)). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis.

A central attribute of SNPs is that the site of the polymorphism is at a single nucleotide. SNPs are more stable than other classes of polymorphisms. Their spontaneous mutation rate is approximately $10^{-9}$ (Kornberg, DNA Replication, W. H. Freeman & Co., San Francisco (1980)). As SNPs result from sequence variation, new polymorphisms can be identified by sequencing random genomic or cDNA molecules. SNPs can also result from deletions, point mutations and insertions. That said, SNPs are also advantageous as markers since they are often diagnostic of "identity by descent" because they rarely arise from independent origins. Any single base alteration, whatever the cause, can be a SNP. SNPs occur at a greater frequency than other classes of polymorphisms and can be more readily identified. In the present invention, a SNP can represent a single indel event, which may consist of one or more base pairs, or a single nucleotide polymorphism.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or by other biochemical interpretation. SNPs can be sequenced using a variation of the chain termination method (Sanger et al., Proc. Natl. Acad. Sci. (U.S.A.) 74: 5463-5467 (1977)) in which the use of radioisotopes are replaced with fluorescently-labeled dideoxy nucleotides and subjected to capillary based automated sequencing (U.S. Pat. No. 5,332,666, the entirety of which is herein incorporated by reference; U.S. Pat. No. 5,821,058, the entirety of which is herein incorporated by reference). Automated sequencers are available from, for example, Applied Biosystems, Foster City, Calif. (3730×1 DNA Analyzer), Beckman Coulter, Fullerton, Calif. (CEQ™ 8000 Genetic Analysis System) and LI-COR, Inc., Lincoln, Nebr. (4300 DNA Analysis System).

Approaches for analyzing SNPs can be categorized into two groups. The first group is based on primer-extension assays, such as solid-phase minisequencing or pyrosequencing. In the solid-phase minisequencing method, a DNA polymerase is used specifically to extend a primer that anneals immediately adjacent to the variant nucleotide. A single labeled nucleoside triphospate complementary to the nucleotide at the variant site is used in the extension reaction. Only those sequences that contain the nucleotide at the variant site will be extended by the polymerase. A primer array can be fixed to a solid support wherein each primer is contained in four small wells, each well being used for one of the four nucleoside triphospates present in DNA. Template DNA or RNA from each test organism is put into each well and allowed to anneal to the primer. The primer is then extended one nucleotide using a polymerase and a labeled di-deoxy nucleotide triphosphate. The completed reaction can be imaged using devices that are capable of detecting the label which can be radioactive or fluorescent. Using this method several different SNPs can be visualized and detected (Syvänen et al., *Hum. Mutat.* 13: 1-10 (1999)). The pyrosequencing technique is based on an indirect bioluminometric assay of the pyrophosphate (PPi) that is released from each dNTP upon DNA chain elongation. Following Klenow polymerase mediated base incorporation, PPi is released and used as a substrate, together with adenosine 5-phosphosulfate (APS), for ATP sulfurylase, which results in the formation of ATP. Subsequently, the ATP accomplishes the conversion of luciferin to its oxi-derivative by the action of luciferase. The ensuing light output becomes proportional to the number of added bases, up to about four bases. To allow processivity of the method dNTP excess is degraded by apyrase, which is also present in the starting reaction mixture, so that only dNTPs are added to the template during the sequencing procedure (Alderborn et al., *Genome Res.* 10: 1249-1258 (2000)). An example of an instrument designed to detect and interpret the pyrosequencing reaction is available from Biotage, Charlottesville, Va. (PyroMark MD).

A more recent SNP detection method, based on primer-extension assays is the GOOD assay. The GOOD assay (Sauer et al., *Nucleic Acids Res.* 28: e100 (2000)) is an allele-specific primer extension protocol that employs MALDI-TOF (matrix-assisted laser desorption/ionization time-of-flight) mass spectrometry. The region of DNA containing a SNP is amplified first by PCR amplification. Residual dNTPs are destroyed using an alkaline phosphatase. Allele-specific products are then generated using a specific primer, a conditioned set of a-S-dNTPs and a-S-ddNTPs and a fresh DNA polymerase in a primer extension reaction. Unmodified DNA is removed by 5' phosphodiesterase digestion and the modified products are alkylated to increase the detection sensitivity in the mass spectrometric analysis. All steps are carried out in a single vial at the lowest practical sample volume and require no purification. The extended reaction can be given a positive or negative charge and is detected using mass spectrometry (Sauer et al., *Nucleic Acids Res.* 28: e13 (2000)). An instrument in which the GOOD assay is analyzed is for example, the AUTOFLEX® MALDI-TOF system from Bruker Daltonics (Billerica, Mass.).

The second group, which is based on recognition of heteroduplex DNA molecules, includes oligonucleotide hybridization, TAQ-MAN® assays, molecular beacons, electronic dot blot assays and denaturing high-performance liquid chromatography. Oligonucleotide hybridizations can be performed in mass using micro-arrays (Southern, *Trends Genet.* 12: 110-115 (1996)). TAQ-MAN® assays, or Real Time PCR, detects the accumulation of a specific PCR product by hybridization and cleavage of a double-labeled fluorogenic probe during the amplification reaction. A TAQ-MAN® assay includes four oligonucleotides, two of which serve as PCR primers and generate a PCR product encompassing the polymorphism to be detected. The other two are allele-specific fluorescence-resonance-energy-transfer (FRET) probes. FRET probes incorporate a fluorophore and a quencher molecule in close proximity so that the fluorescence of the fluorophore is quenched. The signal from a FRET probes is generated by degradation of the FRET oligonucleotide, so that the fluorophore is released from proximity to the quencher, and is thus able to emit light when excited at an appropriate wavelength. In the assay, two FRET probes bearing different fluorescent reporter dyes are used, where a unique dye is incorporated into an oligonucleotide that can anneal with high specificity to only one of the two alleles. Useful reporter dyes include 6-carboxy-4,7,2',7'-tetrachlorofluorecein (TET), 2'-chloro-7'-phenyl-1,4-dichloro-6-carboxyfluorescein (VIC) and 6-carboxyfluorescein phosphoramidite (FAM). A useful quencher is 6-carboxy-N,N,N',N'-tetramethylrhodamine (TAMRA). Annealed (but not non-annealed) FRET probes are degraded by TAQ DNA polymerase as the enzyme encounters the 5' end of the annealed probe, thus releasing the fluorophore from proximity to its quencher. Following the PCR reaction, the fluorescence of each of the two fluorescers, as well as that of the passive reference, is determined fluorometrically. The normalized intensity of fluorescence for each of the two dyes will be proportional to the amounts of each allele initially present in the sample, and thus the genotype of the sample can be inferred. An example of an instrument used to detect the fluorescence signal in TAQ-MAN® assays, or Real Time PCR are the 7500 Real-Time PCR System (Applied Biosystems, Foster City, Calif.).

Molecular beacons are oligonucleotide probes that form a stem-and-loop structure and possess an internally quenched fluorophore. When they bind to complementary targets, they undergo a conformational transition that turns on their fluorescence. These probes recognize their targets with higher specificity than linear probes and can easily discriminate targets that differ from one another by a single nucleotide. The loop portion of the molecule serves as a probe sequence that is complementary to a target nucleic acid. The stem is formed by the annealing of the two complementary arm sequences that are on either side of the probe sequence. A fluorescent moiety is attached to the end of one arm and a nonfluorescent quenching moiety is attached to the end of the other arm. The stem hybrid keeps the fluorophore and the quencher so close to each other that the fluorescence does not occur. When the molecular beacon encounters a target sequence, it forms a probe-target hybrid that is stronger and more stable than the stem hybrid. The probe undergoes spontaneous conformational reorganization that forces the arm sequences apart, separating the fluorophore from the quencher, and permitting the fluorophore to fluoresce (Bonnet et al., 1999). The power of molecular beacons lies in their ability to hybridize only to target sequences that are perfectly complementary to the probe sequence, hence permitting detection of single base differences (Kota et al., *Plant Mol. Biol. Rep.* 17: 363-370 (1999)). Molecular beacon detection can be performed for example, on the Mx4000® Multiplex Quantitative PCR System from Stratagene (La Jolla, Calif.).

The electronic dot blot assay uses a semiconductor microchip comprised of an array of microelectrodes covered by an agarose permeation layer containing streptavidin. Biotinylated amplicons are applied to the chip and electrophoresed to selected pads by positive bias direct current, where they remain embedded through interaction with streptavidin in the permeation layer. The DNA at each pad is then hybridized to mixtures of fluorescently labeled allele-specific oligonucleotides. Single base pair mismatched probes can then be preferentially denatured by reversing the charge polarity at individual pads with increasing amperage. The array is imaged using a digital camera and the fluorescence quantified as the amperage is ramped to completion. The fluorescence intensity is then determined by averaging the pixel count values over a region of interest (Gilles et al., *Nature Biotech.* 17: 365-370 (1999)).

A more recent application based on recognition of heteroduplex DNA molecules uses denaturing high-performance liquid chromatography (DHPLC). This technique represents a highly sensitive and fully automated assay that incorporates a Peltier-cooled 96-well autosampler for high-throughput SNP analysis. It is based on an ion-pair reversed-phase high performance liquid chromatography method. The heart of the assay is a polystyrene-divinylbenzene copolymer, which functions as a stationary phase. The mobile phase is composed of an ion-pairing agent, triethylammonium acetate (TEAA) buffer, which mediates the binding of DNA to the stationary phase, and an organic agent, acetonitrile (ACN), to achieve subsequent separation of the DNA from the column. A linear gradient of CAN allows the separation of fragments based on the presence of heteroduplexes. DHPLC thus identifies mutations and polymorphisms that cause heteroduplex formation between mismatched nucleotides in double-stranded PCR-amplified DNA. In a typical assay, sequence variation creates a mixed population of heteroduplexes and homoduplexes during reannealing of wild-type and mutant DNA. When this mixed population is analyzed by DHPLC under partially denaturing temperatures, the heteroduplex molecules elute from the column prior to the homoduplex molecules, because of their reduced melting temperatures (Kota et al., *Genome* 44: 523-528 (2001)). An example of an instrument used to analyze SNPs by DHPLC is the WAVE® HS System from Transgenomic, Inc. (Omaha, Nebr.).

A microarray-based method for high-throughput monitoring of plant gene expression can be utilized as a genetic marker system. This 'chip'-based approach involves using microarrays of nucleic acid molecules as gene-specific hybridization targets to quantitatively or qualitatively measure expression of plant genes (Schena et al., *Science* 270: 467-470 (1995), the entirety of which is herein incorporated by reference; Shalon, Ph.D. Thesis. Stanford University (1996), the entirety of which is herein incorporated by reference). Every nucleotide in a large sequence can be queried at the same time. Hybridization can be used to efficiently analyze nucleotide sequences. Such microarrays can be probed with any combination of nucleic acid molecules. Particularly preferred combinations of nucleic acid molecules to be used as probes include a population of mRNA molecules from a known tissue type or a known developmental stage or a plant subject to a known stress (environmental or man-made) or any combination thereof (e.g. mRNA made from water stressed leaves at the 2 leaf stage). Expression profiles generated by this method can be utilized as markers.

For the purpose of QTL mapping, the markers included must be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander and Botstein, *Genetics,* 121:185-199 (1989), and the interval mapping, based on maximum likelihood methods described by Lander and Botstein, *Genetics,* 121:185-199 (1989), and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, *Genetics,* 121:185-199 (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, *Genetics,* 139:1421-1428 (1995), the entirety of which is herein incorporated by reference). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, *Genetics,* 136:1447-1455 (1994) and Zeng, *Genetics,* 136:1457-1468 (1994). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, *Genetics,* 136:1457-1468 (1994)). These models can be extended to multi-environment experiments to analyze genotype-environment interactions (Jansen et al., *Theo. Appl. Genet.* 91:33-37 (1995).

Selection of appropriate mapping populations is important to map construction. The choice of an appropriate mapping population depends on the type of marker systems employed (Tanksley et al., *Molecular mapping of plant chromosomes. chromosome structure and function: Impact of new concepts* J. P. Gustafson and R. Appels (eds.). Plenum Press, New York, pp. 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted x exotic) and generally yield greatly reduced linkage distances. Wide crosses will usually provide segregating populations with a relatively large array of polymorphisms when compared to progeny in a narrow cross (adapted x adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938), the entirety of which is herein incorporated by reference). In the case of dominant markers, progeny tests (e.g $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*) 89:1477-1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore, et al., *Proc. Natl. Acad. Sci.* (*U.S.A.*) 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

An alternative to traditional QTL mapping involves achieving higher resolution by mapping haplotypes, versus individual markers (Fan et al. 2006 Genetics). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

The SNP markers of the present invention can be used to isolate or substantially purify an allele of a QTL that is also located on linkage group associated with ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13. Construction of an overlapping series of clones (a clone contig) across the region can provide the basis for a physical map encompassing an allele of a fungal disease resistance QTL that are located on a linkage group associated with ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13. The yeast artificial chromosome (YAC) cloning system has facilitated chromosome walking and large-size cloning strategies. A sequence tag site (STS) content approach utilizing the markers of the present invention can be used for the construction of YAC clones across chromosome regions. Such an STS content approach to the construction of YAC maps can provide a detailed and ordered STS-based map of any chromosome region, including the region encompassing the allele of a QTL is also located on a linkage group associated with ASR resistance locus 1, ASR resistance locus 2, ASR resistance locus 3, ASR resistance locus 4, ASR resistance locus 5, ASR resistance locus 6, ASR resistance locus 7, ASR resistance locus 8, ASR resistance locus 9, ASR resistance locus 10, ASR resistance locus 11, ASR resistance locus 12, and ASR resistance locus 13. YAC maps can be supplemented by detailed physical maps are constructed across the region by using BAC, PAC, or bacteriophage P1 clones that contain inserts ranging in size from 70 kb to several hundred kilobases (Cregan, *Theor. Appl. Gen.* 78:919-928 (1999), Sternberg, *Proc. Natl. Acad. Sci.* 87:103-107 (1990), Sternberg, *Trends Genet.* 8:11-16 (1992); Sternberg et al., *New Biol.* 2:151-162 (1990); Ioannou et al., *Nat. Genet.* 6:84-89 (1994); Shizuya et al., *Proc. Natl. Acad. Sci.* 89:8794-8797 (1992), all of which are herein incorporated by reference in their entirety).

Overlapping sets of clones are derived by using the available markers of the present invention to screen BAC, PAC, bacteriophage P1, or cosmid libraries. In addition, hybridization approaches can be used to convert the YAC maps into BAC, PAC, bacteriophage P1, or cosmid contig maps. Entire YACs and products of inter-Alu-PCR as well as primer sequences from appropriate STSs can be used to screen BAC, PAC, bacteriophage P1, or cosmid libraries. The clones isolated for any region can be assembled into contigs using STS content information and fingerprinting approaches (Sulston et al., *Comput. Appl. Biosci.* 4:125-132 (1988)).

The degeneracy of the genetic code, which allows different nucleic acid sequences to code for the same protein or peptide, is known in the literature. As used herein a nucleic acid molecule is degenerate of another nucleic acid molecule when the nucleic acid molecules encode for the same amino acid sequences but comprise different nucleotide sequences. An aspect of the present invention is that the nucleic acid molecules of the present invention include nucleic acid molecules that are degenerate of the nucleic acid molecule that encodes the protein(s) of the quantitative trait alleles.

Another aspect of the present invention is that the nucleic acid molecules of the present invention include nucleic acid molecules that are homologues of the nucleic acid molecule that encodes the one or more of the proteins associated with the QTL.

Exogenous genetic material may be transferred into a plant by the use of a DNA plant transformation vector or construct designed for such a purpose. A particularly preferred subgroup of exogenous material comprises a nucleic acid molecule of the present invention. Design of such a vector is generally within the skill of the art (See, Plant Molecular Biology: A Laboratory Manual, eds. Clark, Springer, New York (1997), Examples of such plants, include, without limitation, alfalfa, *Arabidopsis*, barley, *Brassica*, broccoli, cabbage, citrus, cotton, garlic, oat, oilseed rape, onion, canola, flax, maize, an ornamental plant, pea, peanut, pepper, potato, rice, rye, sorghum, soybean, strawberry, sugarcane, sugarbeet, tomato, wheat, poplar, pine, fir, eucalyptus, apple, lettuce, lentils, grape, banana, tea, turf grasses, sunflower, oil palm, *Phaseolus* etc.

A construct or vector may include the endogenous promoter of the fungal disease resistance QTL of the present invention. The characteristic of fungal disease resistance might best be achieved by expressing the identified QTL protein with the endogenous promoter. Alternatively, a heterologous promoter may be selected to express the protein or protein fragment of choice. These promoters may be operably linked to a polynucleotide sequence encoding the protein corresponding to the fungal resistance QTL. The heterologous promoter may be one that is selected based upon maturation or flowering time, in that timing of expression of the desired protein may be critical to the parameters affecting the fungal disease resistance trait. Effective expression of the fungal disease resistance QTL may require promoters that express in specific tissue types as well.

Alternatively, the promoters may be operably linked to other nucleic acid sequences, such as those encoding transit peptides, selectable marker proteins, or antisense sequences. The promoters may be selected on the basis of the cell type into which the vector will be inserted or on the basis of its regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (Poszkowski, et al., *EMBO J.*, 3: 2719, 1989; Odell, et al., *Nature*, 313:810, 1985; Chau et al., *Science*, 244:174-181. 1989). Often-used constitutive promoters include the CaMV 35S promoter (Odell, et al., *Nature*, 313: 810, 1985), the enhanced CaMV 35S promoter, the Figwort Mosaic Virus (FMV) promoter (Richins, et al., *Nucleic Acids Res.* 20: 8451, 1987), the nopaline synthase (nos) promoter (Shaw et al., *Nucleic Acids Res.* 12: 7831-7846 (1984)) and the octopine synthase (ocs) promoter.

Useful inducible promoters include promoters induced by salicylic acid or polyacrylic acids (PR-1; Williams, et al., *Biotechnology* 10:540-543, 1992), induced by application of safeners (substituted benzenesulfonamide herbicides; Hershey and Stoner, *Plant Mol. Biol.* 17: 679-690, 1991), heat-shock promoters (Ou-Lee et al., *Proc. Natl. Acad Sci U.S.A.* 83: 6815, 1986; Ainley et al., *Plant Mol. Biol.* 14: 949, 1990), a nitrate-inducible promoter derived from the spinach nitrite reductase transcribable polynucleotide sequence (Back et al., *Plant Mol. Biol.* 17: 9, 1991), hormone-inducible promoters (Yamaguchi-Shinozaki et al., *Plant Mol. Biol.* 15: 905, 1990), and light-inducible promoters associated with the small subunit of RuBP carboxylase and LHCP families (Kuhlemeier et al., *Plant Cell* 1: 471, 1989; Feinbaum et al., *Mol. Gen. Genet.* 226: 449-456, 1991; Weisshaar, et al., *EMBO J.* 10: 1777-1786, 1991; Lam and Chua, *J. Biol. Chem.* 266: 17131-17135, 1990; Castresana et al., *EMBO J.* 7: 1929-1936, 1988; Schulze-Lefert, et al., *EMBO J.* 8: 651, 1989).

Particularly preferred promoters in the recombinant vector include the nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987); the light-inducible promoter from the small subunit of ribulose-1,5-bisphosphate carboxylase (ssRUBISCO); the EIF-4A promoter from tobacco (Mandel, et al., *Plant Mol. Biol,* 29: 995-1004, 1995); the chitinase promoter from *Arabidopsis* (Samac, et al., *Plant Cell,* 3:1063-1072, 1991); the LTP (Lipid Transfer Protein) promoters from broccoli (Pyee, et al., *Plant J.,* 7: 49-59, 1995); petunia chalcone isomerase (Van Tunen, et al., *EMBO J.* 7: 1257, 1988); bean *glycine* rich protein 1 (Keller, et al., *EMBO L.,* 8: 1309-1314, 1989); the Potato patatin (Wenzler, et al., *Plant Mol. Biol.,* 12: 41-50, 1989); the *Arabidopsis* Actin 7 promoter (GENBANK accession U27811.1 GI:1002528, 17-Apr.-1997 and PCT application: WO0144457A2; the entirety of which is herein incorporated by reference); the *Arabidopsis* Actin 8 promoter (An et al., *Plant J.* 10: 107-121 (1996) and PCT application: WO0144457A2); the *Arabidopsis* Rubisco small subunit 4 promoter (Krebbers et al., *Plant Mol. Biol.* 11: 745-759 (1988)); the *Brassica* napin gene promoter (U.S. Pat. No. 5,420,034, the entirety of which is herein incorporated by reference); the *Arabidopsis* Suc2 promoter (Truernit et al., *Planta* 196: 564-570 (1995)); *Arabidopsis* elongation factor EF-1 alpha promoter (Axelos et al., *Mol. Gen. Genet.* 219: 106-112 (1989)); and the *Glycine max* 7sα beta conglycin promoter, Sphas (Doyle et al., *J. Biol. Chem.* 261: 9228-9238 (1986)).

Constructs of the present invention may also include additional 5' untranslated regions (5' UTR) or leaders of an mRNA polynucleotide molecule or gene which can play an important role in translation initiation. Some 5' UTRs may act as translational enhancers and may also be incorporated as part of the recombinant vector. For example, non-translated 5' leader polynucleotide molecules derived from heat shock protein genes have been demonstrated to enhance gene expression in plants (see for example, U.S. Pat. No. 5,659,122, the entirety of which is herein incorporated by reference and U.S. Pat. No. 5,362,865, the entirety of which is herein incorporated by reference). Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include the *Arabidopsis* Actin 7 leader (GENBANK accession U27811.1 GI:1002528, 17-Apr.-1997 and PCT application: WO0144457A2; the entirety of which is herein incorporated by reference); the *Arabidopsis* Actin 8 leader (An et al., *Plant J.* 10: 107-121 (1996) and PCT application: WO0144457A2); the *Arabidopsis* Rubisco small subunit 4 leader (Krebbers et al., *Plant Mol. Biol.* 11: 745-759 (1988)); the *Brassica* napin gene leader (U.S. Pat. No. 5,420,034, the entirety of which is herein incorporated by reference); the *Arabidopsis* Suc2 leader (Truernit et al., *Planta* 196: 564-570 (1995)); the *Petunia hybrida* Hsp70 gene leader (Winter et al., *Mol. Gen. Genet.* 211: 315-319 (1988)): the *Arabidopsis* EPSPS gene leader (Klee et al., *Mol. Gen. Genet.* 210: 437-442 (1987)); the *Arabidopsis* elongation factor EF-1 alpha leader (Axelos et al., *Mol. Gen. Genet.* 219: 106-112 (1989); and the *Glycine max* 7sα beta conglycin leader (Doyle et al., *J. Biol. Chem.* 261: 9228-9238 (1986)). These additional upstream regulatory polynucleotide molecules may be derived from a source that is native or heterologous with respect to the other elements present on the construct.

In addition, constructs may include additional regulatory polynucleotide molecules from the 3'-untranslated region (3' UTR) of plant genes. A 3' UTR or terminator typically provides a transcriptional termination signal, and a polyadenylation signal which functions in plants to cause the addition of adenylate nucleotides to the 3' end of the mRNA. Usually, nucleic acid sequences located a few hundred base pairs downstream of the polyadenylation site serve to terminate transcription. In addition, some 3' UTRs provide additional properties such as enhancing the stability of the mRNA as in the potato proteinase inhibitor II gene 3' UTR (An et al., *The Plant Cell* 1: 115-122 (1989)). Other 3' UTRs may provide sequences that enhance degredation of the mRNA such as the 5'-UUAUUUAUU-3' motif shown to contribute to lower stability of RNA messages in animal cells (Zubiaga et al., *Mol. Cell. Biol.* 15: 2219-2230 (1995)). These additional downstream regulatory polynucleotide molecules may be derived from a source that is native or heterologous with respect to the other elements present on the construct.

Preferred 3' UTRs or terminators are the potato proteinase inhibitor II gene 3' UTR (An et al., *The Plant Cell* 1: 115-122 (1989)); the pea Rubisco small subunit E9 terminator (Coruzzi et al., *EMBO J.* 3: 1671-1679 (1984)); the cauliflower mosaic virus 35S terminator; the *Brassica* napin gene terminator (U.S. Pat. No. 5,420,034); the *Glycine max* 7sα beta conglycin gene terminator (Doyle et al., *J. Biol. Chem.* 261: 9228-9238 (1986)); the Phaseoulus vulgaris Arc5 terminator (Goossens et al., *Eur. J. Biochem.* 225: 787-795 (1994)); the *Agrobacterium tumefaciens* nopaline synthase terminator (Rojiyaa et al., 1987, GENBANK Accession E01312 and U.S. Patent Application US20020192813A1, the entirety of which is herein incorporated by reference); and the *Glycine max* ADR12 gene terminator (Datta et al., *Plant Mol. Biol.* 21: 859-869 (1993)).

A vector or construct may also include regulatory elements derived from the introns of certain genes. Examples of such include the Adh intron 1 (Callis et al., *Genes and Develop.* 1:1183-1200 (1987); the sucrose synthase intron (Vasil et al., *Plant Physiol.* 91:1575-1579 (1989); and the TMV omega element (Gallie et al., *The Plant Cell* 1:301-311 (1989)). Preferred introns are the *Arabidopsis* Actin 7 intron (GENBANK accession U27811.1 GI:1002528, 17-Apr.-1997 and PCT application: WO200144457A2; the entirety of which is herein incorporated by reference); the *Arabidopsis* Actin 8 intron (An et al., *Plant J.* 10: 107-121 (1996) and PCT application: WO200144457A2); and the *Arabidopsis* elongation factor EF-1 alpha inton (Axelos et al., *Mol. Gen. Genet.* 219: 106-112 (1989)) These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985)), which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988)), which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (for example, U.S. Pat. No. 6,222,100, the entirety of which is herein incorporated by reference); a methotrexate resistant DHFR gene (Thillet et al., *J. Biol. Chem.* 263:12500-12508 (1988)); Dicamba tolerance conferred, for example, by a gene for dicamba monooxygenase (DMO) from *Pseudomonas maltophilia* (US Patent Application 20030135879, the entirety of which is herein incorporated by reference).

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987), the entirety of which is herein incorporated by reference; Jefferson et al., *EMBO J.* 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., *Proc. Natl. Acad. Sci.* (*U.S.A.*) 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856-859 (1986), the entirety of which is herein incorporated by reference); a xylE gene (Zukowsky et al., *Proc. Natl. Acad. Sci.* (*U.S.A.*) 80:1101-1105 (1983), the entirety of which is herein incorporated by reference) which encodes a catechol dioxygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; and an α-galactosidase.

Any of the techniques known in the art for introduction of transgenes into plants may be used to prepare a plant resistant to fungal disease in accordance with the invention. Suitable methods for transformation of plants are believed to include virtually any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824, 877; 5,591,616; 5,981,840; and 6,384,301; and protoplast transformation as illustrated in U.S. Pat. No. 5,508,184. Through the application of techniques such as these, the cells of virtually any plant species may be stably transformed, and these cells developed into transgenic plants. Techniques useful in the context of cotton transformation are disclosed in U.S. Pat. Nos. 5,846,797, 5,159,135, 5,004,863, and 6,624, 344; and techniques for transforming *Brassica* plants in particular are disclosed, for example, in U.S. Pat. No. 5,750,871; and techniques for transforming soybean are disclosed in for example in Zhang et al. (*Plant Cell Tissue Organ Cult* 56:37-46 (1999) and U.S. Pat. No. 6,384,301.

Having now generally described the invention, the same will be more readily understood through reference to the following examples which are provided by way of illustration, and are not intended to be limiting of the present invention, unless specified.

EXAMPLES

Example 1

Breeding of Near-Isogenic Lines Containing ASR Resistance Loci

One thousand, four hundred single nucleotide polymorphism (SNP) markers, randomly distributed across the 20 linkage groups of the soybean genetic linkage map, were used to identify SNP markers tightly linked to the ASR resistance locus 1 locus. A panel of soybean lines consisting of near-isogenic lines (NILs) developed from a cross between Williams 82 and ASR resistance locus 1 donor, PI 200492. Derivative lines of PI 200492 were used to identify SNP markers that were polymorphic between Williams 82 and PI 200492. These polymorphic SNP markers were then used to identify the map location of ASR resistance locus 1 using a segregating backcross population, L85-2378. L85-2378 was developed by crossing Williams 82 with PI 200492 and five backcross cycles, or essentially 6 doses of Williams 82, were made to recover most of Williams 82's desirable traits. Thus L85-2378 is created consisting of individuals nearly like the recurrent parent, Williams 82, but each individual NIL carries varying amounts or mosaic of genomic regions from the donor parent, PI 200492.

The entire population was genotyped with the polymorphic SNP markers identified above and was subsequently evaluated for soybean rust resistance using a greenhouse assay. Associations between SNP marker genotype and soybean rust resistance phenotype were evaluated. SNP markers found to be in high linkage disequilibria with ASR resistance locus 1 disease phenotypic response were NS0093250, NS0119710, NS0103004, NS0099454, NS0102630, NS0102915, NS0102913, NS0123728, NS0129943, NS0102168, NS0092723, NS0098177, NS0127343, and NS0101121, and are presented in Table 1 and indicated as SEQ ID NOs: 67 through 80. All of these SNP markers map to a region on linkage group G of the public soybean genetic linkage map. Table 1 lists sequences for PCR amplification primers, indicated as SEQ ID NOs: 1 through 28, and probes, indicated as SEQ ID NOs: 100 through 127, corresponding to these SNP markers. Two SNP markers were identified as being useful in monitoring the positive introgression of ASR resistance locus 1 and correspond to SNP markers NSO102913 and NSO129943 and correspond to SEQ ID NO: 73 and SEQ ID NO: 75, respectively.

The efficacy of ASR resistance locus 1 against soybean rust isolates from Alabama was also evaluated in the following F2:3 populations: AG4403×PI 200492, AG3302×PI 200492, AG3201×PI 200492, AG26932×PI 200492, AG2402×PI 200492. In each of the populations, a 3:1 segregation ratio was observed indicating a single dominant gene inheritance pattern.

Following the procedure described for ASR resistance locus 1, the ASR resistance locus 3 locus was mapped using NILs developed from the cross between Williams 82 and the donor parent, PI 462312, followed by five backcross cycles, or essentially 6 doses of Williams 82, were made to recover most of Williams 82's desirable traits. Thus L85-2378 is created consisting of individuals nearly like the recurrent parent, Williams 82 but each individual near isogenic line carries varying amounts or mosaic of genomic regions from the donor parent, PI 200492. The entire population was genotyped with the set of polymorphic SNP markers identified above and was subsequently evaluated for soybean rust resistance using a greenhouse assay. Associations between SNP marker genotype and soybean rust resistance phenotype were evaluated. SNP markers found to be in high linkage disequilibria with ASR resistance locus 3 were NS0099746, NS0123747, NS0126598, NS0128378, NS0096829, NS0125408, NS0098902, NS0099529, NS0097798, NS0137477, NS0095322, NS0136101, and NS0098992, and are presented in Table 1 and indicated as SEQ ID NOs: 81 through 93. These markers were all mapping to LG C2 of the public soybean genetic map. Table 1 lists sequences for PCR amplification primers, indicated as SEQ ID NOs: 29 through 54, and probes, indicated as SEQ ID NOs: 128 through 153, corresponding to these SNP markers. The marker used to monitor the introgression of ASR resistance locus 3 corresponds to SNP marker NSO137477 and is indicated as SEQ ID NO: 90. To confirm the putative location of ASR resistance locus 3, a segregating F3:4 population was developed between AVRDC-8 and AG4403. AVRDC-8 is line developed by Asian Vegetable Research and Development Center in Taiwan by crossing Ankur (ASR resistance locus 3 containing line) and PI 230970 (ASR resistance locus 2 donor). This population is currently being genotyped for SNP markers and evaluated for resistance reaction against a soybean rust isolate from Loxley, Ala. to validate the location of ASR resistance locus 3.

The approximate locations of ASR resistance locus 2 and ASR resistance locus 4 were later determined based upon a survey of polymorphisms between a panel of PI lines that are known to contain either ASR resistance locus 2 or ASR resistance locus 4, PI 230970, PI 459025B, the donor of ASR resistance locus 2 and ASR resistance locus 4, respectively, and other lines that were reported in literature to contain either QTL. Based on the polymorphism survey, any polymorphic SNP marker is a candidate region near the ASR resistance loci. For ASR resistance locus 2, two candidate regions were identified and the locus is most likely located on linkage group J, near or within the disease resistance cluster Brown Stem Rot, Soybean Cyst Nematode resistance and Frog Eye Leaf Spot, or within linkage group N. The ASR resistance locus 4 is likely located on linkage group N.

TABLE 1

SNP markers for identification and selection of ASR resistance locus 1 and ASR resistance locus 3.

| MARKER | SEQ ID | SEQ ID FORWARD PRIMER | SEQ ID REVERSE PRIMER | SEQ ID PROBE 1 | SEQ ID PROBE 2 |
|---|---|---|---|---|---|
| NS0093250 | 67 | 1 | 2 | 100 | 101 |
| NS0119710 | 68 | 3 | 4 | 102 | 103 |
| NS0103004 | 69 | 5 | 6 | 104 | 105 |
| NS0099454 | 70 | 7 | 8 | 106 | 107 |
| NS0102630 | 71 | 9 | 10 | 108 | 109 |
| NS0102915 | 72 | 11 | 12 | 110 | 111 |
| NS0102913 | 73 | 13 | 14 | 112 | 113 |
| NS0123728 | 74 | 15 | 16 | 114 | 115 |
| NS0129943 | 75 | 17 | 18 | 116 | 117 |
| NS0102168 | 76 | 19 | 20 | 118 | 119 |
| NS0092723 | 77 | 21 | 22 | 120 | 121 |
| NS0098177 | 78 | 23 | 24 | 122 | 123 |
| NS0127343 | 79 | 25 | 26 | 124 | 125 |
| NS0101121 | 80 | 27 | 28 | 126 | 127 |
| NS0099746 | 81 | 29 | 30 | 128 | 129 |
| NS0123747 | 82 | 31 | 32 | 130 | 131 |
| NS0126598 | 83 | 33 | 34 | 132 | 133 |
| NS0128378 | 84 | 35 | 36 | 134 | 135 |
| NS0096829 | 85 | 37 | 38 | 136 | 137 |
| NS0125408 | 86 | 39 | 40 | 138 | 139 |
| NS0098902 | 87 | 41 | 42 | 140 | 141 |
| NS0099529 | 88 | 43 | 44 | 142 | 143 |
| NS0097798 | 89 | 45 | 46 | 144 | 145 |
| NS0137477 | 90 | 47 | 48 | 146 | 147 |
| NS0095322 | 91 | 49 | 50 | 148 | 149 |
| NS0136101 | 92 | 51 | 52 | 150 | 151 |
| NS0098982 | 93 | 53 | 54 | 152 | 153 |

Example 2

Collection and Propagation of Spores

Asian Soybean Rust urediniospores from *Phakopsora pachyrhizi* were collected from infected plants at the Monsanto Loxley Agronomy station (Loxley, Ala.), herein referred to as the Loxley strain.

Soybean plants were inoculated by spraying the underside of the leaves with spores suspended in water containing 0.01% Tween-20. Lesion development was visible without magnification at around 7 to 10 days with sporulation occurring at 12 to 14 days after infection. Spores from the infected plants were collected and resuspended in sterile deionized water containing 0.01% Tween 20. The spore concentration was determined using a hemacytometer.

Example 3

Detached Leaf Assay for Asian Soybean Rust Resistance

Two types of leaf tissue were assessed for ASR disease phenotyping. Unifoliates leaves, seven to ten days after emergence, or V3 trifoliate leaves, twenty-one to twenty-eight after emergence, were assessed. At about two days after emergence from the soil, the soybean plant bears a pair of unifoliate leaves which are fully unfurled about five days later and constitute the first 'true leaves'. At about seven days after emergence, the trifoliate leaves appear (comprising three leaves at the end of one petiole). Three sets emerge in sequence and the first trifoliate leaves are denoted as the V1 stage, and are fully expanded at ten days after emergence. The next two V stages occur a week apart. Notably, the leaves are inoculated for disease after they have both unfurled and hardened, i.e. not new and green. The unifoliates tend to harden very quickly, around 8-10d after emergence, while V2 and V3 trifoliates may not even unfurl completely until up to 24-28 days after emergence.

Three 3.2 cm diameter Watmann #1 filter papers are placed in each of 6 wells of a 6-well tissue culture plate (well volume is 15.5 milliliters). The leaves are cut into 3 centimeter by 3 centimeter pieces and placed on top of the Watmann filter papers with the bottom (stomatal side) of the leaf facing upwards. Approximately 2.0 milliliters of sterile deionized water is put into each well of the 6-well tissue culture plate. Asian Soybean Rust urediniospores from *Phakopsora pachyrhizi* are suspended in sterile deionized water containing 0.01% tween 20 at a concentration of $1 \times 10^5$ urediniospores per milliliter. Approximately 50 microliters of spore suspension is applied to each leaf piece using an airbrush (Model Badger 155 Anthem, Badger AirBrush Co., Franklin Park, Ill.) with a compressor (Model TC-20, Airbrush Depot, San Diego, Calif.) setting of 1 kilogram per square centimeter to wetness. The 6-well plate is then sealed with parafilm and placed in a growth chamber set to 22 degrees Celsius, with a photoperiod of 12 hours daylength. The plates are checked every 2 or 3 days to monitor the progression of disease and to assure the wells have not dried out. Deionized water is added to make up the original volume in the well when needed or incubator relative humidity is adjusted to approximately 80%. Early symptoms of developing lesions should be evident under a dissecting microscope about 3 to 5 days after inoculation. Sporulating lesions should be evident 9 to 14 days after inoculation. Average soybean rust severity scores are calculated from multiple trials. The rust severity score uses a rating scale from 1 to 5; 1—being immune, 2—demonstrating red/brown lesions over less than 50% of the leaf area, 3—demonstrating red/brown lesions over greater than 50% of the leaf area, 4—demonstrating tan lesions over less than 50% of the leaf area and 5—demonstrating tan lesions over greater than 50% of the leaf area. Leaf sections can remain viable in this assay for up to 2 months.

Experiments using Asian Soybean Rust susceptible soybean, Lee 74 demonstrate consistently high levels of infection for each assay performed. Further experiments evaluating putative resistant germplasm were able to differentiate tolerant from susceptible accessions as demonstrated in Table 2. Accession PI 200487 demonstrated a slow rust resistance phenotype. Efforts are underway to identify markers that will be used in the introgression of the resistance locus identified in PI 200487 into elite germplasm.

In addition, comparison of ASR evaluation of unifoliate and trifoliate leaf tissue showed it takes approximately 45 days from seed to data point for trifoliates and approximately 23 days for unifoliates. By cutting the assay time in half, this significantly economizes the detached leaf assay and time required to determine disease resistance rating. By saving 3 weeks, plants can be propagated on a faster time scale and susceptible plants can be culled sooner, saving field and greenhouse space.

TABLE 2

Average rust score for resistant and susceptible accessions as determined using unifoliate and trifoliate leaf tissue; "—" indicates the assay was not performed.

| Accession | Average Rust Severity Score Detached Unifoliate | Average Rust Severity Score Detached Leaf |
|---|---|---|
| Lee 74 | 5.0 | 5 |
| PI 200487 | 1.89 | 2.25 |
| PI 200492 (ASR resistance locus 1) | 1.00 | 2 |
| PI 200499 | — | 5 |
| PI 230970 | 2.5 | 3 |
| PI 368038 | — | 3 |
| PI 368039 | — | 2 |
| PI 462312 | — | 2 |
| PI 547875 | — | 2 |
| PI 547878 | — | 4.25 |
| PI 547879 | — | 5 |
| Tiana | — | 5 |
| Williams | — | 5 |
| AVRDC-8 | 1.8 | 2.25 |
| Dowling | — | 5 |

Example 4

Testing of Elite Crosses for Resistance to *P. Pachyrizi* with Introgressed ASR Resistance Locus 1, ASR Resistance Locus 2 and ASR Resistance Locus 3

Crosses with donor resistant parent line, PI 200492, containing ASR resistance locus 1 were performed with various elite lines of soybean to monitor the positive introgression of ASR resistance locus 1. Leaf assays for resistance to the Loxley strain were performed using lines derived from crosses with the resistant parent line accession, PI 200492 (ASR resistance locus 1) as well as known resistant accessions (PI 230970 (ASR resistance locus 2) and PI 462312 (ASR resistance locus 3)) and susceptible elite lines. The resistance scores for all lines tested are presented in Table 3. Average rust severity scores were derived from 4 plants, each with 4 replications and rated on 4 different days (10DAI, 17DAI, 24DAI, 32DAI).

TABLE 3

Average Rust Severity Score of ASR backcross events and elite lines.

| Cross | Progeny From Cross | ASR resistance locus Loci | Average Rust Severity Score |
|---|---|---|---|
| Multiple crosses to introgress both ASR resistance locus 2 and ASR resistance locus 3 | AVRDC-8 | ASR resistance locus 2/ASR resistance locus 3 | 1.7 |
| Known Susceptible Line | Dowling | Susceptible | 5 |
| GL_AG4801//L85-2378/L86-1752 | JN1137.1 | ASR resistance locus 1 (MAS) | 1 |
| GL_AG4801//L85-2378/L86-1753 | JN1137.2 | ASR resistance locus 1 (MAS) | 5 |
| GL_AG4801//L85-2378/L86-1754 | JN1137.3 | ASR resistance locus 1 (MAS) | 1 |
| GL_AG4801//L85-2378/L86-1755 | JN1137.4 | ASR resistance locus 1 (MAS) | 1 |
| GL_AG4801//L85-2378/L86-1752 | JN1153.1 | ASR resistance locus 1 (MAS) | 1 |
| GL_AG4801//L85-2378/L86-1753 | JN1153.2 | ASR resistance locus 1 (MAS) | 1 |
| GL_AG4801//L85-2378/L86-1754 | JN1153.3 | ASR resistance locus 1 (MAS) | 1 |
| GL_AG4801//L85-2378/L86-1755 | JN1153.4 | ASR resistance locus 1 (MAS) | 1 |
| GL_AG4801//L85-2378/L86-1752 | JN1160.1 | ASR resistance locus 1 (MAS) | 4.8 |
| GL_AG4801//L85-2378/L86-1752 | JN1160.2 | ASR resistance locus 1 (MAS) | 1 |
| GL_AG4801//L85-2378/L86-1752 | JN1160.3 | ASR resistance locus 1 (MAS) | 1 |
| GL_AG4801//L85-2378/L86-1752 | JN1160.4 | ASR resistance locus 1 (MAS) | 1 |
| GL_AG4801//L85-2378/L86-1752 | JN1163.1 | ASR resistance locus 1 (MAS) | 1 |
| GL_AG4801//L85-2378/L86-1752 | JN1163.2 | ASR resistance locus 1 (MAS) | 4.8 |
| GL_AG4801//L85-2378/L86-1752 | JN1163.3 | ASR resistance locus 1 (MAS) | 1 |
| GL_AG4801//L85-2378/L86-1752 | JN1163.4 | ASR resistance locus 1 (MAS) | 5 |
| GL_AG5501//L85-2378/L86-1752 | JN1691.1 | ASR resistance locus 1 (MAS) | 4.5 |
| GL_AG5501//L85-2378/L86-1752 | JN1691.2 | ASR resistance locus 1 (MAS) | 4.6 |
| GL_AG5501//L85-2378/L86-1752 | JN1691.3 | ASR resistance locus 1 (MAS) | 4.6 |
| GL_AG5501//L85-2378/L86-1752 | JN1691.4 | ASR resistance locus 1 (MAS) | 3 |
| GL_AG5501//L85-2378/L86-1752 | JN1692.1 | ASR resistance locus 1 (MAS) | 1.1 |
| GL_AG5501//L85-2378/L86-1752 | JN1692.2 | ASR resistance locus 1 (MAS) | 1 |
| GL_AG5501//L85-2378/L86-1752 | JN1692.3 | ASR resistance locus 1 (MAS) | 1 |
| GL_AG5501//L85-2378/L86-1752 | JN1692.4 | ASR resistance locus 1 (MAS) | 1 |
| GL_AG5501//L85-2378/L86-1752 | JN1742.1 | ASR resistance locus 1 (MAS) | 1 |
| GL_AG5501//L85-2378/L86-1752 | JN1742.2 | ASR resistance locus 1 (MAS) | 1 |
| GL_AG5501//L85-2378/L86-1752 | JN1742.3 | ASR resistance locus 1 (MAS) | 1 |
| GL_AG5501//L85-2378/L86-1752 | JN1742.4 | ASR resistance locus 1 (MAS) | 1 |
| GL_AG5501//L85-2378/L86-1752 | JN1765.1 | ASR resistance locus 1 (MAS) | 1.2 |
| GL_AG5501//L85-2378/L86-1752 | JN1765.2 | ASR resistance locus 1 (MAS) | 1 |
| GL_AG5501//L85-2378/L86-1752 | JN1765.3 | ASR resistance locus 1 (MAS) | 1 |
| GL_AG5501//L85-2378/L86-1752 | JN1765.4 | ASR resistance locus 1 (MAS) | 1 |
| GL_AG5501//L85-2378/L86-1752 | JN1774.1 | ASR resistance locus 1 (MAS) | 1 |
| GL_AG5501//L85-2378/L86-1752 | JN1774.2 | ASR resistance locus 1 (MAS) | 1 |
| GL_AG5501//L85-2378/L86-1752 | JN1774.3 | ASR resistance locus 1 (MAS) | 1 |
| GL_AG5501//L85-2378/L86-1752 | JN1774.4 | ASR resistance locus 1 (MAS) | 1 |
| GL_CGL4504D0C//L85-2378/L86-1752 | JN1866.1 | ASR resistance locus 1 (MAS) | 1 |
| GL_CGL4504D0C//L85-2378/L86-1752 | JN1866.2 | ASR resistance locus 1 (MAS) | 1 |
| GL_CGL4504D0C//L85-2378/L86-1752 | JN1866.3 | ASR resistance locus 1 (MAS) | 1 |

TABLE 3-continued Average Rust Severity Score of ASR backcross events and elite lines.

| Cross | Progeny From Cross | ASR resistance locus Loci | Average Rust Severity Score |
|---|---|---|---|
| GL__CGL4504D0C//L85-2378/L86-1752 | JN1866.4 | ASR resistance locus 1 (MAS) | 1 |
| GL__CGL5400E1X//L85-2378/L86-1752 | JN2242.1 | ASR resistance locus 1 (MAS) | 1 |
| GL__CGL5400E1X//L85-2378/L86-1752 | JN2242.2 | ASR resistance locus 1 (MAS) | 1 |
| GL__CGL5400E1X//L85-2378/L86-1752 | JN2242.3 | ASR resistance locus 1 (MAS) | 1 |
| GL__CGL5400E1X//L85-2378/L86-1752 | JN2242.4 | ASR resistance locus 1 (MAS) | 1 |
| GL__CGL5400E1X//L85-2378/L86-1752 | JN2243.1 | ASR resistance locus 1 (MAS) | 1 |
| GL__CGL5400E1X//L85-2378/L86-1752 | JN2243.2 | ASR resistance locus 1 (MAS) | 2.4 |
| GL__CGL5400E1X//L85-2378/L86-1752 | JN2243.3 | ASR resistance locus 1 (MAS) | 1 |
| GL__CGL5400E1X//L85-2378/L86-1752 | JN2243.4 | ASR resistance locus 1 (MAS) | 1.3 |
| GL__CGL5400E1X//L85-2378/L86-1752 | JN2250.1 | ASR resistance locus 1 (MAS) | 1 |
| GL__CGL5400E1X//L85-2378/L86-1752 | JN2250.2 | ASR resistance locus 1 (MAS) | 1 |
| GL__CGL5400E1X//L85-2378/L86-1752 | JN2250.3 | ASR resistance locus 1 (MAS) | 1.2 |
| GL__CGL5400E1X//L85-2378/L86-1752 | JN2250.4 | ASR resistance locus 1 (MAS) | 1 |
| GL__AG4403//L85-2378/L86-1752 | JN774.1 | ASR resistance locus 1 (MAS) | 1 |
| GL__AG4403//L85-2378/L86-1752 | JN774.2 | ASR resistance locus 1 (MAS) | 1.1 |
| GL__AG4403//L85-2378/L86-1752 | JN774.3 | ASR resistance locus 1 (MAS) | 1 |
| GL__AG4403//L85-2378/L86-1752 | JN774.4 | ASR resistance locus 1 (MAS) | 1 |

Lines containing the ASR resistance locus 1 locus showed greatest resistance to the Loxley strain. Introgression of the ASR resistance locus 1 was confirmed by MAS.

Example 5

Testing of Soybean Accessions for ASR Resistance Using the Detached Leaf Assay

Seven hundred putative ASR resistant accessions were identified based upon greenhouse assays, using a mixed population of ASR isolates of foreign origin. Leaf assays for resistance to ASR were performed as described in Example 3 using a subset of two hundred and fifty of the seven hundred USDA putative resistant accessions. A complementary set of two hundred and fifty ASR susceptible accessions from the USDA were selected for comparison in the leaf assay based upon matching maturities and geographic origins to the two hundred and fifty resistant accessions. The average rust severity scores of the most resistant accessions (those exhibiting an average rust severity score from 1 to 2) is presented in Table 4 below. One thousand, four hundred SNP markers, distributed every 5 centimorgans across the 20 linkage groups of the soybean genetic linkage map, will be used to identify markers useful in following the introgression of the ASR resistance loci possessed by the resistant accessions into elite germplasm.

TABLE 4

| Average Rust Severity Score ASR Resistant Accessions. | |
|---|---|
| Accession | Average Rust Severity Score |
| PI200488 | 1.0 |
| PI200492 | 1.0 |
| PI203398 | 1.0 |
| PI307884B | 1.0 |
| PI416764 | 1.0 |
| PI416826A | 1.0 |
| PI417117 | 1.0 |
| PI417132 | 1.0 |
| PI423967 | 1.0 |

TABLE 4-continued

| Average Rust Severity Score ASR Resistant Accessions. | |
|---|---|
| Accession | Average Rust Severity Score |
| PI506947 | 1.0 |
| PI507009 | 1.0 |
| PI507259 | 1.0 |
| PI561305 | 1.0 |
| PI567031B | 1.0 |
| PI567034 | 1.0 |
| PI567056A | 1.0 |
| PI567058D | 1.0 |
| PI567190 | 1.0 |
| PI605773 | 1.0 |
| PI605829 | 1.0 |
| PI605865B | 1.0 |
| PI379620 | 1.3 |
| PI416873B | 1.3 |
| PI417128 | 1.3 |
| PI417463 | 1.3 |
| PI567123A | 1.3 |
| PI578457A | 1.3 |
| PI615437 | 1.3 |
| PI379621 | 1.3 |
| PI567102B | 1.3 |
| PI594172A | 1.3 |
| PI628932 | 1.3 |
| PI079648 | 1.5 |
| PI291309C | 1.5 |
| PI416886 | 1.5 |
| PI417503 | 1.5 |
| PI506491 | 1.5 |
| PI506677 | 1.5 |
| PI506695 | 1.5 |
| PI507193 | 1.5 |
| PI567046A | 1.5 |
| PI567053 | 1.5 |
| PI567189A | 1.5 |
| PI605891B | 1.5 |
| PI200455 | 1.8 |
| PI232989 | 1.8 |
| PI594494A | 1.8 |
| PI597405D | 1.8 |
| PI069533 | 2.0 |
| PI084674 | 2.0 |
| PI230970 | 2.0 |
| PI291278 | 2.0 |

TABLE 4-continued

Average Rust Severity Score ASR Resistant Accessions.

| Accession | Average Rust Severity Score |
|---|---|
| PI341252 | 2.0 |
| PI417126 | 2.0 |
| PI417134 | 2.0 |
| PI417208 | 2.0 |
| PI423923 | 2.0 |
| PI437609A | 2.0 |
| PI471900 | 2.0 |
| PI497969 | 2.0 |
| PI506628 | 2.0 |
| PI547875 | 2.0 |
| PI567024 | 2.0 |
| PI567025A | 2.0 |
| PI578471A | 2.0 |
| PI594512C | 2.0 |
| PI594561 | 2.0 |
| PI605781A | 2.0 |
| PI605838 | 2.0 |
| PI606405 | 2.0 |
| PI606440A | 2.0 |
| PI615445 | 2.0 |

In addition, SNP markers distributed proximal and distal to ASR resistance locus 3 were genotyped for a set of eighty-nine resistant accessions. Four additional SNP markers (NS0103749, NS0118897, NS0119715, and NS0130920) were found to be associated with ASR resistance locus 3 and are listed in Table and indicated as SEQ ID NOs: 94 through 97. Table 5 lists sequences for PCR amplification primers, indicated as SEQ ID NOs: 55 through 62, and probes, indicated as SEQ ID NOs: 154 through 161, corresponding to these SNP markers.

This information will be used to identify novel resistance sources useful in prioritizing the introgression of the ASR and other pathogen resistance loci.

TABLE 5

SNP markers for identification and selection of ASR resistance locus 3.

| MARKER | SEQ ID | SEQ ID FORWARD PRIMER | SEQ ID REVERSE PRIMER | SEQ ID PROBE 1 | SEQ ID PROBE 2 |
|---|---|---|---|---|---|
| NS0103749 | 94 | 55 | 56 | 154 | 155 |
| NS0118897 | 95 | 57 | 58 | 156 | 157 |
| NS0119715 | 96 | 59 | 60 | 158 | 159 |
| NS0130920 | 97 | 61 | 62 | 160 | 161 |

Example 6

Using Association Studies to Identify QTL that Confer Fungal Disease Resistance To identify regions or genes associated with the disease is the first step toward developing resistant varieties. Four loci for rust resistance (ASR resistance locus 1, ASR resistance locus 2, ASR resistance locus 3, ASR resistance locus 4) were previously identified. In this example, linkage disequilibrium and haplotype association mapping were applied to a case-control data sample from soybean germplasm.

Four hundred ninety-two soybean lines (246 resistant-susceptible pairs) were scored for rust resistance as well as fingerprinted using 797 SNPs. Disease resistance was scored in 1 to 5 scales to a mixture of *Phakopsora pachyrhizi* isolates, with less than 3 as resistant and greater than 4 as susceptible. Specifically, case-control testing, Fishers' exact test, single marker F-test, and haplotype trend regression were explored on window sizes of 3, 5 and 9 consecutive SNPs. Multiple testing results significantly associate two SNP markers from two separate haplotype windows, referred to herein as in fungal disease resistance haplotype windows 1 and 2, on chromosome 13 24-45 cM) with resistance to fungal disease. The SNP markers NS0103033 and NS0124935 are located in fungal disease resistance haplotype windows 1 and 2 respectively. The primers for NS0103033 (SEQ ID NO: 98) are indicated in SEQ ID NOs: 63 and 64 and the probes are indicated in SEQ ID NOs: 162 and 163. The primers for NS0124935 (SEQ ID NO: 99) are indicated in SEQ ID NOs: 65 and 66 and the probes are indicated in SEQ ID NOs: 164 and 165. Resistance scores for each of the haplotypes and the marker allele for each haplotype are indicated in Table 6. Each window is designated by five SNP markers and the alleles for each is indicated as haplotype sequence. The allele for NS0103033 in haplotype window 1 and NS0124935 in haplotype window 2 are indicated in bold. For NS0103033, the SNP is actually a 9-bp indel where "Z" represents the deletion (*********) and "W" represents the insertion (GAAGTGGAT).

Varieties containing resistant haplotypes from haplotype window 1 and/or 2 are indicated in table 7. This mapping effort has identified additional ASR disease resistance QTLs in addition to the previously defined ASR resistance loci.

TABLE 6

Summary scoring for lines containing resistant haplotypes in ASR resistance haplotype windows 1 and 2. A resistance score of 0 indicates the line was resistant and a score of 1 indicates the line was designated susceptibe.

| ASR resistance locus | Haplotype Window 1 | Haplotype sequence | Resistance Score 0 | 1 |
|---|---|---|---|---|
| 5 | Haplotype 1 | AAZA? | 5 | 0 |
| 6 | Haplotype 2 | AGWGA | 26 | 10 |
| 7 | Haplotype 3 | AGWGG | 34 | 15 |
| 8 | Haplotype 4 | TAZAG | 5 | 0 |
| 9 | Haplotype 5 | TAZGA | 13 | 5 |
| ASR resistance locus | Haplotype Window 2 | Haplotype sequence | Resistance Score 0 | 1 |
| 10 | Haplotype 6 | CGTTG | 8 | 1 |
| 11 | Haplotype 7 | GGTTC | 26 | 11 |
| 12 | Haplotype 8 | GGCCC | 12 | 6 |
| 13 | Haplotype 9 | GGT-C | 4 | 0 |

TABLE 6

Disease ratings for resistant germplasm containing haplotypes in ASR resistance windows 1 and/or 2 on chromosome 13.

| Line | Rating | Resistance haplotype from haplotype window 1 | Resistance haplotype from haplotype window 2 |
|---|---|---|---|
| PI164885 | 2.5 | X | X |
| PI165524 | 2 | X | X |
| PI166028 | 2 |  | X |
| PI189968 | 2 | X | X |
| PI200446 | 2 | X |  |
| PI200488 | 2.5 |  | X |
| PI205901B | 2.5 | X |  |
| PI222549 | 2.5 | X |  |
| PI224270 | 2.5 | X |  |
| PI227331 | 2.5 | X | X |
| PI229333 | 2.5 |  | X |
| PI238109 | 2.3 | X |  |
| PI240667A | 1 | X |  |
| PI258383 | 2 | X |  |
| PI291309C | 2 | X |  |
| PI341252 | 2.5 | X | X |
| PI374189 | 2.3 | X |  |
| PI398335 | 2 | X |  |
| PI399070 | 2.5 | X |  |
| PI407831 | 2.5 | X |  |
| PI407833C | 2 |  | X |
| PI407845A | 2.5 | X |  |
| PI407858 | 2.3 | X | X |
| PI407881 | 2.3 | X |  |
| PI408088 | 2.3 | X |  |
| PI408134B | 2 | X |  |
| PI408272B | 2 | X |  |
| PI417122 | 2.5 | X |  |
| PI417126 | 2.5 | X |  |
| PI417235 | 2 | X |  |
| PI417335 | 2.3 | X |  |
| PI423717 | 2 | X |  |
| PI423722 | 2.3 | X |  |
| PI423730B | 2.3 | X |  |
| PI423852 | 2.3 | X | X |
| PI424190 | 2.5 | X |  |
| PI434973A | 2.5 | X |  |
| PI437110A | 2.3 | X |  |
| PI437437A | 1.5 |  | X |
| PI437740B | 2.3 | X | X |
| PI437921 | 2 | X |  |
| PI437982 | 2.3 | X | X |
| PI438073 | 2.3 | X |  |
| PI438371 | 2.5 | X |  |
| PI438480 | 2.5 | X |  |
| PI479735 | 2.3 | X |  |
| PI497965 | 2.5 | X |  |
| PI506737 | 2 | X |  |
| PI506863 | 2 | X |  |
| PI507142 | 2.5 |  | X |
| PI508269 | 2 | X |  |
| PI548325 | 2 | X |  |
| PI561289 | 2 | X | X |
| PI561329 | 2.5 | X |  |
| PI561330A | 2 |  | X |
| PI561337 | 2 |  | X |
| PI561377 | 2.3 |  | X |
| PI566978 | 2.5 | X |  |
| PI567010B | 2.3 | X |  |
| PI567093B | 2 | X | X |
| PI567104B | 2.5 | X | X |
| PI567108B | 2.5 | X | X |
| PI567129 | 2.3 | X | X |
| PI567140B | 2.5 | X |  |
| PI567174C | 2.3 |  | X |
| PI567175C | 2 | X | X |
| PI567300A | 2 | X |  |
| PI567409A | 2.3 | X |  |
| PI567470 | 2 | X |  |
| PI567473C | 2.5 | X |  |
| PI567474 | 2.3 | X |  |
| PI567489A | 2 | X |  |
| PI567507B | 2 | X |  |
| PI567554A | 2 | X |  |
| PI567560 | 2.5 | X | X |
| PI567561 | 2.5 | X |  |
| PI567675 | 2.3 |  | X |
| PI567692 | 2 | X | X |
| PI567718 | 2 | X | X |
| PI567780A | 2.3 | X |  |
| PI578305B | 2.5 | X |  |
| PI587598A | 2.5 | X |  |
| PI587914B | 2 |  | X |
| PI587922A | 2 |  | X |
| PI587935A | 2.3 |  | X |
| PI588000 | 2.5 |  | X |
| PI588034 | 2.5 |  | X |
| PI592962B | 2.3 | X |  |
| PI594525 | 2.5 | X | X |
| PI594538A | 2 | X | X |
| PI594767B | 1 | X |  |
| PI597480A | 2.3 | X |  |
| PI603293B | 2.3 | X |  |
| PI603296 | 2.5 |  | X |
| PI603429D | 2.5 | X |  |
| PI603564A | 2.3 | X |  |
| PI603612 | 2.3 | X | X |
| PI603704A | 2.5 | X | X |
| PI605891B | 2.5 | X |  |
| PI628870 | 1.5 |  | X |
| PI628932 | 2.4 | X |  |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A method of producing a population of soybean plants or seeds comprising ASR (Asian Soybean Rust) resistance locus 1, wherein said ASR resistance locus 1 is also present in soybean accession PI 200492, said method comprising:

genotyping a first population of soybean plants or seeds, said first population of soybean plants or seeds comprising ASR resistance locus 1;

selecting from said first population one or more soybean plants or seeds comprising said ASR resistance locus 1 based upon said genotyping; and producing from said selected one or more soybean plants or seeds a second population of soybean plants or seeds comprising said ASR resistance locus 1.

2. The method of claim 1, wherein said ASR resistance locus 1 is localized to linkage group G.

3. The method of claim 2, wherein said ASR resistance locus 1 is mapped within 10 centimorgans or less from a SNP marker selected from the group consisting of
NS0093250 capable of being identified with probes with SEQ ID NOs: 100 and 101,
NS0119710 capable of being identified with probes with SEQ ID NOs: 102 and 103,
NS0103004 capable of being identified with probes with SEQ ID NOs: 104 and 105,
NS0099454 capable of being identified with probes with SEQ ID NOs: 106 and 107,
NS0102630 capable of being identified with probes with SEQ ID NOs: 108 and 109,
NS0102915 capable of being identified with probes with SEQ ID NOs: 110 and 111,
NS0102913 capable of being identified with probes with SEQ ID NOs: 112 and 113,
NS0123728 capable of being identified with probes with SEQ ID NOs: 114 and 115,
NS0129943 capable of being identified with probes with SEQ ID NOs: 116 and 117,
NS0102168 capable of being identified with probes with SEQ ID NOs: 118 and 119,
NS0092723 capable of being identified with probes with SEQ ID NOs: 120 and 121,
NS0098177 capable of being identified with probes with SEQ ID NOs: 122 and 123,
NS0127343 capable of being identified with probes with SEQ ID NOs: 124 and 125, and
NS0101121 capable of being identified with probes with SEQ ID NOs: 126 and 127.

4. The method of claim 1, wherein said ASR resistance locus 1 confers a slow rust phenotype.

5. The method of claim 1, wherein said ASR resistance is resistance to *Phakopsora pachyrhizi* or *Phakopsora meibomiae*.

6. The method of claim 1, wherein said second population of soybean plants or seeds comprise one or more agronomic traits selected from the group consisting of herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, lower raffinose, environmental stress resistance, increased digestibility, production of industrial enzymes, production of pharmaceutical proteins, production of pharmaceutical peptides, production of pharmaceutical small molecules, improved processing traits, improved flavor, improved nitrogen fixation, improved hybrid seed production, reduced allergenicity, and improved production of biopolymers and biofuels.

7. The method of claim 1, wherein said second population of soybean plants or seeds comprise one or more traits selected from the group consisting of insect resistance, glyphosate resistance, resistance to Soybean Cyst Nematode, resistance to *Meloidogyne javanica*, resistance to *Meloidogyne arenaria*, resistance to *Meloidogyne hapla*, resistance to *Meloidogyne incognita*, resistance to *Diaporthe phaseolorum* var. *caulivora*, and resistance to *Corynespora cassiicola*.

8. The method of claim 1, wherein said second population of soybean plants or seeds are transgenic.

9. The method of claim 1, wherein said genotyping uses one or more markers selected from the group consisting of a simple sequence repeat (SSR) marker, an AFLP marker, an RFLP marker, an RAPD marker, a phenotypic marker, a SNP, an isozyme marker, and microarray transcription profile.

10. The method of claim 1, wherein said genotyping involves a molecular marker located within 10 centimorgan from said ASR resistance locus 1.

11. The method of claim 1, wherein said genotyping involves a molecular marker located within 5 centimorgan from said ASR resistance locus 1.

12. The method of claim 1, wherein said genotyping uses one or more methods selected from the group consisting of polymerase chain reaction (PCR), Ligase Chain Reaction (LCR), Oligonucleotide Ligation Assay (OLA), allele-specific oligomers, branched DNA technology, transcription-based amplification systems, isothermal amplification methods, and Single Strand Conformation Polymorphism (SSCP) analysis.

13. The method of claim 1, wherein said genotyping comprises detecting one or more SNP polymorphisms.

14. The method of claim 13, wherein said genotyping comprises a primer-extension assay.

15. The method of claim 13, wherein said genotyping comprises a GOOD assay.

16. The method of claim 13, wherein said genotyping uses one or more methods selected from the group consisting of oligonucleotide hybridization, Taq-Man assay, molecular beacon, electronic dot blot assay, and denaturing high-performance liquid chromatography.

17. The method of claim 1, wherein said genotyping involves a SNP marker selected from the group consisting of
NS0093250 capable of being identified with probes with SEQ ID NOs: 100 and 101,
NS0119710 capable of being identified with probes with SEQ ID NOs: 102 and 103,
NS0103004 capable of being identified with probes with SEQ ID NOs: 104 and 105,
NS0099454 capable of being identified with probes with SEQ ID NOs: 106 and 107,
NS0102630 capable of being identified with probes with SEQ ID NOs: 108 and 109,
NS0102915 capable of being identified with probes with SEQ ID NOs: 110 and 111,
NS0102913 capable of being identified with probes with SEQ ID NOs: 112 and 113,
NS0123728 capable of being identified with probes with SEQ ID NOs: 114 and 115,
NS0129943 capable of being identified with probes with SEQ ID NOs: 116 and 117,
NS0102168 capable of being identified with probes with SEQ ID NOs: 118 and 119,
NS0092723 capable of being identified with probes with SEQ ID NOs: 120 and 121,
NS0098177 capable of being identified with probes with SEQ ID NOs: 122 and 123,
NS0127343 capable of being identified with probes with SEQ ID NOs: 124 and 125, and
NS0101121 capable of being identified with probes with SEQ ID NOs: 126 and 127.

18. The method of claim 1, wherein said genotyping involves a marker within 10 centimorgans or less from a SNP marker selected from the group consisting of
NS0093250 capable of being identified with probes with SEQ ID NOs: 100 and 101, NS0119710 capable of being identified with probes with
  SEQ ID NOs: 102 and 103,
NS0103004 capable of being identified with probes with
  SEQ ID NOs: 104 and 105,
NS0099454 capable of being identified with probes with
  SEQ ID NOs: 106 and 107,
NS0102630 capable of being identified with probes with
  SEQ ID NOs: 108 and 109,
NS0102915 capable of being identified with probes with
  SEQ ID NOs: 110 and 111,
NS0102913 capable of being identified with probes with
  SEQ ID NOs: 112 and 113,
NS0123728 capable of being identified with probes with
  SEQ ID NOs: 114 and 115,
NS0129943 capable of being identified with probes with
  SEQ ID NOs: 116 and 117,
NS0102168 capable of being identified with probes with
  SEQ ID NOs: 118 and 119,
NS0092723 capable of being identified with probes with
  SEQ ID NOs: 120 and 121,
NS0098177 capable of being identified with probes with
  SEQ ID NOs: 122 and 123,
NS0127343 capable of being identified with probes with
  SEQ ID NOs: 124 and 125, and
NS0101121 capable of being identified with probes with
  SEQ ID NOs: 126 and 127.

* * * * *

UNITED STATES PATENT AND TRADEMARK OFFICE
CERTIFICATE OF CORRECTION

PATENT NO. : 9,091,681 B2  
APPLICATION NO. : 14/191044  
DATED : July 28, 2015  
INVENTOR(S) : George James Baley et al.

Page 1 of 1

It is certified that error appears in the above-identified patent and that said Letters Patent is hereby corrected as shown below:

In The Specification

In column 10, ln. 59, please change "DKXTJ54×9" to --DKXTJ54X9--;

in column 11, ln. 60, please change "53832-4" to --S3832-4--;

in column 12, ln. 2, please change "V31SRR" to --V315RR--; and in column 15, ln. 34, please change "Glycine ma" to --Glycine max--.

Signed and Sealed this  
Twenty-second Day of December, 2015

Michelle K. Lee  
*Director of the United States Patent and Trademark Office*

SEQUENCE LISTING

<160> NUMBER OF SEQ ID NOS: 165

<210> SEQ ID NO 1
<211> LENGTH: 21
<212> TYPE: DNA
<213> ORGANISM: Artificial Sequence
<220> FEATURE:
<223> OTHER INFORMATION: Description of artificial sequence: synthetic primer

<400> SEQUENCE: 1
cacctgttgc ttctccacca t                                      21

<210> SEQ ID NO 2
<211> LENGTH: 20
<212> TYPE: DNA
<213> ORGANISM: Artificial Sequence
<220> FEATURE:
<223> OTHER INFORMATION: Description of artificial sequence: synthetic
      primer

<400> SEQUENCE: 2
gggtggtgct cttggaggta                                        20

<210> SEQ ID NO 3
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 3
taaagcaaaa ggacgttacg acaa                                   24

<210> SEQ ID NO 4
<211> LENGTH: 23
<212> TYPE: DNA
<213> ORGANISM: Artificial Sequence
<220> FEATURE:
<223> OTHER INFORMATION: Description of artificial sequence: synthetic
      primer

<400> SEQUENCE: 4
gcattgattt gtccacgaag aac                                    23

<210> SEQ ID NO 5
<211> LENGTH: 29
<212> TYPE: DNA
<213> ORGANISM: Artificial Sequence
<220> FEATURE:
<223> OTHER INFORMATION: Description of artificial sequence: synthetic
      primer

<400> SEQUENCE: 5
ttgcaatttt ttatatcttg atttcacat                              29

<210> SEQ ID NO 6
<211> LENGTH: 23
<212> TYPE: DNA
<213> ORGANISM: Artificial Sequence
<220> FEATURE:
<223> OTHER INFORMATION: Description of artificial sequence: synthetic
      primer

<400> SEQUENCE: 6
gcgaagaatc aaaactggtc aaa                                    23

<210> SEQ ID NO 7
<211> LENGTH: 22
<212> TYPE: DNA
<213> ORGANISM: Artificial Sequence
<220> FEATURE:
<223> OTHER INFORMATION: Description of artificial sequence: synthetic
      primer

<400> SEQUENCE: 7
aagtggagga ggaaatgatg ga                                    22

<210> SEQ ID NO 8
<211> LENGTH: 21
<212> TYPE: DNA
<213> ORGANISM: Artificial Sequence
<220> FEATURE:
<223> OTHER INFORMATION: Description of artificial sequence: synthetic
      primer

<400> SEQUENCE: 8
caagggccct gattatgtga a                                     21

<210> SEQ ID NO 9
<211> LENGTH: 27
<212> TYPE: DNA
<213> ORGANISM: Artificial Sequence
<220> FEATURE:
<223> OTHER INFORMATION: Description of artificial sequence: synthetic
      primer

<400> SEQUENCE: 9
acaaggacaa ggctatgaga agtaaga                               27

<210> SEQ ID NO 10
<211> LENGTH: 20
<212> TYPE: DNA
<213> ORGANISM: Artificial Sequence
<220> FEATURE:
<223> OTHER INFORMATION: Description of artificial sequence: synthetic
      primer

<400> SEQUENCE: 10
ggccatgaat caagccactt                                       20

<210> SEQ ID NO 11
<211> LENGTH: 23
<212> TYPE: DNA
<213> ORGANISM: Artificial Sequence
<220> FEATURE:
<223> OTHER INFORMATION: Description of artificial sequence: synthetic
      primer

<400> SEQUENCE: 11
gagttagatt tatccggcaa cga                                   23

<210> SEQ ID NO 12
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 12
cccgaagaga tgtcatgtta acaa                                  24

<210> SEQ ID NO 13
<211> LENGTH: 26
<212> TYPE: DNA
<213> ORGANISM: Artificial Sequence
<220> FEATURE:
<223> OTHER INFORMATION: Description of artificial sequence: synthetic
      primer

```
<400> SEQUENCE: 13
gggttacctt catagctgct attttc                                           26

<210> SEQ ID NO 14
<211> LENGTH: 19
<212> TYPE: DNA
<213> ORGANISM: Artificial Sequence
<220> FEATURE:
<223> OTHER INFORMATION: Description of artificial sequence: synthetic
      primer

<400> SEQUENCE: 14
gggcacaaca cctgaatgg                                                   19

<210> SEQ ID NO 15
<211> LENGTH: 29
<212> TYPE: DNA
<213> ORGANISM: Artificial Sequence
<220> FEATURE:
<223> OTHER INFORMATION: Description of artificial sequence: synthetic
      primer

<400> SEQUENCE: 15
ccgcagtgaa tcaagtaatt agttaataa                                        29

<210> SEQ ID NO 16
<211> LENGTH: 27
<212> TYPE: DNA
<213> ORGANISM: Artificial Sequence
<220> FEATURE:
<223> OTHER INFORMATION: Description of artificial sequence: synthetic
      primer

<400> SEQUENCE: 16
aaggtttagt tcgatcagtg attttga                                          27

<210> SEQ ID NO 17
<211> LENGTH: 32
<212> TYPE: DNA
<213> ORGANISM: Artificial Sequence
<220> FEATURE:
<223> OTHER INFORMATION: Description of artificial sequence: synthetic
      primer

<400> SEQUENCE: 17
ggtttcagat attttgataa gctaattaga tg                                    32

<210> SEQ ID NO 18
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 18
caagaactca cattcctcag atgaag                                           26

<210> SEQ ID NO 19
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 19
```
agggcctatt gtgatgatta agga                                          24

<210> SEQ ID NO 20
<211> LENGTH: 24
<212> TYPE: DNA
<213> ORGANISM: Artificial Sequence
<220> FEATURE:
<223> OTHER INFORMATION: Description of artificial sequence: synthetic
     primer

<400> SEQUENCE: 20
aaatctgaaa aagcatccca aaag                                          24

<210> SEQ ID NO 21
<211> LENGTH: 27
<212> TYPE: DNA
<213> ORGANISM: Artificial Sequence
<220> FEATURE:
<223> OTHER INFORMATION: Description of artificial sequence: synthetic
     primer

<400> SEQUENCE: 21
gtaataatcc caaacatttt tcttcga                                       27

<210> SEQ ID NO 22
<211> LENGTH: 28
<212> TYPE: DNA
<213> ORGANISM: Artificial Sequence
<220> FEATURE:
<223> OTHER INFORMATION: Description of artificial sequence: synthetic
     primer

<400> SEQUENCE: 22
gggatgagtt gaattaattt tcaaagta                                      28

<210> SEQ ID NO 23
<211> LENGTH: 26
<212> TYPE: DNA
<213> ORGANISM: Artificial Sequence
<220> FEATURE:
<223> OTHER INFORMATION: Description of artificial sequence: synthetic
     primer

<400> SEQUENCE: 23
gcatgctgct tttaactatg aaacat                                        26

<210> SEQ ID NO 24
<211> LENGTH: 28
<212> TYPE: DNA
<213> ORGANISM: Artificial Sequence
<220> FEATURE:
<223> OTHER INFORMATION: Description of artificial sequence: synthetic
     primer

<400> SEQUENCE: 24
gttgatgaag tatacaattt catttgca                                      28

<210> SEQ ID NO 25
<211> LENGTH: 26
<212> TYPE: DNA
<213> ORGANISM: Artificial Sequence
<220> FEATURE:
<223> OTHER INFORMATION: Description of artificial sequence: synthetic
     primer

<400> SEQUENCE: 25
aaaccaagtg aggagacatt aattca                                          26

<210> SEQ ID NO 26
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 26
ggctgagttg ggttaatatc acatt                                           25

<210> SEQ ID NO 27
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 27
aaaaagttga atgatcacct gcatt                                           25

<210> SEQ ID NO 28
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 28
catttgtctt ttgcaggcta atctaa                                          26

<210> SEQ ID NO 29
<211> LENGTH: 22
<212> TYPE: DNA
<213> ORGANISM: Artificial Sequence
<220> FEATURE:
<223> OTHER INFORMATION: Description of artificial sequence: synthetic
      primer

<400> SEQUENCE: 29
atgggcaaca gttgtcatat gg                                              22

<210> SEQ ID NO 30
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 30
tgatgatggc atggaattat tacc                                            24

<210> SEQ ID NO 31
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 31 attttggta cctctctttc cttcaa                                           26

<210> SEQ ID NO 32
<211> LENGTH: 26
<212> TYPE: DNA
<213> ORGANISM: Artificial Sequence
<220> FEATURE:
<223> OTHER INFORMATION: Description of artificial sequence: synthetic primer

<400> SEQUENCE: 32
ttattaccaa catccaaaca cacaca                                          26

<210> SEQ ID NO 33
<211> LENGTH: 26
<212> TYPE: DNA
<213> ORGANISM: Artificial Sequence
<220> FEATURE:
<223> OTHER INFORMATION: Description of artificial sequence: synthetic primer

<400> SEQUENCE: 33
gtggcaagga ataatcagt agcttt                                           26

<210> SEQ ID NO 34
<211> LENGTH: 31
<212> TYPE: DNA
<213> ORGANISM: Artificial Sequence
<220> FEATURE:
<223> OTHER INFORMATION: Description of artificial sequence: synthetic primer

<400> SEQUENCE: 34
atccttaaca tgatttatgt tgtaatttgt g                                    31

<210> SEQ ID NO 35
<211> LENGTH: 24
<212> TYPE: DNA
<213> ORGANISM: Artificial Sequence
<220> FEATURE:
<223> OTHER INFORMATION: Description of artificial sequence: synthetic primer

<400> SEQUENCE: 35
ggaggaaggg tatgcaactt ttac                                            24

<210> SEQ ID NO 36
<211> LENGTH: 23
<212> TYPE: DNA
<213> ORGANISM: Artificial Sequence
<220> FEATURE:
<223> OTHER INFORMATION: Description of artificial sequence: synthetic primer

<400> SEQUENCE: 36
catttcttca acatccgaac caa                                             23

<210> SEQ ID NO 37
<211> LENGTH: 27
<212> TYPE: DNA
<213> ORGANISM: Artificial Sequence
<220> FEATURE:
<223> OTHER INFORMATION: Description of artificial sequence: synthetic primer

<400> SEQUENCE: 37
cataagacgc gttaaacgtc agtactt                                         27

<210> SEQ ID NO 38
<211> LENGTH: 26
<212> TYPE: DNA
<213> ORGANISM: Artificial Sequence
<220> FEATURE:
<223> OTHER INFORMATION: Description of artificial sequence: synthetic primer

<400> SEQUENCE: 38
ccaacgatct tgctaattag cacata                                    26

<210> SEQ ID NO 39
<211> LENGTH: 20
<212> TYPE: DNA
<213> ORGANISM: Artificial Sequence
<220> FEATURE:
<223> OTHER INFORMATION: Description of artificial sequence: synthetic primer

<400> SEQUENCE: 39
cgaggttgtt agccgttgga                                           20

<210> SEQ ID NO 40
<211> LENGTH: 26
<212> TYPE: DNA
<213> ORGANISM: Artificial Sequence
<220> FEATURE:
<223> OTHER INFORMATION: Description of artificial sequence: synthetic primer

<400> SEQUENCE: 40
accaatcaac ctttctttat cgtttt                                    26

<210> SEQ ID NO 41
<211> LENGTH: 25
<212> TYPE: DNA
<213> ORGANISM: Artificial Sequence
<220> FEATURE:
<223> OTHER INFORMATION: Description of artificial sequence: synthetic primer

<400> SEQUENCE: 41
tgtggtaatg cattttcttg gtctt                                     25

<210> SEQ ID NO 42
<211> LENGTH: 26
<212> TYPE: DNA
<213> ORGANISM: Artificial Sequence
<220> FEATURE:
<223> OTHER INFORMATION: Description of artificial sequence: synthetic primer

<400> SEQUENCE: 42
gaacaggttc caacactaat gtgagt                                    26

<210> SEQ ID NO 43
<211> LENGTH: 23
<212> TYPE: DNA
<213> ORGANISM: Artificial Sequence
<220> FEATURE:
<223> OTHER INFORMATION: Description of artificial sequence: synthetic primer

<400> SEQUENCE: 43
tggaagcaat gtcaatcaat tca                                       23

```
<210> SEQ ID NO 44
<211> LENGTH: 22
<212> TYPE: DNA
<213> ORGANISM: Artificial Sequence
<220> FEATURE:
<223> OTHER INFORMATION: Description of artificial sequence: synthetic
      primer

<400> SEQUENCE: 44
tccatggcat ccttaagggt aa                                              22

<210> SEQ ID NO 45
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 45
caattttatt cttggcacct tcatt                                           25

<210> SEQ ID NO 46
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 46
gtgaagtgta ttccagtggt gtga                                            24

<210> SEQ ID NO 47
<211> LENGTH: 24
<212> TYPE: DNA
<213> ORGANISM: Artificial Sequence
<220> FEATURE:
<223> OTHER INFORMATION: Description of artificial sequence: synthetic
      primer

<400> SEQUENCE: 47
cgcatatcaa caggacagac aaaa                                            24

<210> SEQ ID NO 48
<211> LENGTH: 28
<212> TYPE: DNA
<213> ORGANISM: Artificial Sequence
<220> FEATURE:
<223> OTHER INFORMATION: Description of artificial sequence: synthetic
      primer

<400> SEQUENCE: 48
cgttgagagt actattaata gccctcaa                                        28

<210> SEQ ID NO 49
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 49
caggcgatcc ctaattataa ttatcc                                          26

<210> SEQ ID NO 50
```

```
<211> LENGTH: 19
<212> TYPE: DNA
<213> ORGANISM: Artificial Sequence
<220> FEATURE:
<223> OTHER INFORMATION: Description of artificial sequence: synthetic
      primer

<400> SEQUENCE: 50
cgcaggaggg acatggtaa                                                  19

<210> SEQ ID NO 51
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 51
ggagacagtc atgacatgca tattg                                           25

<210> SEQ ID NO 52
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 52
tcaactgcat tgttgcttta atttct                                          26

<210> SEQ ID NO 53
<211> LENGTH: 22
<212> TYPE: DNA
<213> ORGANISM: Artificial Sequence
<220> FEATURE:
<223> OTHER INFORMATION: Description of artificial sequence: synthetic
      primer

<400> SEQUENCE: 53
accgtgtcct taaagctttc ca                                              22

<210> SEQ ID NO 54
<211> LENGTH: 27
<212> TYPE: DNA
<213> ORGANISM: Artificial Sequence
<220> FEATURE:
<223> OTHER INFORMATION: Description of artificial sequence: synthetic
      primer

<400> SEQUENCE: 54
aaggttatat aaatcaaggg gaatgct                                         27

<210> SEQ ID NO 55
<211> LENGTH: 19
<212> TYPE: DNA
<213> ORGANISM: Artificial Sequence
<220> FEATURE:
<223> OTHER INFORMATION: Description of artificial sequence: synthetic
      primer

<400> SEQUENCE: 55
cgcctgggag caacaagat                                                  19

<210> SEQ ID NO 56
<211> LENGTH: 21
```

```
<212> TYPE: DNA
<213> ORGANISM: Artificial Sequence
<220> FEATURE:
<223> OTHER INFORMATION: Description of artificial sequence: synthetic
      primer

<400> SEQUENCE: 56
ttcgaagaat gggagcagaa a                                              21

<210> SEQ ID NO 57
<211> LENGTH: 26
<212> TYPE: DNA
<213> ORGANISM: Artificial Sequence
<220> FEATURE:
<223> OTHER INFORMATION: Description of artificial sequence: synthetic
      primer

<400> SEQUENCE: 57
tggagatcat ctataccgaa tggatt                                         26

<210> SEQ ID NO 58
<211> LENGTH: 30
<212> TYPE: DNA
<213> ORGANISM: Artificial Sequence
<220> FEATURE:
<223> OTHER INFORMATION: Description of artificial sequence: synthetic
      primer

<400> SEQUENCE: 58
tgtcttgata attacacagc tctgatacaa                                     30

<210> SEQ ID NO 59
<211> LENGTH: 20
<212> TYPE: DNA
<213> ORGANISM: Artificial Sequence
<220> FEATURE:
<223> OTHER INFORMATION: Description of artificial sequence: synthetic
      primer

<400> SEQUENCE: 59
gaaatgcggg catatatgca                                                20

<210> SEQ ID NO 60
<211> LENGTH: 29
<212> TYPE: DNA
<213> ORGANISM: Artificial Sequence
<220> FEATURE:
<223> OTHER INFORMATION: Description of artificial sequence: synthetic
      primer

<400> SEQUENCE: 60
gcttctggtt ctagttctaa cttctacca                                      29

<210> SEQ ID NO 61
<211> LENGTH: 17
<212> TYPE: DNA
<213> ORGANISM: Artificial Sequence
<220> FEATURE:
<223> OTHER INFORMATION: Description of artificial sequence: synthetic
      primer

<400> SEQUENCE: 61
gggtcgggtc gaaccaa                                                   17

<210> SEQ ID NO 62
<211> LENGTH: 25
<212> TYPE: DNA
```

<213> ORGANISM: Artificial Sequence
<220> FEATURE:
<223> OTHER INFORMATION: Description of artificial sequence: synthetic primer

<400> SEQUENCE: 62
cgaatattca gtgaaacggg ttaaa       25

<210> SEQ ID NO 63
<211> LENGTH: 21
<212> TYPE: DNA
<213> ORGANISM: Artificial Sequence
<220> FEATURE:
<223> OTHER INFORMATION: Description of artificial sequence: synthetic primer

<400> SEQUENCE: 63
aggcggcttg aagaatttga c       21

<210> SEQ ID NO 64
<211> LENGTH: 23
<212> TYPE: DNA
<213> ORGANISM: Artificial Sequence
<220> FEATURE:
<223> OTHER INFORMATION: Description of artificial sequence: synthetic primer

<400> SEQUENCE: 64
ttagccaaaa tccatagcag gaa       23

<210> SEQ ID NO 65
<211> LENGTH: 22
<212> TYPE: DNA
<213> ORGANISM: Artificial Sequence
<220> FEATURE:
<223> OTHER INFORMATION: Description of artificial sequence: synthetic primer

<400> SEQUENCE: 65
aacatcaggg tcagcattcc at       22

<210> SEQ ID NO 66
<211> LENGTH: 24
<212> TYPE: DNA
<213> ORGANISM: Artificial Sequence
<220> FEATURE:
<223> OTHER INFORMATION: Description of artificial sequence: synthetic primer

<400> SEQUENCE: 66
cacaatatgg tcagacagct ttcc       24

<210> SEQ ID NO 67
<211> LENGTH: 492
<212> TYPE: DNA
<213> ORGANISM: Glycine max

<400> SEQUENCE: 67
aacaaactcc aacaccccaa cgacgtcatt catggaagga cgctgggtcc catcctcatg       60
caaacagctt agcgcaacct cgccaaatct gttcaaacac tgagttgcta tctggccctt      120
tagttttgca tccacaatgg cacccagaga acccttctga tatagatgct tcgcccaatc      180
aaccagtgac acctgttgct tctccaccat gcggagcaaa ggctgtctcc cagacaaatac     240 ctccaagagc accaccccaa aggagtacac gtcagacttc tcagtcaaac gctgtcgttt      300

```
gtaatactcc gggtctaaat atccaacgct acctttcacc tgagtgctca catgggtcat    360
tgaagaacca atgggcccaa ttcgggataa cccgaagtct gaaaccttgg ccacccattt    420
ctcatccaat aagatgttgg tgctcttcac gtcacggtga atgatcatgt gcttcgcacc    480
cgtatgcaga ta                                                        492
```

<210> SEQ ID NO 68
<211> LENGTH: 655
<212> TYPE: DNA
<213> ORGANISM: Glycine max

<400> SEQUENCE: 68

```
attgataata taaagcaaaa ggacgttacg acaaaaagct cgttccccat gaatagttct     60
tcgtggacaa atcaatgctc tgtagtactg ttggcttaga ttaattttac tacggattta    120
cctacggtca caaaattgac tgctgaaaat ctttacagta cttcatcttt ttcatacatt    180
aaaaatttac tttatttctt atatatatat tattagtata atcaattatg catatatacc    240
aaccgatcga gcccttgctt catttccaaa caatatggca tacgaaaatc tatttattat    300
atagagatta aatgtgaaca cttcttagtt cttaactcgt gtggttgtat tattatgaaa    360
caccagcctc ttcggctata ctcaattcta ttctattaag tcttggtta aagttttaca    420 ttcatcttta ttttaacagt atcctatata agaaaatagg caaaaagatg ccacagctgc    480
attaatttgc tagaaaaata taggtgacta gcctgtaaaa ttatgtcaat ctcttgctct    540
gctaccttat caagccgcac tgttgcactg attgcatgta gaggcatcgc aacagcactt    600
aatttgcgag atactggtag tatatgattt taattggacc ccaacaagcc atttt        655
```

<210> SEQ ID NO 69
<211> LENGTH: 668
<212> TYPE: DNA
<213> ORGANISM: Glycine max

<400> SEQUENCE: 69

```
acttttgtac aagctcatca atgtatatca tagttttga aatcggtaat gaaccaatgc      60
aaaaaatggt ttaaacccgt atttctttag gagatattag gtgaattgga tgattaagga    120
aaaatggaag gaaaaaatat cacaagttta attcctgcta ataaaattaa tattttaaca    180
actaacattt gctcatataa aaaacccccaa tatttttaa aatttaatct aaagcatttt    240
taagttaact aaaaacatat ttaataagaa ttaaaatagt tgtaaattat tttattaatt    300
attattaatt actcttataa aacatataat ttaatcatta tatcaatttg caatttttta    360
tatcttgatt tcacataatc ttatattaac ttcttgtttt ctttttttatt ctagatgtaa    420 acttgttatg aagtgatttt actgggtttt gaccagtttt gattcttcgc caattccttg    480
aacgattttg tagtttattt atatcaaaca ctaaatcaat tcatcagttt tctgggtcaa    540
accaacaaat ttgatctggc atcttataac acaattgttt atggaaaaca catctaatgt    600
gattaaacaa ggacatcacg caacttggca gttaccactt ctttgccttt gctccaatat    660
ttttattt                                                             668
```

<210> SEQ ID NO 70
<211> LENGTH: 612
<212> TYPE: DNA
<213> ORGANISM: Glycine max

<400> SEQUENCE: 70

```
ctagtggtga caatattcct gaaagggggtg gcaacaatgg tgggaggtcg ggtaatccag     60
```

```
gaatgggagg aagaagacca ccaggtgttt ttggattttg aagtggagga ggaaatgatg      120
gatctatttt tggaggaaat atgtgtttca cataatcagg gcccttgatg ttttgaatgc      180 ttggttttc gttgcaaaga actggctgtc taagaggctt gaatgagaaa aagccggctg       240
agaatatgtg tagtccttcc tttctggact tgaggcacag tgatgaagaa gttgctgctg      300
aggcaacagc acaataaggc tcactgctat ttattagttt cacagtgcat cctttattc       360 ttttcacatg tttgctcact gagaaaggca actgcacctt gaactcccca tgctcatctg      420
tcttcacttc tttcctaaac cttggctttg acctcccata cccatctttg cattctacag      480
caactgatgc acctgccatc atgaatatag aaaaacataa gacaacatga cttcataatc      540
aaaatttaga gcatgtgtgt aagagttaag agatatgaaa ctgaaccttt ttaagaaaaa      600
taagtcaagc ag                                                          612
```

<210> SEQ ID NO 71
<211> LENGTH: 941
<212> TYPE: DNA
<213> ORGANISM: Glycine max

<400> SEQUENCE: 71

```
caagcttgtt gcctgcagaa aaagcacatg ggatagttgt taatagtttt gaagagttgg      60
aagcagaata tgttgaagag tgtcaaagat ttacggacca tagggtatgg tgtgttgggc      120
ctgtgtcgct gtcaaataag gatgacaagg acaaggctat gagaagtaag agaaactcaa      180
gtgatattga gagtgagtat gtgaagtggc ttgattcatg gcctccgagg tcagtgattt      240
atgtttgcct tggtagccta aaccgtgcaa cgccagagca gttgatagag ctcgggttag      300
gattggaagc gacaaaaagg ccattcattt gggtgcttag aggtgcatat ggaagagagg      360
agatggagaa gtggctgttg aagatgggt ttgaagagag ggtgaaaggg agagggcttt       420
tgatcaaggg ttgggtgcca caagtgttga tcttatcaca tagagcaata ggagcgttca      480
tgacacattg cggatggaat tccacactcg aagggatttg tgctggcgtg ccgttggtaa      540 ctttcctct gtttgctgag cagttcatca atgagaaact tgtacaagtg gtgaagattg       600
gcgtgagtgt gggagctgaa tctgttgttc acttgggtga agaagataag tctcgggttc      660
aggtgaccag agaaaatgtt ctggattcta ttgaaaggta atgggagaat ggccaaaaaa      720
aaaaaaaata taggaaaggg cttaagta ttccgccatt ggcagggaaa gcaaaaaaa         780 aagtgggttt ttttctcac atggtcctac tcattgggcc atatacctt ggagggttaa        840 ccaagtttaa cagggttct atttttgtt tcaacacca attgctttc tcaagggtca          900 accttaaacc caatttgtct tccgaaagaa tttttttt a                            941
```

<210> SEQ ID NO 72
<211> LENGTH: 652
<212> TYPE: DNA
<213> ORGANISM: Glycine max

<400> SEQUENCE: 72

```
taattatatt atttgatttt ttttattcat gacatttatt ttatataatt ttttcttagt      60
ttggtcaaat attatcatcc ttttcattat ctcactaata aggtggattt ttttgtttg       120 acaaaatttc tttttttcaga ttggtcaaag ctaagaaga tagaggagtt agatttatcc      180
ggcaacgaat ttaagggacc acttccctcg tcttttgtta acatgacatc tcttcgggag     240
ttggaaattt ctcataatca cttcattgga aatttcgatt ctaacattgc aagccttaca     300
```

```
tcacttgaat attttggttt tacagaaaac caatttgaag ttcctgtttc tttctcaaca    360
tttgccaatc attcaaagat caagttgatc gacggtggag gaaacagatt catattggac    420
tcacaacata gtttaccaac ttggattcca aaatttcagt tacaagagct tagtgtgtct    480
tcaacaactg aaactaagtc tcttccactc cccaattttc ttctatacca aaacagttta    540
atcagcctag acttcagtag ttggaagttg gaaggagact ttccttattg gttgttggaa    600
aacaacacaa aaatgactga agctctgttt agaaattgct ctttcactgg tg            652
```

<210> SEQ ID NO 73
<211> LENGTH: 671
<212> TYPE: DNA
<213> ORGANISM: Glycine max

<400> SEQUENCE: 73

```
aaggattgat gtataaagct attgctgttg ccaacaatgc tgctgagaat gacactgcaa     60
agctcacata gaaaacatac atgtccacca aactaccatc gtctacatga gtgtgtgaat    120
catttggtat aatactaggt ggaggattgc aacttttga cagtggaggt ccacaaagga    180
aggggttacc ttcatagctg ctattttcaa aggtcgagaa ttgtcctttc cattcaggtg    240
ttgtgcccga taagttgttg tgtgccacac tgaatacttc aagggaggtt agcttactca    300
gttgaggagg aatttgacca ctcaacttgt taaatgaaag gtctaaactc tctgtttgta    360
ccaaattgga gaatgtagct ggaatttgcc caatcaaatc attatgagac aagttcaatg    420
ctcgaattct tgtcaaattt ccaagatcaa atgggatatt cccattcagt ttattgtggg    480
acaagtcaat tccagacata taagcaagga tgctccttgt gtaagtgtcg gttctcttct    540
ttgaagtgaa atttactttc tcttccacat ttggtaattg tgatgggaaa attttatttt    600
ggcctgtaga accccaaccg gacaatcttt ccaaaaaccg ttcaggatcc ttattctcaa    660
aagacatttt t                                                          671
```

<210> SEQ ID NO 74
<211> LENGTH: 619
<212> TYPE: DNA
<213> ORGANISM: Glycine max

<400> SEQUENCE: 74

```
aaatctctca ggtcattgct aatctgctaa taattaatat ttacttatgt aataatttct     60
ctgactatat ttgtgttaac tttgcgttga aattcaccat atgcaggaca cttcaactag    120
aatacataga tctctttctg atccactggc ccattgctac taagcctgga aaagttgtgt    180
accccattga agtatcagag atagtggaat ttgacatgaa gggtgtgtgg ggatccatgg    240
aggagtgcca gagacttggc ctcaccaaag ccattggagt cagcaacttc tccatcaaga    300
agcttgaaaa attgctctct tttgctacca tccctcccgc agtgaatcaa gtaattagtt    360
aataattaag ttgatcacac attagtttaa ttacctgact gatccactga tcaaaatcac    420
tgatcgaact aaaccttaat caatccttaa caggtagaag ttaaccttgg gtggcaacaa    480
cagaagctta gagatttctg caaggaaaag ggtattactg taactgcctt ctcacccctg    540
aggaagggtg ctagtagggg tgctaatttt gtgctggaca atgatgtaat caaagaattg    600
gcagatgctc atggcaaga                                                  619
```

<210> SEQ ID NO 75
<211> LENGTH: 978
<212> TYPE: DNA
<213> ORGANISM: Glycine max

<400> SEQUENCE: 75

```
ttgcatgctt ttagtagatg aattacacat aagtaaaaca agtaaaattt atacaagtga     60
ccaggtataa aatgatggcc acttgcaagt tagatatgca tatacataaa gtaaaagtaa    120
actgttttcca gtaaaaactt gtgctcaaaa gaaccaacag tggttcacta aaatcttatt   180
agtccagcat agggcataaa gatgtgtatt aaaccatcac aatatgcaca acattcgccg    240
agaggtttca gatattttga taagctaatt agatgataat aataataatc agatgacact    300
gctcttctgc aatgaaagac ttcatctgag gaatgtgagt tcttgatatt ttaaataata   360
ggagcatata ggatatagca taggcagaga cacgcaaacg gctacagttg ttgatcaatc    420
agattactgg atgtggttct ttaccttcta tccccaggaa tgaatcatta tagccttatt    480
ataggtatct ctcccaatct gacatatatc tcctttccta gggatataaa cagcaaatca    540
aaacctttaa caaaaggaaa gtattcactt acaatgatag caccaacagg gtccatccaa    600
tcatcaacat aatttgccaa aagtgcagca ataaggccaa tgatattagt gatcacatca    660
aaaaagtgat cctgggcata ggctttaatt atctcattgg taaaagaacg acagtaaatc   720
atcagcagga atttcaccaa agtcactgaa agcataatgc ccacaaccca gcgctcttgt    780
tccttggtca gttgaatgc attttcctgg aaatgtcatt acgagacaca ttagaaatac    840
ctagaaaaaa aagagatcct aaatgcaact aaatgaaaat ttaatgtttt agcagtttgg    900
gtgtcagatt tgcctaaaaa aatagagcaa gaatcaactt acagaagata ttaatgtgcg    960
ggtagactcc aagattat                                                  978
```

<210> SEQ ID NO 76
<211> LENGTH: 845
<212> TYPE: DNA
<213> ORGANISM: Glycine max

<400> SEQUENCE: 76

```
ttgcctgcag gcatagtcca tctgaggata ttactagtat tttgtatgat gtgtttgact     60
attttgagga tgtcagggag caaggtggga gggtgtttgt gcactgttgt caagggtgt    120
ctaggtctac ctccttggtc attgcttacc ttatgtggag ggaagggcag agttttgatg    180
atgcttttca gtttgtgaag gcggcgagag ggattgctga tccaaatatg gggtttgctt    240
gccagctgtt gcagtgccag aagagggttc atgctgtccc tcttagccct agctctttgc    300
tgaggatgta tagaattgct ccccattcgc cgtatgatcc tttgcatctt gttccaaaaa    360
tgttggtgga tccttcatta gctgcattgg actccagagg tgcgtttatc gtgcacattc    420
cttcagcaat atatgtttgg gtgggtaaga actgtgaggc caccatggag agggacgcca    480
gagggctgt tggccagatt gtccggtatg agaaggtaca agggcctatt gtgatgatta    540
aggaaggtga ggagcctgtt acttttggg atgcttttc agattttctg cccttaatgg    600
acaaatctgg caaatctggc agtaggatag aagatgaaaa actatttgtt ttgcctggta    660
agaggagagt agatgcatac aatgttgatt acgaagtttt cacaaaagca atcacgggag    720
ggcttcgtgc cttcttttgg ttcattctgg tgaacatgaa acccatttgc ctgcaaggga    780
aaatatttgg agtgtaaggc gtaaagtttc ccattggtac atggaaagag ttgttacggt    840
ccctc                                                                845
```

<210> SEQ ID NO 77
<211> LENGTH: 533
<212> TYPE: DNA

<213> ORGANISM: Glycine max

<400> SEQUENCE: 77

| tcaaaccatg | ttaaactgtc | tattttttctt | ctccctctgt | tcgcacagct | tctaagcatg | 60 |
| gcattcctca | aattggtgcc | aaattgcaag | aatttctggc | tgattttttgg | aatataattt | 120 |
| tacttcggaa | gagggaggag | caacttcaat | aaaaaatact | ttctaatttg | aaattttaac | 180 |
| tccactatttt | tataagtaat | aatcccaaac | attttttcttc | gattttttcaa | tagcaatccc | 240 |
| tcctctttcc | tctactttga | aaattaattc | aactcatccc | agtttagaat | ttgtgattta | 300 |
| aaattttgat | catagaaatt | aggaatatac | agtaaaactt | tatttggggc | taagaaaatg | 360 |
| ataaccagaa | aaggaataaa | acataaaaga | caacaattaa | ttgaaacata | catgtcaata | 420 |
| attagtttaa | taaggacgct | cacagccaca | tccgttgatg | gttttccact | gttattactt | 480 |
| agtctagttg | atgctgtagt | agcattggta | ttcggggaat | aagcctctga | gca | 533 |

<210> SEQ ID NO 78
<211> LENGTH: 645
<212> TYPE: DNA
<213> ORGANISM: Glycine max

<400> SEQUENCE: 78

| aggtaatcct | aatgcatgct | gcttttaact | atgaaacatt | aaattcctat | aagttatatg | 60 |
| cattgcgaag | agttctgtgc | aaatatgcaa | atgaaattgt | atacttcatc | aacaagtata | 120 |
| cagaatacta | cacttgaaga | ttgtataagt | cttagcctat | ggtgttttat | tttgtgtcat | 180 |
| caaatactat | accaaattgg | atcacattat | cagcagaaaa | tcataataca | taagtttaaa | 240 |
| tcccaaaaat | gcaaggtttc | aaagaatgac | tgaacaaaat | caatgagaaa | caacactcca | 300 |
| gcacaatttg | tagacagttg | agcataaact | aataaaaata | tatttcaatt | agtaaagaag | 360 |
| ttgtcaaaac | ctaaccttttt | gcttgatcca | gctatgtcgt | ttgccactgc | gaggacaaag | 420 |
| aagcacttgc | actgaagagt | gcttaaaaaa | tctacgagtc | tcctcatcat | gagttgccat | 480 |
| gacaccatcc | tgaacgtaaa | gtccaagagt | atctcaaaac | taaagctaaa | agggaaaatc | 540 |
| ataaatatta | tatttggatt | aatgaaaaaa | aataacttaa | taatctaagt | ctttcttgaa | 600 |
| ataaagtaaa | aatcagtagt | catacatgag | aaagtgttaa | tgaag | | 645 |

<210> SEQ ID NO 79
<211> LENGTH: 1178
<212> TYPE: DNA
<213> ORGANISM: Glycine max

<400> SEQUENCE: 79

| tctcgggtag | ttgagtctta | gtgagttagt | taatgacaac | taattacagc | tgtcatagct | 60 |
| aacagctttg | tctatataaa | cagatctgta | ctctggagtt | agttgggtta | atgaaactaa | 120 |
| agttttttttc | ctcttttcatt | ttctgttatt | aaaaatcttc | tctcaagatt | ctattaacgg | 180 |
| acatacaagc | actcgtaata | ataaactaag | gaataatatg | gtagaatact | tacatgtaaa | 240 |
| gattaatatg | ttctagcata | tttatttcct | atgacatggc | aatgcctctc | attatttgtc | 300 |
| aaatttgtgc | ttctgggttt | tgattattttt | acactcaact | agcttttcag | tcagtttctt | 360 |
| tcttgaacaa | tttgattata | agcttttgtc | atactcatga | agaaaaaata | agctaatcca | 420 |
| aagatgtact | aatgtgtaac | atgatttcct | tatttgtctt | cttactacag | atacaaacca | 480 |
| agtgaggaga | cattaattca | gatagatctc | ttttgctcaa | ccatgattgc | tgaatgtgat | 540 |
| attaacccaa | ctcagccgtg | gtcactagct | ttgaatcgac | aatctggtgc | atcaaataca | 600 |

| | |
|---|---:|
| tctcctttac ctgtatctac ctttgcctct gagtcccttg taaagtcatt aagttatgtg | 660 |
| cgttccctag ttgctcaaca cattcctaaa cggcttttc aaccagcttc atttgctgga | 720 |
| ccaccttcat cgggacagtc actaccgaca ttgtcatctt tgctgagtaa atccttcaat | 780 |
| tcccaactaa ctcctgcaag tattccagaa acaccaagtt ctgcaagtgt tccaaaaaca | 840 |
| ctagagaagg attcaagtgc tctatctgtt tcaaggttat caaaaatcga aaagctaat | 900 |
| gaaacagatg aactagggtt cattgctcat gatgttctaa atggcgctg gcttgaggaa | 960 |
| ccacagtcat catctatagg gactgaaaag taataatcta tgtttcatgt tggtttaggt | 1020 |
| gtcttggtag tggccactgt agtttatatc tctactttac ctgttagttt tttcccactg | 1080 |
| tagtttcaga aattgacttt gttatttaac attttaatg cagtgatcga gctgtgaatt | 1140 |
| ctcaagacat gacagcacat agtttcttag aaataggt | 1178 |

<210> SEQ ID NO 80
<211> LENGTH: 807
<212> TYPE: DNA
<213> ORGANISM: Glycine max

<400> SEQUENCE: 80

| | |
|---|---:|
| tctacttgta ggagatatag aatctaagat gaaggggcaa ccatggaaat tttttggaac | 60 |
| cgatgatatg ccttacctgg atcagctatt gcagtcttct cctgtaacac caataactaa | 120 |
| ttctgactct gctcgccccc atctgagagc aataacagca tctaaacgca caaaaccggg | 180 |
| ctctcgtcag atttggcatg ttcttatatc aacttgcatt tttgatattt ttcttttct | 240 |
| aattctttta tatttaagtt catgccacaa taaatcttgc ataatttatt tttagccaaa | 300 |
| tgttatataa aaaagttgaa tgatcacctg cattatagtt aataaggtta ttgtgaaatt | 360 |
| aaagtactta caatctaaaa ccaatggttt atagaatatt agattagcct gcaaaagaca | 420 |
| aatgtattac attgtcatgt cctgtaggct tctatgaaaa taaaaataaa ttttagtgta | 480 |
| agaattataa ttatccattg cttttaatga acagaaaatt tcttattgat taattgactg | 540 |
| gggggggagt gctgatcttg ttcttcccac ttcataatat ctttttattc ttcaaagaaa | 600 |
| tagagcaagt aatctttatg cagtagtttg gggttctgtt tggttcatta accactcatt | 660 |
| cccataaaga ctgtagtgtt ccatgaatta tcgtttgttt atatggtcaa aattatgtga | 720 |
| taagtattta tttgctactc tacagtttga tactctctct tggggataaa atgcttgagt | 780 |
| actcttttc gcccaagatg cataaaa | 807 |

<210> SEQ ID NO 81
<211> LENGTH: 1395
<212> TYPE: DNA
<213> ORGANISM: Glycine max

<400> SEQUENCE: 81

| | |
|---|---:|
| acttgcctga gagtgttgtt gcttctgaac aggctgcatg ttcatcacat ttgaaagaaa | 60 |
| ctgttggaaa acctactctt gatgcatctc aacccagccc aactgctact cccagagata | 120 |
| ttgaggcttt tggccgatct ctaagaccaa acattgtttt gaatcataat ttctccttgt | 180 |
| tggatcaagt tcaatctgca agaaacatgg agactgatcc tagtaatcgg gatgtcaaga | 240 |
| gattgaaagt ttctgataat atggtggtgg acaaacagct ggtagattcc aaccatgggc | 300 |
| aacagttgtc atatgggtat gataatgtgg tcaaagatgg tggtcaggt aataattcca | 360 |
| tgccatcatc agatcctaat atgctaagct tttcaacaaa gccacttgat ggacagtaca | 420 |

```
caaatgcatc ttctcaagag gaggttggtt atggtaaaaa aattgctctt aatgttgctg      480
acagtaacaa agcagcctct gttaaaagtg attattctct ggtaaatcct caaatggcac      540
catcatggtt tgagcgatat ggaactttta aaaatggtaa gatgttgcca atgtacaatg      600
cacagaaaat gactgctgct aagataatgg accagccttt cattgtagca aaccaattca      660
gatagtttgc gctttcataa ttcagtagag caaattcaga gtgtcagtga tgctcagcta      720
agtaatgcta gtgaaagtcc aatgcctgct ttagctgcaa ataagcatgc agactctcag      780
ttatcgacac ctgctgttga acctgactta cttattatga gaccgaagaa gcgaaaaagt      840 gcccacatctg aactcatacc atggcataaa gaactgttac agggtctga aaggcttcga       900 gatatcaggt ggttgccaaa actaagtgat ttaatgtgct tattttttcgg tgttgctatt      960 gttggtgtag taaaagatcc catgtctcca gttgatattg tgttgtttca attgttttga     1020
aagaaaacgg tgtgtttcca tagtgtcagt atgactattt taatattgtt ttatgtttat     1080
caatatatca gtatttgtt ttcctataac ttaaatttc ttactatgtg gcagtgtggc      1140
agaattagac tgggctcaaa gtgcaagcag attgattgaa aaggtttgtt tataataaaa     1200
tcagtctacg catgaatcta taattctata atttatgagt tcactttact ctgtataatt     1260
ataattatag gttgaagaca gtgtggaggt agttgaagat ttgccagcag tggtgaagtc     1320
aaaaagaaga cttgtcttgt actactcagc ttatgcagca acaacttagt cctcctccag     1380
ctgcaggcag gcgag                                                     1395

<210> SEQ ID NO 82
<211> LENGTH: 618
<212> TYPE: DNA
<213> ORGANISM: Glycine max

<400> SEQUENCE: 82
atttcttata ctcaaatttt tggtacctct cttttccttca ataaaatttc ttctttttata     60 catgtgtgtg tgtgtgtttg gatgttggta ataaatttct gccagaggat ttgaagatga    120
agagtccata agtttgttga ttacttgata caatctaata gagtatttta accggcccat    180 ttttttttctt gggctaaagt gatgtaacat ctaacaagtg ttgaggagat aaaacatttt    240
caaggagttt gattgttgga tatctagagc aattgtaggg ttttattgta ttcatgatgc    300
ttcttaatca ttcaaattgt ttgtgccttt tcatgttata gctttgtgaa gaggagttac    360
tcaaggaaga agcgctttta gtaaaaaaac aacttatttc ctttagtttt attaatgact    420
tgtatgcaga ttggacaaca ctttagggat ggctacttgc ataaagaaga atttaagata    480
gtttatgttg ctccaatgaa ggtatgttga tgctttttgtt tttctttaca tttctctatt    540
cagatttgct ttttgttccc tgcatttgtg tgccattact catttctaag tatagattct    600
tgtcctttcc aggctttg                                                 618

<210> SEQ ID NO 83
<211> LENGTH: 1085
<212> TYPE: DNA
<213> ORGANISM: Glycine max

<400> SEQUENCE: 83 tcttcgcca gcttgctgcc tgcagtaaga tccaaccttt atggtgggat tctatgtcct      60
ggataaatct caaaggtgct atgcctttga gtacaaaaca gctgttcatg cagtactcct    120
ttttgcaaga agatggtaga aggaatagga ggtggcaata ctggtggttg gctatcactt    180
ggtctacttg gcagcttcga aaccgaattc tgttctctgg agcgactttt gatggaaaca    240
```

```
aattggttga agacgccact ttcttaatgt ggacttggct tcataatttg gagaaggatt      300
ttactattca tttcaatcac tggtccagta acttcaaaca tcattttttg cagtagtagg      360
ggtgtttttt gggttcatat cacatgtatt ttcttcccat attttggttc ctaatcagac      420
ttatgttgcc tgattgagga accatattta tggtgtctaa ctctgtattt agtacctctg      480
gtacttttct aatatatata tagttttatc tttgctgatc aaaaaaaaaa aagtactcat      540
ttgtctattc ctgtaaagtg gcaaggaaat aatcagtagc tttaaaatca tctgatgtgt      600
ggatgtgaca caaattacaa cataaatcat gttaaggata tgaaaagtat gtactcatta      660
gtctcttcca tcaactaagc aaagcaacat ggaaatcatc tgtagctgag agtgactatt      720
aaattgtaag atttggaggt catggacctc atgtttatag ggacagtaaa attatccaat      780
tacccaaacc tttagacaat ctgaaatgca cacataaat ggtacaacag ttctaaatgg      840
ggcaggtaag tagcattcat tgctcaatat gtctataatt caagaatgaa gctttacatt      900
tagtgcatat ttggacctca gattggctta ttttgcttt aagaaaagct tatgatcaaa      960
atgttcaata aaaaacttaa agcttctttt tttttttcag tgtaaaatag tcagaaattc     1020
agaaccagat tgcacttagc cagttgtata taaaactatc caatggccat aaagaagaca     1080
gatca                                                                 1085
```

<210> SEQ ID NO 84
<211> LENGTH: 1052
<212> TYPE: DNA
<213> ORGANISM: Glycine max

<400> SEQUENCE: 84

```
aagttcactc ttaactaatg ttttttcact gtattcccta gctatatttc agactggtgt       60
gtgacagtct tttttgttc atagatattg cggaagcttg aagaacgtgg ggctgaccta      120
gaccgcttgt atgagatgga ggaaaaagac attggggcat taattcgtta tgcgcctgga      180
ggaagggtat gcaactttta ctagaatgat tttcgaagat ttccatcaga ggttggttcg      240
gatgttgaag aaatgctgat taatgttttc ttatcccttc ccctttttag ttggtcaagc      300
aacacctagg gtatttttcca tcacttcagt tatcagcaac tgtgagtcca attaccagaa      360
ctgtgttgaa ggtatttcat gatgaagatt ttttttccca gactgctcag ttgacatttt      420
ttcattgatt tcatcacatc aaaaagcctt gatacctaat tctgcatcac cactcattat      480
tttcaggttg atctggtcat tacgcctgtt ttcatttgga agatcgtttt tcatggtact      540
gctcaacgtt ggtggatttt ggtagaggtg aataaatttt catgtgatga ttggtcacat      600
tgtaaattcc ttggtttttg ttaaaaactc tgatctcttg ttataaaagg agaaatttat      660
caagatgaag agaaagactt tcaaagagaa aggaggatga ggaatcctcc taaacaaagg      720
aacaaaacag aaaacaacta ggaagaaaga gataatcaga gaaacaaatc ttcccagttg      780
ctcgatataa cttcagtga aaatgctaaa gaaacccct ttaaagcaaa tagatactga      840
gcacctgatc ttataccaaa tcatgtgacg tgctaaagaa acctccttta aaaatactag      900
aacagcttgt agcatatgta gcagatttat acaaaaaatt agcttcttta cttctgtcaa      960
aaccttgaaa accaatcatc gataattgtt tttgagactt aggacacacc caacattaac     1020
tgaaaatgct gaataagtaa tgccagggag gg                                   1052
```

<210> SEQ ID NO 85
<211> LENGTH: 855
<212> TYPE: DNA

<213> ORGANISM: Glycine max

<400> SEQUENCE: 85

```
tagaattaca ggtctggaga agtatctgaa gactgtagat tcggtgcggg attggattct      60
gtttcatata tacttttta acaacataag ttaattttc atatagtttt ttatttaatt       120
ttataaatat tttgaataaa accaaaaata tatgtaagtc gttcgtacat aagacgcgtt     180
aaacgtcagt acttaataat aataatatag tgtaagaaac tcaactgggg aagtgcataa    240
aaaaataaaa gtataaatac aagaaaaatg aactaagaaa gtgtgtactt atgtgctaat    300
tagcaagatc gttggaacaa aaagccaaat tgactggtac tttctcgtta atttcttcaa   360
ttttcattgt ttcgttaaat actagtggca tgtccgtcaa aagtcaaaag ccacatattg   420
atgaaattgt gttgttagaa taattaatta attacttgca gagcaaatct cctccacaat   480
ttttcttttt ttctctaccc aagagacttc ctttcaactc agatactctt tgattctctt   540
caggaaaaca tcaactaatt aaaatctaat tttgtctttg atactctttg tccgcggaat   600
tcaccacccc caccttctca atttgttttgc tttctgcttt cttacctctt ttttctcaga   660
tttcatttgg ttgatccttt cttcaattct tcttctgggt ttgtagttgt ttttttatct   720
gacttgtgtt tctaaaatcc atgaaccgta tgtgatttcc agtgtctttt tcttttttcca   780
gattcccaga gagaaaaag aaaaaatcct tttgtttgtg tgagactgta aggatcaatt    840
ggttgagttc tccta                                                      855
```

<210> SEQ ID NO 86
<211> LENGTH: 1066
<212> TYPE: DNA
<213> ORGANISM: Glycine max

<400> SEQUENCE: 86

```
gtatggggcg attcaggagg tggaatctgc aatacaagag cttgaaggga caatgagggg    60
gaatgtaatg ttgacagaaa ctgttggacc tgaacacata gccgaggttg ttagccgttg   120
gactggtata cctgtgacaa ggcttggcca aaacgataaa gaaaggttga ttggtcttgc   180
tgacagattg caccagagag ttgtggggca agaccaagca gttaatgctg ttgctgaagc   240
tgtgctgaga tcaagagctg ggcttggaag acctcagcaa ccaactggtt ccttcttgtt   300
cttgggtcca actggtgttg gcaagactga gcttcaaaag gcacttgctg agcaactctt   360
cgatgacgaa atcaattggt gagaattga catgtctgaa tacatggaac aacactctgt   420
ttcgcggttg attggtgcac caccagggtg tgtggattga cattttcaca tttcagttta   480
ttgttagttt tctgtatgaa ctacagataa ctgactcatt gtttcgactt tcaggtatgt   540
tggacatgaa gaaggaggtc aactaactga agctataagg cggaggcctt atagtgtggt   600
actctttgat gaagtggaaa aggcacacac atctgtgttt aacactctcc ttcaagtctt    660
ggatgatggg aggttaactg atggccaagg ccgtactgtg gacttccgaa acactgtcat   720
tatcatgacc tccaaccttg gtgcagagca tctcctcact ggactttcag gaaaatcttc   780
aatgcaagta gcccgtgata gagtgatgca agaggtatgt ctcttgacac catttgttta    840
atatgtatga caaggtctt tgtgctgtgt tttgacttgt gaccttgtct gttgaatttg     900
ttgtaacagg tgaggaggca ttttaggcca gagttgttga accggctcga tgaaattgtt    960
gtatttgatc ctctttcaca cgagcaacta aggaaggtca caaggttaca aatgaaggac  1020
gttgctagtc gtcttgctga gagaggaata gccattggca gtgacc                  1066
```

<210> SEQ ID NO 87
<211> LENGTH: 890
<212> TYPE: DNA
<213> ORGANISM: Glycine max
<220> FEATURE:
<221> NAME/KEY: unsure
<222> LOCATION: (719)..(719)
<223> OTHER INFORMATION: n = a, t, g, or c
<220> FEATURE:
<221> NAME/KEY: unsure
<222> LOCATION: (1)..(890)
<223> OTHER INFORMATION: unsure at all n locations

<400> SEQUENCE: 87

```
attatgaagt atgtgacaga attgtgtttt caatatattt ctgacaatta gggattgcac      60
gggaaaatga acagcgacca gagaagttat ccttaaagaa gcaattgaag cggaaatgtc     120
tagaacaaaa tcccaatctt gtccaaaacc cagttatgtg tggatatgga gtgggtgctg     180
ccagtaacca gcccatggaa atcttgaact gtagccaacc aagtgagaac ttgcttatat     240
attaactttc tgaggaatac aataaaaaaa aattatttttt ccttgaagtg atatgttttt     300
tcctgtcata cttggtatat tggatttagg aagtccctca aatgtatatc acagcttata     360
ttacatgctc tcttgtggta atgcattttc ttggtcttaa agattttggc cattttagta     420
gataatgtca aggtagtgag atttgagaat tagtgctctt agctgtactc acattagtgt     480
tggaacctgt tcttcctact tgtttatgtt tattgagaca ggtaccatgg cttgtggcaa     540
ggtgatattt tctaatggta tataaatata acctataaaa atgtagaccc tttatgagcc     600
tggaggatca agaatggaaa atggaattt ggtttattac attcatagg gcgaaatgaa       660
atatgctgca tcatgattac cggcagacta aatcccaata atcatccttt ttttctgana     720
ggaatggtcc cgcccagtta ggaaaaaact acaggtatct tttgaccgtt tgtggaagct     780
ctatgagtcg gttaaaccgc taactctatt cttttatatg caaggtgtct tcttttcga     840
gtaaacaaat caaatctctt aaaaaaaagc tccggataac ttatgtttca                890
```

<210> SEQ ID NO 88
<211> LENGTH: 640
<212> TYPE: DNA
<213> ORGANISM: Glycine max

<400> SEQUENCE: 88

```
aataaatgtc atggactatg atatacctga gcttgttgtt tttattcaag aggaacatca      60
gcaatttgtc aaggatactt gcattggtaa gggagtgtca ccagaaggca agtgtatgtc     120
agaagattgt gcagtaaatc atgatccaat gtcatgtcac tttgagaatg acttgaaccc     180
ccgaagagat tcaaatctaa gaactatgga agcaatgtca atcaattcaa atgggccaga     240
gtttgaatct aaacctctta cccttaagga tgccatggaa ttttatgatt caagaggttt     300
agtgatggat ggtgaagagg attcaggata caatatttca attgaccacc tcacaaagaa     360
gacaatacca gagaccatta gagggtgag acactttaat ctcatccttg tgcattttac      420
gtctttggac gaggagttaa ttgttttta gaatattgcc actaagacat taatacttat      480
attctaagca atataaaata tactgtggac tcgtcttctc ttttagcatg gttggtgaaa     540
cccctacat caatgtacat cttctcttt gtttcatatg cttgattgta tgattgataa       600
aagattgaaa caagacttaa taatcatata gggagttacc                           640
```

<210> SEQ ID NO 89
<211> LENGTH: 993
<212> TYPE: DNA

<213> ORGANISM: Glycine max

<400> SEQUENCE: 89

```
atcattttca aagagtgtat attttttttt tttaaatcgc tgagttccta aatataatcc      60
aaacactgaa ttgaggagtc aagtgctgtg tgtgtaagac attgcaaaat aagttaccac     120
aaattcaccg aagtttcata gatattgtct tattgttatt tgatcctgaa acatgctagc     180
aggattaata aaaagaataa aaatgttacc agctgcacta gtatagtttt gatcctgtca     240
tcctttctag caatggttcc attccttgaa tacacttcat ctgaatgacc aatttttattc    300
ttggcacctt cattcttttc aatggaatca atgttggtgg agctcacacc actggaatac    360
acttcacccg aatgaccaat tttattcttg gaaccttcat tcttttcaat ggaatcaatg    420
ttggtggagc tcacaacact tgaatacact tcacccaaat gaccaatttt attcttggca    480
ccttcatttt tttcaatgca atcaatgttg atagagctca caacacttga agtcagctcc    540
atgatctgct cagactttgt tcctttgtca tcaattgcat cctcagtagt tgtctctggc    600
atatcttcat aagtagagag tttgacagaa tcgctgaaag aaactctttt aattttttggc   660
gttattgggc tttctaactt agaaacatct gattcaacca ttgacataga aaatctttgt    720
atcggaccag gttggataaa aaatttcta cccctttgacc aaattttgtt agagtagtct    780
ttggttgtcc tccatctctt cagtttcgtg ctgccactgc tactttggct actggaagag    840
cctttaaagg tattaagttt caattcatcc gtttcgctcg atgtggaatt tggagagacc    900
ctctcaagct ccagaacaga atttggagcc tgcctttttc ccccaagatc cttgggtgga    960
tgttgccccc aaagctatct cttactgaag gaa                                 993
```

<210> SEQ ID NO 90
<211> LENGTH: 804
<212> TYPE: DNA
<213> ORGANISM: Glycine max

<400> SEQUENCE: 90

```
caagcttgca tgcctgcagt aaatatgcca tcaatatgag caagtgagca acagcctaaa     60
aattgttgga atgtttatgg ttagagattt aattggtttg catgattttg gtatttctat    120
ttattcataa tttggagaca cggatcatat aactttagga tttagatcaa gtagagtggt    180
tttaaaataa atcaggaatt gaatttaatt agttgtagat caaatttagt tggggttctt    240
gcactagtaa agttatgatt cttatggttt tcagtaggag ctaatcctgt attttgaatt    300
tacttatata gaatttgatc atttcagaat gatctgttag gttcatttta ccaccccta    360
cataccattt tttatcttca catctaaatt cttcttcctc tttggcgcat atcaacagga    420
cagacaaaat aaaatttaac ctgccttttt tagaagataa gttttgaggg ctattaatag    480
tactctcaac ggttatgctt tgacttagt tgaacatttg ttcattgctt ttgattggct    540
cccccagtct tctcaatagc agtatcatca tcaacacaat cattctcctc tgccactacc    600
aactagtgct gagactactc ctaactctcc ttcgccaact ccatttcctc cgactttgtt    660
tccacttgat gatctcccca ttgaacttca taaaaatata tgttccactc aatacatctc    720
attatgttac cttaacccta acctatcatt gtttgtctct ttcctattat gctagtcttt    780
tgtgtttgat cctgtcatcc tgag                                           804
```

<210> SEQ ID NO 91
<211> LENGTH: 749
<212> TYPE: DNA
<213> ORGANISM: Glycine max

<400> SEQUENCE: 91

```
tggcgcacca gaatggggac tgccgtccac agttccaatg atgacacttt acagtccata    60
tcattcaaat tttgttggac cttcatatca tcatccagga gctgaatcta ttaatcagat   120
gtggtcgacg aatgctcatc acttgcaggc gatccctaat tataattatc ctcatcctta   180
tagttatacc tatgattata attatacagc tcccgttgtt caccattacc atgtccctcc   240
tgcgccattg tttcataact ctttggttca aaattctgtg ggagatgaaa ataatggagc   300
aactaccaat agtactgttg ctacaatttc agatgaagct agagaggaaa ttctggtgaa   360
atttcgaaac tttaaacaat ttgacgttgt tgaagacgtt tcagaccatc actttgttaa   420
tgccgactct tccatgcaac aggtagcctt ttaatgcaat tttttttcttc cagttttaat   480
cttaattatt taggtttaca tacagtcaat ttatttcatg aacagcattc aaagaattgg   540
gctaaaagaa tccagggaga gtggaagtca ttggagaagg atttaccagg tgagagttag   600
ttcgattagt attcatgtca taaattggct aaaatatttt ccttatctat ccaacttttt   660
gtatttaatt aaattgattt cttttacaag ccaatggatt tggactggat gaattggatt   720
cccaatttgg cattaaatat gctaaaggg                                      749
```

<210> SEQ ID NO 92
<211> LENGTH: 685
<212> TYPE: DNA
<213> ORGANISM: Glycine max

<400> SEQUENCE: 92

```
acccttcaga actgaatatt gctaacacac aaggcaacaa ccaaacttac acgacaaaca    60
tccacactaa aactgaaaaa cacaccttct gcttgttca tcccgaagtt tggcatcaaa    120
ttctttgcta ggaggatact ttggcaaact tgaaggatca caaggtagag gctttgttgt   180
aaagaactaa atagcaagca aaccaaaagg agacagtcat gacatgcata ttgaagtatc   240
agcaacaata atttacatcc aaaataaaat agaaattaaa gcaacaatgc agttgagtaa   300
gagataatga ataaatacac acgaatatgc gataacatat caggatatat aagtgaggac   360
ttgcaataat agtaacaata agaattttct actatattac attcttggag caatacagg    420
ttaggacttg caacaatagc aacaataaag agacaacaaa ggagcatcaa tttgattaaa   480
gcaaaggaa acatgcaca aaaatgacaa aaaattccaa ggttgtcata ttttggagaa    540
tacacaacct aagtttgaaa tataatttaa tccaactctt tttaccaaca tgaacatcca   600
ctcttcgtta tgtgtactga ctgatattat aaaatgtact caagtagtct gaaaaattca   660
tcatgaattt catacctcac tcttc                                         685
```

<210> SEQ ID NO 93
<211> LENGTH: 652
<212> TYPE: DNA
<213> ORGANISM: Glycine max

<400> SEQUENCE: 93

```
attgtgattt tcactggttt gtgagagtgc aaaagaattg ttcagttgaa tgtgcaaaat    60
tgcttggatc agttgaaatg cacctatgaa tttgtatttt tcttttttat gacaaagggc   120
atgtagaata tgattatatt ttgtttgaat agtgtggggg agcattactg ttttttttt    180
tttgaaaaaa aaaatctgat gtggtagtgg tgtctgattc acatgtggaa aattcttatg   240
gattgggaaa gaatattgat tgtttccttt tctcacagtg ctggtggtga aagcagtgga   300
```

| | |
|---|---|
| ttccttgcat tcagagttca gggctgtgga taatttggtt gtgtgcaata ccaaccgtgt | 360 |
| ccttaaagct ttccagaatg ctcgagttgg atcccatgta agcattcccc ttgatttata | 420 |
| taacctttat gcaaatgtac atttaatatg atgctcaatg ctcaagggtt caaggctaat | 480 |
| aaacttgtta actgttttga ttgtaattgg tagagatgtc ctttaagcca tgggctgat | 540 |
| cttgatgcct ttatgtattt tgacattttt accaaaaaca taactaatat aggaacccaa | 600 |
| aaacttagga ttcgattagg gagaacctaa ggctgcccat aaaacttga gc | 652 |

<210> SEQ ID NO 94
<211> LENGTH: 821
<212> TYPE: DNA
<213> ORGANISM: Glycine max
<220> FEATURE:
<221> NAME/KEY: unsure
<222> LOCATION: (798)..(798)
<223> OTHER INFORMATION: n = a, t, c, or g
<220> FEATURE:
<221> NAME/KEY: unsure
<222> LOCATION: (1)..(821)
<223> OTHER INFORMATION: unsure at all n locations

<400> SEQUENCE: 94

| | |
|---|---|
| attccataac ggtttgcaac tcttgaagat cgtgactctg gtcgtgtcac tcctgcgtat | 60 |
| cgcgcctggg agcaacaaga ttagttgttc ctctcatggc ttcaatccac cgtttctgct | 120 |
| cccattcttc gaaatttcat cggctgcact agtttgtggc ttctctagga caaaatccac | 180 |
| aactattttc atgctcatac aaatgcaaag gcacggccac ttcgtacaga gctgcatcaa | 240 |
| ctcactcttg aaggtcgtac tatttctgat tatttgactg agattcagaa tcttgttgat | 300 |
| tcttttactg ctattggtga tccaatttct atttgcgaac atgttgacat tattattgaa | 360 |
| gaatgtgtac cagaaaacta tgagtcctct gtttcgcaca tcaataatag atctgaacct | 420 |
| ctcactattg atgaaatcaa aactgttctt ctcggtcatg aggctcagat tgacaaattc | 480 |
| aggaagaagg cagtggtttc ggttaatgtt gcttccacat ccactgtgtc ttctgtgact | 540 |
| aatccatctc atgctaattt tggaggtttc agaatcagaa tcagagtcag tataaaaaca | 600 |
| gaggacgtag cagtattcag tgttacatct gtcagaagtt tggtcatgat gttgccaact | 660 |
| gctggcacag gccctcaact tcctatgctc tgctccttat cctatgttgg cacaatttcc | 720 |
| caccatgcct cagcttttat tcaatttctt tggagctgct ctgcatttcc ctcttatctg | 780 |
| tttatgcagg ctcctgtntc tcaacaatgc cagcagccac t | 821 |

<210> SEQ ID NO 95
<211> LENGTH: 738
<212> TYPE: DNA
<213> ORGANISM: Glycine max

<400> SEQUENCE: 95

| | |
|---|---|
| ctctagagtc gaccctgcag ttattatagt gacagaagag gaaaagtcac cacgactcat | 60 |
| atgtaaaaga aaagatagaa aatgatgaaa ggacaaggga aaaacactac actaattaag | 120 |
| tcaatttcat tacatcatta gaaaaggaca tgagggggga aagaaaatg ttgtgaggca | 180 |
| atttacatgg gtatttgagg tgggaacata atctttagta cataccaaat ttctgtgtat | 240 |
| acattatagc atgtcccttt tttttttttt ctattctcaa gttgaattgg acagtaatag | 300 |
| attaatgttg taggatgcca agcacacaaa cattgagaat atattgatct ggctggaga | 360 |
| tcatctatac cgaatggatt acatggacct tgtgcagtta aacatgttaa ttttttgtat | 420 |
| cagagctgtg taattatcaa gacaattaag gcaattatat taggctttaa gttcttctca | 480 |

```
ctacttgtta ttgaaattta ttactaattg tattctatga atattttca tcattcacaa        540 aatcaaggca attaattaac acaaaaaaaa ctagttctat gtttcttttc tcttacccctt      600 cttatgttca tacaccaagt cttttgaata attttttgcca aaggttccaa agttttaga       660 cacaccgagt tcatacatgg agtgtttctt aattttattt tcacaatttt tgctgattat      720
ctatctttta taattaat                                                    738
```

<210> SEQ ID NO 96
<211> LENGTH: 710
<212> TYPE: DNA
<213> ORGANISM: Glycine max

<400> SEQUENCE: 96

```
tgtgatgctg tcaagagtgt tgtctacaaa ttttgcaaac cgagatacta gatgcctcaa        60
aattaagata ttaatttcag caataggtaa tgaataattt cttatggatg acagtctaga       120
ttcctctctc aaaggagaaa tcttctaaac aaactcattt taactcttga aattgtaagt       180
attaattacg ttaatctttt tattaattac tttaatattg tccctttttt gtgaatactt       240
atttataaaa cagacaacaa aaataagaat tttgtgaagt caaagattaa atgattggt       300 gcatagactc taaagcaaat gggagtttac tcaaaatgtt tttcttttc aattggtcta       360 tatagtgaca tactatttta gtggccacta gattgtcatg agagtggaca taaaatggac       420
caaatcagcc atatcaggta tgtgggaagc gcactcatat agctaagtgc attgtttcca       480
catgaaattt cttactcttt tgagactcaa aagtacctat cttagctaa tgcctgcatg       540 aaatgcgggc atatatgcac atgggtcctt tcagattata atgtggtaga agttagaact       600
agaaccagaa gctatactaa ccttggtaat tcgacaaaaa actaccaggt cgcgagagag       660
gttctggctg gggctttctt ctccttctat tgtgtccatc taaacgtttt                 710
```

<210> SEQ ID NO 97
<211> LENGTH: 954
<212> TYPE: DNA
<213> ORGANISM: Glycine max

<400> SEQUENCE: 97

```
agtcgacctg caggaaaagt tgtaaataag gtaattaaat gctacaatat aatgattgac        60
aaaaacatta tctgtttagg aacaaatgga ttatatttta tgagacttaa acattgatga       120
aaaaaatggt caagcatcaa aagttgttat cagtcaatat ctctgtcaat aaatatccag       180
gacaagagtt gtgagccaac aatgaccatt cgttttgtaa tctgttatta tagcatatta       240
ttttgccctc tctataagag ggattaactc tttgactgaa atacagaga aatattttac        300 aagccataaa tgcatttatt tggcctaaaa aacttaacac tttcttttg gccatacttg       360 tccgtgaaaa acgaaatttg ttggaatttt tcagggccaa aactgaaaat taaaattaa        420 attgaaaaaa tgaaaatagc agataaaacg atttgaatga aagtaaaaat ttgtgaggga       480
attagagaat gttgagtaga gtgaaaatgg atcacgtacc gaataggaat gaggaacaag       540
agagagctcc gagaataacg aggatcccctt cgccaagaaa cccttcaggc ttcagccttc       600
accgagaagc cgatcgagga acaggaaccc tagctgtcgt gaacgagaga gagtccgcag       660
tgcagttcac tgaatattca gctcacaact ttttttcccc gaaacgggtc gggtcgaacc       720
aaaccggtta caaacggag cggttttaa cccgtttcac tgaatattcg gttcactgaa        780
tttgattagt ttgatcccta aaattaaga ttaaattaat cactagtaat aattgtacca       840
```

```
aacttgacag acacacaccc tatcagtaag agctagtcta cctcggccta gaatacagac      900
taattaccca aaggttccag agaacaaatg aagtactgca ggcatgcaag ctgg            954
```

<210> SEQ ID NO 98
<211> LENGTH: 730
<212> TYPE: DNA
<213> ORGANISM: Glycine max

<400> SEQUENCE: 98

```
ttttattttc aaattcttct tgttacaaaa acttttaac ttttgatgg gtaaaatgta         60 caaataaacc attaattttg agcacttatt gatccttcac gaggttttct tctaaataaa      120
gttatacaca ggtatggatc gttgtatgca agaccacttc ttgagaagct tagggaagat      180
ggtgtataca tgaggcctct gggtaatgtc atttatctgt tgtgtggacc ctgcacatct      240
ccagaagttt gcaatcaact actcgtcaaa cttcttaggc ggcttgaaga atttgacgta      300
tgtaagaatt gaagtggatg aagtggataa gtctaatatt cctgctatgg attttggcta      360
agtttattgc tactattatt ttttgtgggg gaggaggaag gggcatgaat tgtaaatcca      420
agggttgcaa ttagcttggt ttttttcaa ttcagttgat gtattttatt tataaataaa       480
aaatgtatct tatttcaatt cccaccctcc ccccattttt aagatgttat taataaaaat      540
gttaaagtat ttaatcattt tctttcaata ttttggaaa aaaatcaag ttatgtaatt        600 aaaaatatat attaactgga aacaaaacca gaataaatta aatagtcaat aggtctagta      660
acaattgaat agagtgtgag taattgtaaa ttttggaaa taatttttta attttatggg       720
ataaaaaaat                                                             730
```

<210> SEQ ID NO 99
<211> LENGTH: 1061
<212> TYPE: DNA
<213> ORGANISM: Glycine max

<400> SEQUENCE: 99

```
agcagagtgc aacaaataga aagggaaaa catccatttc aatagaaaga aaggttgagc        60
tgcaaattgt tgattaccaa tgcaatgggc ttcttccatc attatcagga acatcagggt      120
cagcattcca ttttgaaaca acgtggtaaa ggaaagctgt ctgaccatat tgtgcagcaa      180
catgcgttgt ctgtgtccaa gcaaatcata attagtaaaa ttaacattta cagccacacg      240
cttgtgcttc aagtaaaaca gaatcccaa actaccaaat tagcagatgt aaccagaaat       300
agacagccag gtataagaga tacataacat gctccaaatg ccttacccca gcaatctctt      360
gaataaaggg aaaatgaatc acagcaatct aacctgatat ccattcatat cggcagcact      420
cactcgagca ccctcctgga gtaaaagttc cgcaacctga atagcacccc gaaccgcact      480
ccaatgtaag gctgtctggc cagtatgatc cgttgcattt acatctcccc catgctgcca      540
accacaaatc aaccagttaa tttaggataa gactaattcc atacttaata tcaagccaaa      600
tttggctaca tacattcaat tgcaaaacaa acaaacacca cattcgattt ccatttccat      660
aacacaaaca tgacctacaa gccaacctga gctgagctga gctgagctga gctgagctaa      720
gctactttaa caaattcaaa ccaccaaaaa catcataatc aaatgttctt ctcttctaca      780
tctatatcat tccttcctta aacagcaata agtaactaat tcttacattt tcttttcttg      840
gagtaaaaaa atagtaattc agcgagtgcc aaaataacat acgcattcaa acaagcacaa      900
taaaagcaaa gtaagcaaag caaacacaat tcaacaaacc gatcaaagaa cctcaatgat      960
gtactgagca gcggcagtgc gattgttgag agcagcccac tgaagcgcgt agtatcccaa    1020
```
cccgtcgggc tcggtgacgg ggcaaccctc ttgctccacc a    1061

<210> SEQ ID NO 100
<211> LENGTH: 13
<212> TYPE: DNA
<213> ORGANISM: Artificial Sequence
<220> FEATURE:
<223> OTHER INFORMATION: Description of artificial sequence: synthetic
      probe

<400> SEQUENCE: 100
tctgggaggc agc    13

<210> SEQ ID NO 101
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 101
tgggagacag cctt    14

<210> SEQ ID NO 102
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 102
ctcgttcccc atgaa    15

<210> SEQ ID NO 103
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 103
aagctcgttc tccatg    16

<210> SEQ ID NO 104
<211> LENGTH: 21
<212> TYPE: DNA
<213> ORGANISM: Artificial Sequence
<220> FEATURE:
<223> OTHER INFORMATION: Description of artificial sequence: synthetic
      probe

<400> SEQUENCE: 104
agatgtaaac ttgttataaa g    21

<210> SEQ ID NO 105
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 105
ttgttatgaa gtgattttta                                             19

<210> SEQ ID NO 106
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 106
tttggaggaa atatg                                                  15

<210> SEQ ID NO 107
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 107
tttttggagg aagtatg                                                17

<210> SEQ ID NO 108
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 108
ctcactctca atatc                                                  15

<210> SEQ ID NO 109
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 109
cactctcaag atcac                                                  15

<210> SEQ ID NO 110
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 110
agtggtccct taaat                                                  15

<210> SEQ ID NO 111
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 111
agtggtccct caaat                                                  15

```
<210> SEQ ID NO 112
<211> LENGTH: 13
<212> TYPE: DNA
<213> ORGANISM: Artificial Sequence
<220> FEATURE:
<223> OTHER INFORMATION: Description of artificial sequence: synthetic
      probe

<400> SEQUENCE: 112
aaggtcgaaa att                                                          13

<210> SEQ ID NO 113
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 113
aggtcgagaa ttgt                                                         14

<210> SEQ ID NO 114
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 114
cagtcaggta attaaa                                                       16

<210> SEQ ID NO 115
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 115
cagtcacgta attaa                                                        15

<210> SEQ ID NO 116
<211> LENGTH: 13
<212> TYPE: DNA
<213> ORGANISM: Artificial Sequence
<220> FEATURE:
<223> OTHER INFORMATION: Description of artificial sequence: synthetic
      probe

<400> SEQUENCE: 116
actgcccttc tgc                                                          13

<210> SEQ ID NO 117
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 117
acactgctct tctg                                                         14
```

```
<210> SEQ ID NO 118
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 118
aggtgaagag cctgtt                                                     16

<210> SEQ ID NO 119
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 119
aggtgaggag cctgt                                                      15

<210> SEQ ID NO 120
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 120
tttcaataac aatccc                                                     16

<210> SEQ ID NO 121
<211> LENGTH: 13
<212> TYPE: DNA
<213> ORGANISM: Artificial Sequence
<220> FEATURE:
<223> OTHER INFORMATION: Description of artificial sequence: synthetic
      probe

<400> SEQUENCE: 121
caatagcaat ccc                                                        13

<210> SEQ ID NO 122
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 122
tgcacataac tcttc                                                      15

<210> SEQ ID NO 123
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 123
tgcacagaac tctt                                                       14
```

```
<210> SEQ ID NO 124
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 124
tggttgagca aaag                                                        14

<210> SEQ ID NO 125
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 125
tggttgaaca aaag                                                        14

<210> SEQ ID NO 126
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 126
ttgtaagtac tttaatttc                                                   19

<210> SEQ ID NO 127
<211> LENGTH: 18
<212> TYPE: DNA
<213> ORGANISM: Artificial Sequence
<220> FEATURE:
<223> OTHER INFORMATION: Description of artificial sequence: synthetic
      probe

<400> SEQUENCE: 127
agattgtaag cactttaa                                                    18

<210> SEQ ID NO 128
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 128
aatgtgatca aagatg                                                      16

<210> SEQ ID NO 129
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 129
aatgtggtca aagat                                                       15

<210> SEQ ID NO 130
```

```
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 130
cacacatgta tataagaag                                                  19

<210> SEQ ID NO 131
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 131
cacacatgta taaaaga                                                    17

<210> SEQ ID NO 132
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 132
cacatcctca catcag                                                     16

<210> SEQ ID NO 133
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 133
acatccacac atcag                                                      15

<210> SEQ ID NO 134
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 134
ctctgatgga atcat                                                      15

<210> SEQ ID NO 135
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 135
tgatggaaat cttc                                                       14

<210> SEQ ID NO 136
<211> LENGTH: 17
```

```
<212> TYPE: DNA
<213> ORGANISM: Artificial Sequence
<220> FEATURE:
<223> OTHER INFORMATION: Description of artificial sequence: synthetic
      probe

<400> SEQUENCE: 136
cttccccatt tgagttt                                                      17

<210> SEQ ID NO 137
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 137
ttccccagtt gagttt                                                       16

<210> SEQ ID NO 138
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 138
ttgtcacggg tatac                                                        15

<210> SEQ ID NO 139
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 139
tgtcacaggt atacca                                                       16

<210> SEQ ID NO 140
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 140
tctactcaaa tggcc                                                        15

<210> SEQ ID NO 141
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 141
attatctact aaaatggcc                                                    19

<210> SEQ ID NO 142
<211> LENGTH: 16
<212> TYPE: DNA
```

<213> ORGANISM: Artificial Sequence
<220> FEATURE:
<223> OTHER INFORMATION: Description of artificial sequence: synthetic probe

<400> SEQUENCE: 142
ccagagtatg aatcta                    16

<210> SEQ ID NO 143
<211> LENGTH: 16
<212> TYPE: DNA
<213> ORGANISM: Artificial Sequence
<220> FEATURE:
<223> OTHER INFORMATION: Description of artificial sequence: synthetic probe

<400> SEQUENCE: 143
ccagagtttg aatcta                    16

<210> SEQ ID NO 144
<211> LENGTH: 18
<212> TYPE: DNA
<213> ORGANISM: Artificial Sequence
<220> FEATURE:
<223> OTHER INFORMATION: Description of artificial sequence: synthetic probe

<400> SEQUENCE: 144
tcaatgaaat caatgttg                  18

<210> SEQ ID NO 145
<211> LENGTH: 16
<212> TYPE: DNA
<213> ORGANISM: Artificial Sequence
<220> FEATURE:
<223> OTHER INFORMATION: Description of artificial sequence: synthetic probe

<400> SEQUENCE: 145
ttcaatggaa tcaatg                    16

<210> SEQ ID NO 146
<211> LENGTH: 16
<212> TYPE: DNA
<213> ORGANISM: Artificial Sequence
<220> FEATURE:
<223> OTHER INFORMATION: Description of artificial sequence: synthetic probe

<400> SEQUENCE: 146
aaggcaggtt aaattt                    16

<210> SEQ ID NO 147
<211> LENGTH: 16
<212> TYPE: DNA
<213> ORGANISM: Artificial Sequence
<220> FEATURE:
<223> OTHER INFORMATION: Description of artificial sequence: synthetic probe

<400> SEQUENCE: 147
aaaaggcagg ctaaat                    16

<210> SEQ ID NO 148
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 148
cagctcccgt tgtt                                                        14

<210> SEQ ID NO 149
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 149
agctcctgtt gttca                                                       15

<210> SEQ ID NO 150
<211> LENGTH: 18
<212> TYPE: DNA
<213> ORGANISM: Artificial Sequence
<220> FEATURE:
<223> OTHER INFORMATION: Description of artificial sequence: synthetic
      probe

<400> SEQUENCE: 150
ttggatgtaa attattgt                                                    18

<210> SEQ ID NO 151
<211> LENGTH: 18
<212> TYPE: DNA
<213> ORGANISM: Artificial Sequence
<220> FEATURE:
<223> OTHER INFORMATION: Description of artificial sequence: synthetic
      probe

<400> SEQUENCE: 151
atgtaaacta ttgttgct                                                    18

<210> SEQ ID NO 152
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 152
aatgctgagt tggatc                                                      16

<210> SEQ ID NO 153
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 153
atgctcgagt tggat                                                       15

<210> SEQ ID NO 154
<211> LENGTH: 14
<212> TYPE: DNA
<213> ORGANISM: Artificial Sequence
<220> FEATURE:

```
<223> OTHER INFORMATION: Description of artificial sequence: synthetic
      probe

<400> SEQUENCE: 154
ctctcgtggc ttca                                                        14

<210> SEQ ID NO 155
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 155
ctctcatggc ttcaa                                                       15

<210> SEQ ID NO 156
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 156
ttgtgcagtt aaacat                                                      16

<210> SEQ ID NO 157
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 157
tgtgcaggta aacat                                                       15

<210> SEQ ID NO 158
<211> LENGTH: 14
<212> TYPE: DNA
<213> ORGANISM: Artificial Sequence
<220> FEATURE:
<223> OTHER INFORMATION: Description of artificial sequence: synthetic
      probe

<400> SEQUENCE: 158
catgggtcct ttca                                                        14

<210> SEQ ID NO 159
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 159
atgggtccat tcaga                                                       15

<210> SEQ ID NO 160
<211> LENGTH: 15
<212> TYPE: DNA
<213> ORGANISM: Artificial Sequence
<220> FEATURE:
<223> OTHER INFORMATION: Description of artificial sequence: synthetic
```

```
                              -continued
      probe

<400> SEQUENCE: 160
ccgttctgta accgg                                                15

<210> SEQ ID NO 161
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 161
tccgttttgt aaccg                                                15

<210> SEQ ID NO 162
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 162
attgaagtgg ataagtc                                              17

<210> SEQ ID NO 163
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 163
ttgaagtgga tgaagtg                                              17

<210> SEQ ID NO 164
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 164
taccacgttg tttcaaa                                              17

<210> SEQ ID NO 165
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 165
tttaccacat tgtttc                                               16
```